(12) United States Patent
Cardinali et al.

(10) Patent No.: US 11,672,917 B2
(45) Date of Patent: Jun. 13, 2023

(54) DRUG CARTRIDGE WITH DRIVE SYSTEM

(71) Applicant: Insulet Corporation, Acton, MA (US)

(72) Inventors: Steven Cardinali, Tewksbury, MA (US); David Nazzaro, Groveland, MA (US); Daniel Allis, Boxford, MA (US); Maureen McCaffrey, Boston, MA (US)

(73) Assignee: INSULET CORPORATION, Acton, MA (US)

( * ) Notice: Subject to any disclaimer, the term of this patent is extended or adjusted under 35 U.S.C. 154(b) by 433 days.

(21) Appl. No.: 17/039,570

(22) Filed: Sep. 30, 2020

(65) Prior Publication Data

US 2021/0016015 A1  Jan. 21, 2021

Related U.S. Application Data

(63) Continuation of application No. 15/993,800, filed on May 31, 2018, now Pat. No. 10,874,803.

(51) Int. Cl.
*A61M 5/315* (2006.01)

(52) U.S. Cl.
CPC ........ *A61M 5/31576* (2013.01); *A61M 5/315* (2013.01); *A61M 5/31501* (2013.01); *A61M 5/31535* (2013.01); *A61M 5/31566* (2013.01); *A61M 5/31593* (2013.01); *A61M 5/31511* (2013.01); *A61M 5/31533* (2013.01); *A61M 5/31543* (2013.01)

(58) Field of Classification Search
CPC .......... A61M 5/31543; A61M 5/31533; A61M 5/31511; A61M 5/31593; A61M 5/31566; A61M 5/31535; A61M 5/31501; A61M 5/31576; A61M 5/315; A61M 5/1422; A61M 2205/0266
USPC ........................................................ 604/209
See application file for complete search history.

(56) References Cited

U.S. PATENT DOCUMENTS

| 2,752,918 A | 7/1956 | Uytenbogaart et al. |
| 3,464,359 A | 9/1969 | King |

(Continued)

FOREIGN PATENT DOCUMENTS

| CN | 102498292 B | 7/2015 |
| CN | 204972511 U | 1/2016 |

(Continued)

OTHER PUBLICATIONS

International Search Report and Written Opinion for Application No. PCT/US2019/059854, dated Aug. 26, 2020, 15 pages.

(Continued)

*Primary Examiner* — Bhisma Mehta
*Assistant Examiner* — Nidah Hussain
(74) *Attorney, Agent, or Firm* — Goodwin Procter LLP

(57) ABSTRACT

Drive systems for a drug delivery device are provided. The drive systems can be positioned within a container that stores a liquid drug to be delivered to a user. The drive systems can be coupled to a plunger positioned within the container. The drive systems can be incrementally advanced to drive the plunger further into the container, thereby expelling a portion of the stored liquid drug from the container for delivery to the user. The container can be any type of container including a pre-filled, standardized drug cartridge. The drive systems and container can be components of a wearable drug delivery device.

20 Claims, 46 Drawing Sheets

(56) References Cited

U.S. PATENT DOCUMENTS

| | | | |
|---|---|---|---|
| 4,277,226 | A | 7/1981 | Archibald |
| 4,475,905 | A | 10/1984 | Himmelstrup |
| 4,671,429 | A | 6/1987 | Spaanderman et al. |
| 4,991,743 | A | 2/1991 | Walker |
| 5,277,338 | A | 1/1994 | Divall |
| 5,628,309 | A | 5/1997 | Brown |
| 6,740,059 | B2 | 5/2004 | Flaherty |
| 7,137,964 | B2 | 11/2006 | Flaherty |
| 7,951,114 | B2 | 5/2011 | Rush et al. |
| 8,267,921 | B2 | 9/2012 | Yodfat et al. |
| 8,905,995 | B2 | 12/2014 | Mernoe |
| 8,920,376 | B2 | 12/2014 | Caffey et al. |
| 9,539,596 | B2 | 1/2017 | Ikushima |
| 10,441,723 | B2 | 10/2019 | Nazzaro |
| 10,695,485 | B2 | 6/2020 | Nazzaro |
| 2003/0055380 | A1 | 3/2003 | Flaherty |
| 2003/0198558 | A1 | 10/2003 | Nason et al. |
| 2007/0073236 | A1 | 3/2007 | Mernoe et al. |
| 2007/0088271 | A1 | 4/2007 | Richards |
| 2008/0294040 | A1 | 11/2008 | Mohiuddin et al. |
| 2009/0326472 | A1 | 12/2009 | Carter et al. |
| 2011/0073620 | A1 | 3/2011 | Verrilli |
| 2012/0095394 | A1* | 4/2012 | Kakiuchi .............. A61M 5/284 604/89 |
| 2012/0172817 | A1 | 7/2012 | Bruggemann et al. |
| 2012/0209207 | A1 | 8/2012 | Gray et al. |
| 2013/0177455 | A1 | 7/2013 | Kamen et al. |
| 2013/0296792 | A1 | 11/2013 | Cabiri |
| 2015/0051487 | A1 | 2/2015 | Uber et al. |
| 2016/0129190 | A1 | 5/2016 | Haitsuka |
| 2016/0213851 | A1 | 7/2016 | Weibel et al. |
| 2017/0290975 | A1 | 10/2017 | Barmaimon et al. |
| 2018/0185579 | A1 | 7/2018 | Joseph et al. |
| 2019/0192782 | A1 | 6/2019 | Pedersen et al. |
| 2019/0365993 | A1 | 12/2019 | Staub et al. |
| 2020/0009315 | A1 | 1/2020 | Brouet et al. |
| 2020/0345931 | A1 | 11/2020 | Gray et al. |

FOREIGN PATENT DOCUMENTS

| | | |
|---|---|---|
| CN | 105764543 B | 7/2016 |
| CN | 206175149 U | 5/2017 |
| CN | 107096091 A | 8/2017 |
| CN | 108472441 A | 8/2018 |
| DE | 102005040344 A1 | 3/2007 |
| EP | 1874390 B1 | 10/2014 |
| JP | H06296690 A | 10/1994 |
| JP | 2009514580 A | 4/2009 |
| JP | 2017513577 A | 6/2017 |
| WO | 9320864 A1 | 10/1993 |
| WO | 2004032994 A2 | 4/2004 |
| WO | 2009141005 A1 | 11/2009 |
| WO | 2010022069 A2 | 2/2010 |
| WO | 2010077279 A1 | 7/2010 |
| WO | 2011010198 A2 | 1/2011 |
| WO | 2011031458 A1 | 3/2011 |
| WO | 2011069935 A2 | 6/2011 |
| WO | 2013149186 A1 | 10/2013 |
| WO | 2014029416 A1 | 2/2014 |
| WO | 2014179774 A1 | 11/2014 |
| WO | 2015048791 A1 | 4/2015 |
| WO | 2017148855 A1 | 9/2017 |
| WO | 2017187177 A1 | 11/2017 |
| WO | 2021016452 A1 | 1/2021 |

OTHER PUBLICATIONS

International Search Report and Written Opinion for the International Patent Application No. PCT/US2021/055581, dated Feb. 8, 2022, 19 pages.

International Search Report and Written Opinion, Application No. PCT/US2022/016713, dated Aug. 5, 2022, 19 pages.

International Search Report and Written Opinion for International Patent Application No. PCT/US2022/011356, dated Apr. 29, 2022, 19 pages.

International Search Report and Written Opinion for International Patent Application No. PCT/US2022/029012, dated Aug. 19, 2022, 12 pages.

* cited by examiner

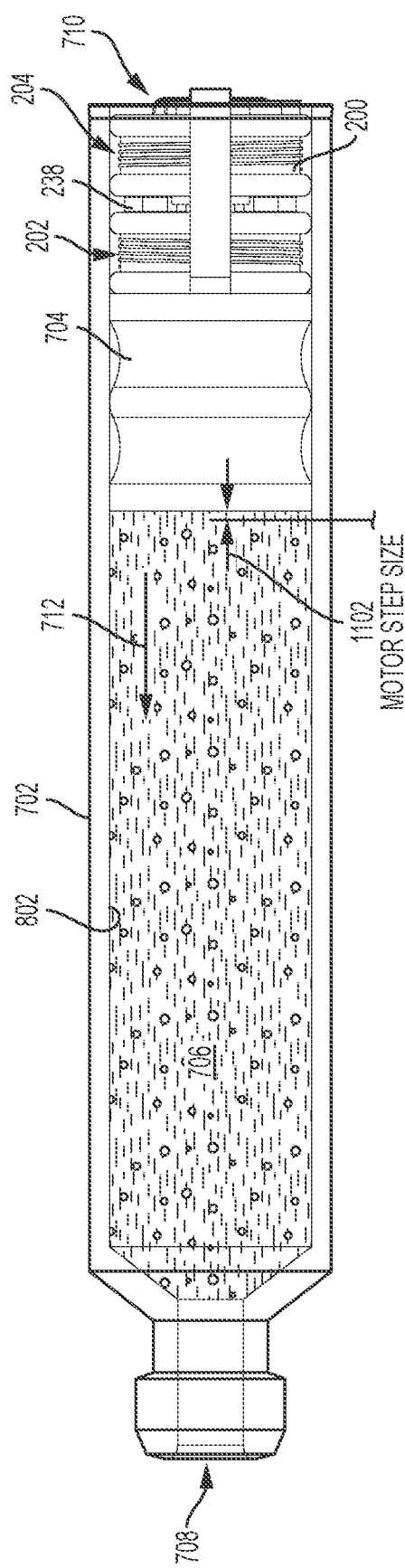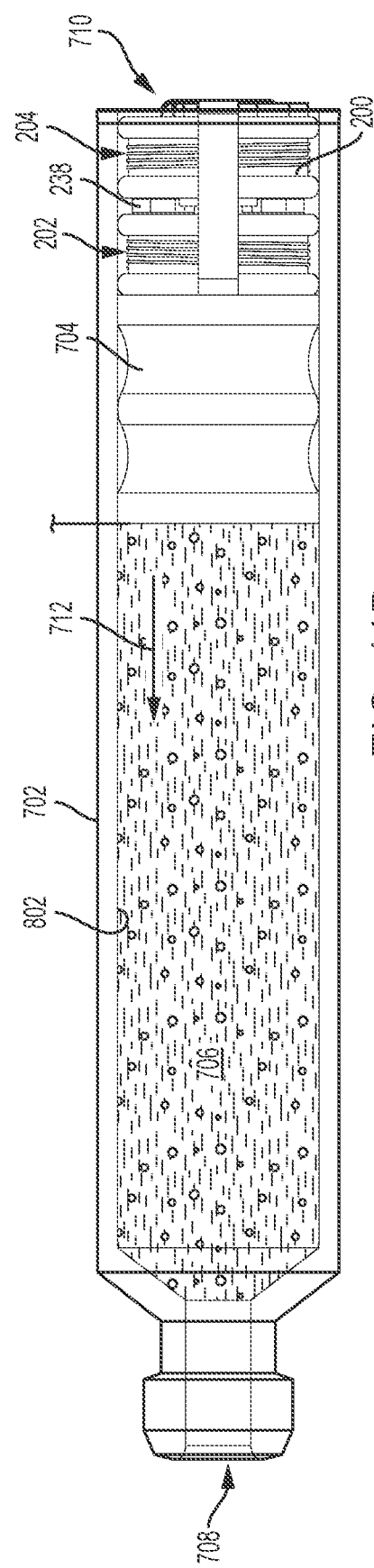

DRUG CARTRIDGE WITH DRIVE SYSTEM

CROSS-REFERENCE TO RELATED APPLICATIONS

This application is a continuation of U.S. patent application Ser. No. 15/993,800, filed May 31, 2018. The contents of the aforementioned application are incorporated herein by reference in their entirety.

TECHNICAL FIELD

Embodiments generally relate to medication delivery. More particularly, embodiments relate to drive systems for use internal to a drug container.

BACKGROUND

Many conventional drug delivery devices include a reservoir for storing a liquid drug. A drive mechanism is operated to expel the stored liquid drug from the reservoir for delivery to a user. Often, the user is required to transfer the liquid drug from a vial or other container to the reservoir before it can be dispensed to the user. It would be advantageous for drug delivery devices to include standardized pre-filled containers (e.g., 3 mL International Organization for Standardization cartridges) for storing and dispensing the liquid drug, to obviate the need for the user to transfer the drug to the drug delivery device while also streamlining order fulfillment by supplying pre-filled drug delivery devices to the user.

Many conventional drive mechanisms, however, use a plunger to expel the liquid drug from the reservoir. Accordingly, the drive mechanism generally has a length equal to a length of the reservoir. When paired with a standardized pre-filled cartridge, these conventional drive mechanisms would cause a length of the drug delivery device to be significantly larger—for example, about twice the length of the cartridge. Increasing the size of the drug delivery device to accommodate pre-filled cartridges and corresponding drive mechanisms leads to a bulky device that is uncomfortable for the user to wear.

Accordingly, there is a need for a drive system for expelling a liquid drug from a standardized, pre-filled cartridge that minimizes any increased size of a drug delivery device, allowing the size and form factor of the drug delivery device to remain compact and user-friendly.

BRIEF DESCRIPTION OF THE DRAWINGS

FIG. 11A illustrates the first exemplary alternate step drive prior to advancing a plunger.

FIG. 11B illustrates the first exemplary alternate step drive after advancing the plunger.

DETAILED DESCRIPTION

This disclosure presents various systems, components, and methods related to a drive system for expelling a drug from a container. Each of the systems, components, and methods disclosed herein provides one or more advantages over conventional systems, components, and methods.

Various embodiments include a drive system for a drug delivery device. The drive system can be positioned within a container that stores a liquid drug to be delivered to a user. The drive system can be coupled to a plunger positioned within the container. The drive system can be incrementally advanced to drive the plunger further into the container, thereby expelling a portion of the stored liquid drug from the container for delivery to the user. The container can be any type of container including a pre-filled, standardized drug cartridge. The drive system and container can be components of a wearable drug delivery device. Other embodiments are disclosed and described.

Figure 1A:
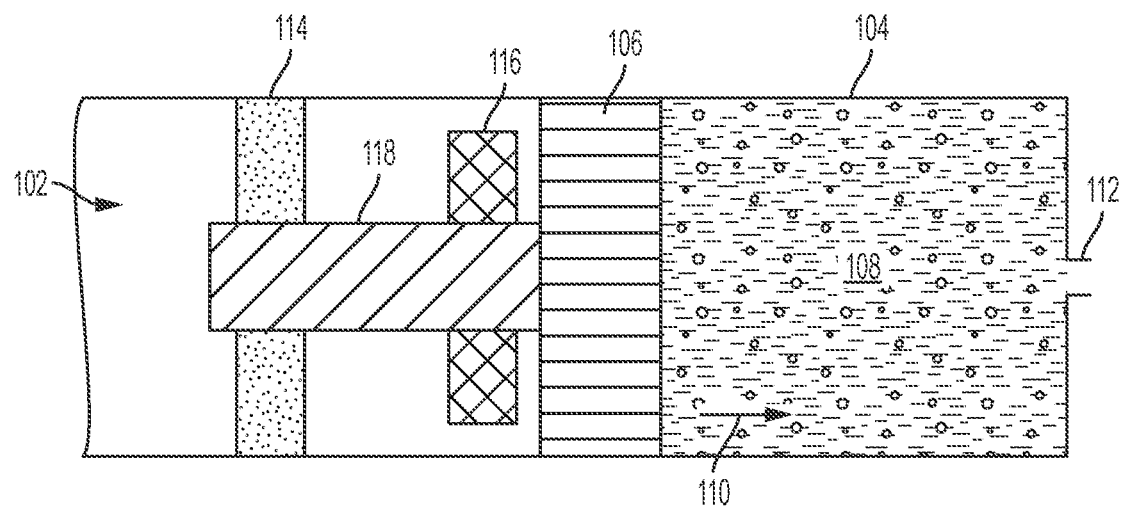
FIG. 1A illustrates a first stage of operation of a schematic representation of an alternate step drive.

FIGS. 1A-1F illustrate operation of an exemplary alternate step drive or alternate braking step drive 102. FIGS. 1A-1F illustrate the alternate step drive 102 schematically. As shown in FIG. 1A, the alternate step drive 102 can be positioned within a cartridge 104 and can be coupled to a plunger 106. The cartridge 104 can represent any type of cartridge, vial, or container for holding or storing a liquid 108 such as, for example, a liquid drug or other therapeutic agent. The plunger 106 can be formed from a rubber material. The plunger 106 can form a seal with the cartridge 104 to retain and store the liquid drug 108. When the plunger 106 is advanced in a direction 110, the plunger 106 can expel a portion of the liquid drug 108 from an exit port or outlet 112 of the cartridge 104 for delivery to a patient or user.

The alternate step drive 102 can be operated to advance the plunger 106 in the direction 110. Accordingly, the alternate step drive 102 can operate as a drive system (or a portion thereof) that can determine an amount of the liquid drug 108 that is delivered to the user by regulating advancement of the plunger 106 to expel the liquid drug 108 from the container 104.

The alternate step drive 102 can include a first brake member or component 114, a second brake member or component 116, and a connector member or component 118. The first brake component 114, the second brake component 116, and the connector component 118 can be operated or actuated independently. The first brake component 114 and the second brake component 116 can each expand and retract radially. When expanded, the first brake component 114 can be pressed against the container 104 to restrict movement. When retracted, the first brake component 114 can allow movement by no longer being pressed against the cartridge 104. The second brake member 116 can similarly expand and retract radially to restrict and allow movement, respectively.

The connector component 118 can be coupled to the first brake component 114 and the second brake component 116. The connector component 118 and/or the second brake component 116 can be coupled to the plunger 106. The connector component 118 can expand and retract along an axis approximately perpendicular to an axis about which both the first and second brake components 114 and 116 can expand and retract. As an example, the connector component 118 can expand and retract along an axis that is approximately parallel to the direction 110 and the first and second brake components 114 and 116 can expand and contract along an axis that is approximately perpendicular to the direction 110. The expansion and contraction of the connector component 118 can provide a driving force for advancing the plunger 106 in the direction 110. By actuating the first brake component 114, the second brake component 116, and the connector component 118 according to a predetermined sequence, the alternate step drive 102, and consequently the plunger 106, can be incrementally advanced in the direction 110.

FIGS. 1A-1F illustrate a sequence of steps or operations implemented by the alternate step drive 102 to provide a driving force on the plunger 106. FIG. 1A shows a first operational state of the alternate step drive 102. In particular, the first brake component 114 is extended and can be pressed against or coupled to the interior of the cartridge 104. The second brake component 116 is retracted and is not pressed against or otherwise coupled to the interior of the cartridge 104. The connector component 118 can be retracted.

Figure 1B:
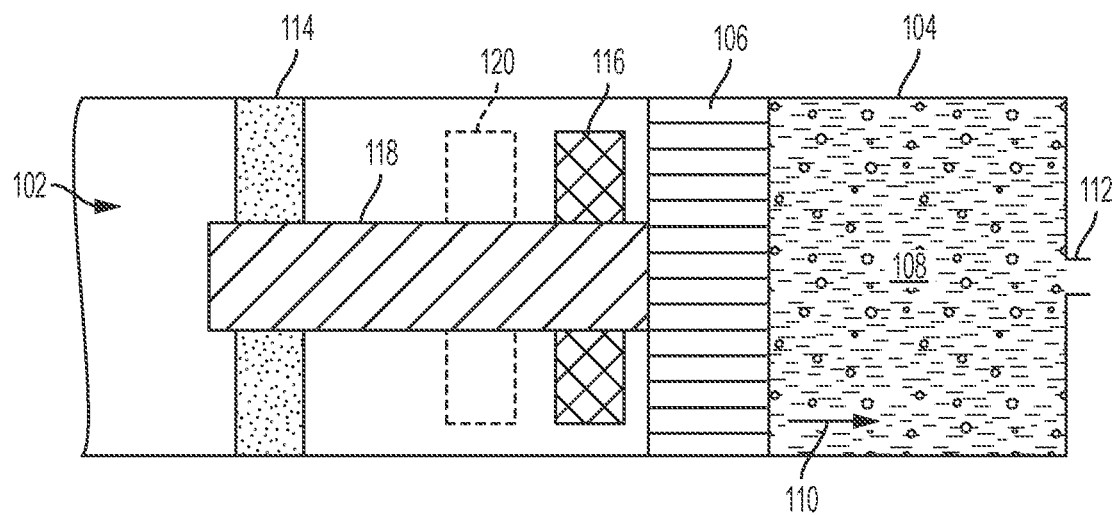
FIG. 1B illustrates a second stage of operation of the schematic representation of the alternate step drive.

FIG. 1B illustrates a second operational state of the alternate step drive 102, or a subsequent operational state of the alternate step drive 102 relative to the depiction of the alternate step drive 102 in FIG. 1A. As shown, the first brake component 114 is extended and can be pressed against or coupled to the interior of the cartridge 104. The second brake component 116 is retracted and is not pressed against or otherwise coupled to the interior of the cartridge 104. The connector component 118 is extended and has moved the second brake component 116 and the plunger 106 in the direction 110. Outline 120 represents the prior position or location of the second brake component 116 to illustrate the movement of the second brake component 116 when the connector component 118 is expanded.

As shown in FIG. 1B, the plunger 106 can be advanced in the direction 110 when the first brake component 114 is extended to function as an engaged brake, the second brake component 116 is retracted to function as a disengaged brake, and the connector component 118 is expanded. As a result, the plunger 106 is advanced further into the cartridge 104, causing a portion of the liquid drug 108 to be expelled out of the cartridge 104 through the exit port 112.

Figure 1C:
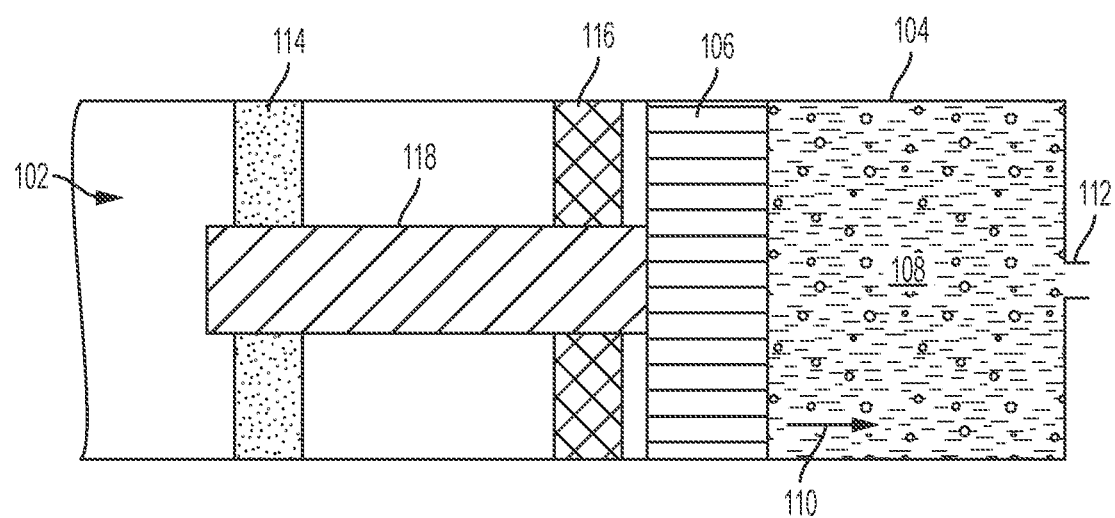
FIG. 1C illustrates a third stage of operation of the schematic representation of the alternate step drive.

FIG. 1C illustrates a third operational state of the alternate step drive 102, or a subsequent operational state of the alternate step drive 102 relative to the depiction of the alternate step drive 102 in FIG. 1B. As shown, the first brake component 114 is extended and can be pressed against or coupled to the interior of the cartridge 104. The second brake component 116 is also extended and can be pressed against or coupled to the interior of the cartridge 104. The connector component 118 remains extended. With the first and second brake components 114 and 116 extended, the alternate step drive 102 does not advance the plunger 106 in the direction 110.

Figure 1D:
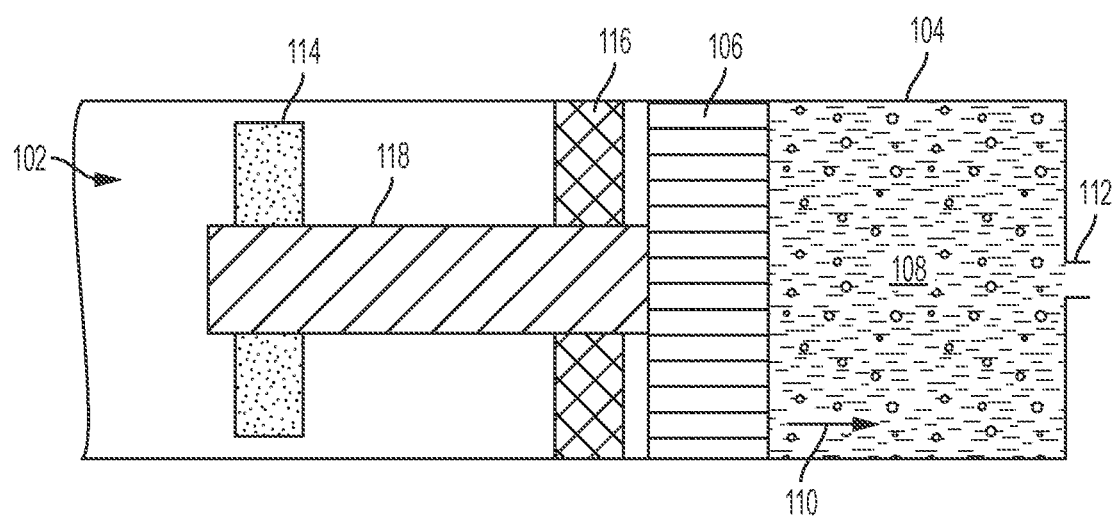
FIG. 1D illustrates a fourth stage of operation of the schematic representation of the alternate step drive.

FIG. 1D illustrates a fourth operational state of the alternate step drive 102, or a subsequent operational state of the alternate step drive 102 relative to the depiction of the alternate step drive 102 in FIG. 1C. As shown, the first brake component 114 is retracted. The second brake component 116 is extended and can be pressed against or coupled to the interior of the cartridge 104. The connector component 118 remains extended. As shown in FIG. 1D, the alternate step drive 102 does not advance the plunger 106 in the direction 110.

Figure 1E:
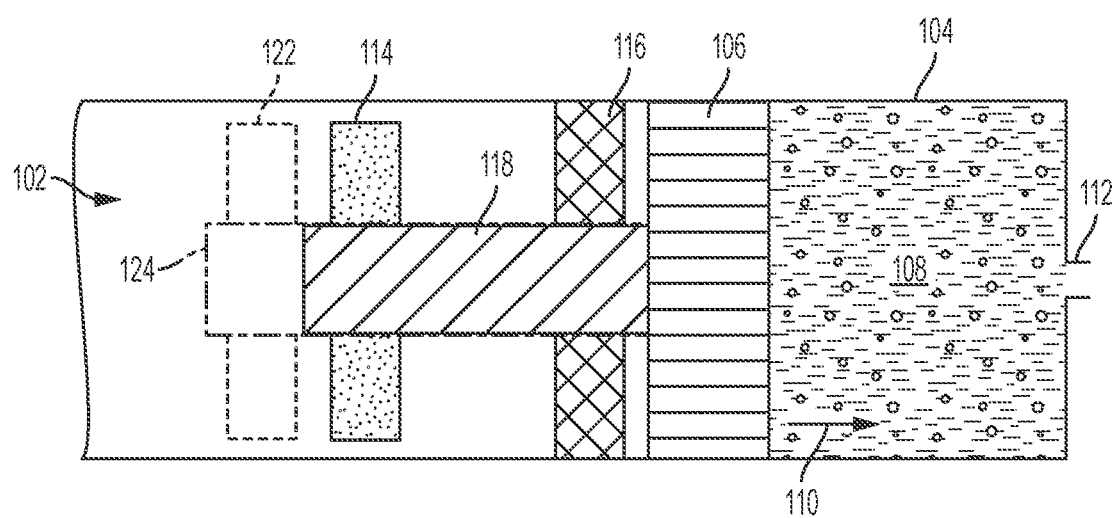
FIG. 1E illustrates a fifth stage of operation of the schematic representation of the alternate step drive.

FIG. 1E illustrates a fifth operational state of the alternate step drive 102, or a subsequent operational state of the alternate step drive 102 relative to the depiction of the alternate step drive 102 in FIG. 1D. As shown, the second brake component 116 is extended and can be pressed against or coupled to the interior of the cartridge 104. The first brake component 114 is retracted. The connector component 118 is also retracted. As a result, the first brake component 114 is advanced in the direction 110 and is moved closer to the second brake component 116. Outline 122 represents the prior position or location of the first brake component 114 to illustrate the movement of the first brake component 114 when the connector component 118 is retracted. Outline 124 represents a prior position or location of an end of the connector component 118 to illustrate movement of the connector component 118 when it is retracted.

Figure 1F:
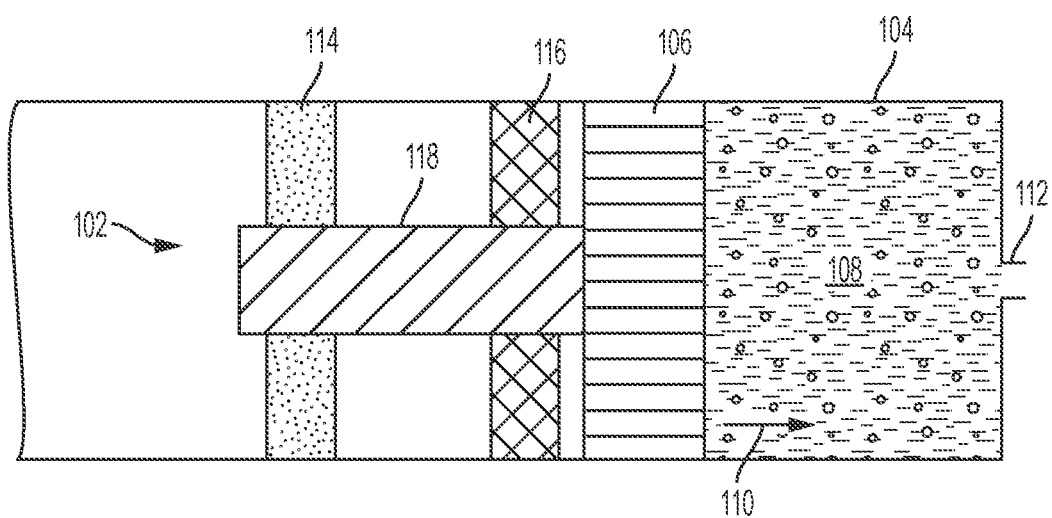
FIG. 1F illustrates a sixth stage of operation of the schematic representation of the alternate step drive.

FIG. 1F illustrates a sixth operational state of the alternate step drive 102, or a subsequent operational state of the alternate step drive 102 relative to the depiction of the alternate step drive 102 in FIG. 1E. As shown, the first and second brake components 114 and 116 are extended and can each be pressed against or coupled to the interior of the cartridge 104. The connector component 118 remains retracted. FIGS. 1A-1F can represent one complete cycle of operations of the alternate step drive 102 for advancing the plunger 106 by a fixed amount in the direction 110. The alternate step drive 102 can repeat the sequence of operational states shown in FIGS. 1A-1F to further advance the plunger 106 to deliver a second portion of the liquid drug 108 to the user.

The alternate step drive 102 can be controlled to expel any portion of the liquid drug 108 to the user. As an example, the alternate step drive can be controlled to deliver substantially all of the liquid drug 108 to the user in a single dose. Alternatively, the alternate step drive 102 can be controlled to deliver the liquid drug 108 to the user over two or more doses (e.g., over multiple doses or multi-doses). In various embodiments, the liquid drug 108 can be insulin and the alternate step drive 102 can operate as a drive system for an insulin delivery system capable of precisely controlling bolus or basal amounts of insulin to the user. The alternate step drive 102 can be configured to provide a desired step size for advancing the plunger 106 to provide precise control of the amount of the liquid drug 108 expelled from the container 104.

As shown in FIGS. 1A-1F and disclosed herein, each of the first and second brake components 114 and 116 can operate as a radial grip that allows the alternate step drive 102 to either (a) apply a force to the inside of the cartridge 104 by fixing one or both of the first and second brake components 114 and 116 in place or (b) retract from the inside of the cartridge 104 to allow a region of the alternate step drive 102 in proximity to one of the first and second brake components 114 and 116 to move freely through the cartridge 104 in the direction 110. The connector component 118 can retract to bring the first and second brake components 114 and 116 closer together. When the connector component 118 expands, the connector component 118 can drive the first and second brake components 114 and 116 further part—and can provide a driving force on the plunger 106 to drive it in the direction 110. Accordingly, as shown in FIGS. 1A-1F and disclosed herein, the first and second brake components 114 and 116 and the connector component 118 can be controlled to expand and retract in a particular order to allow the alternate step drive 102 to advance further into the cartridge 104, thereby enabling the liquid drug 108 to be expelled by the plunger 106.

Figure 2:
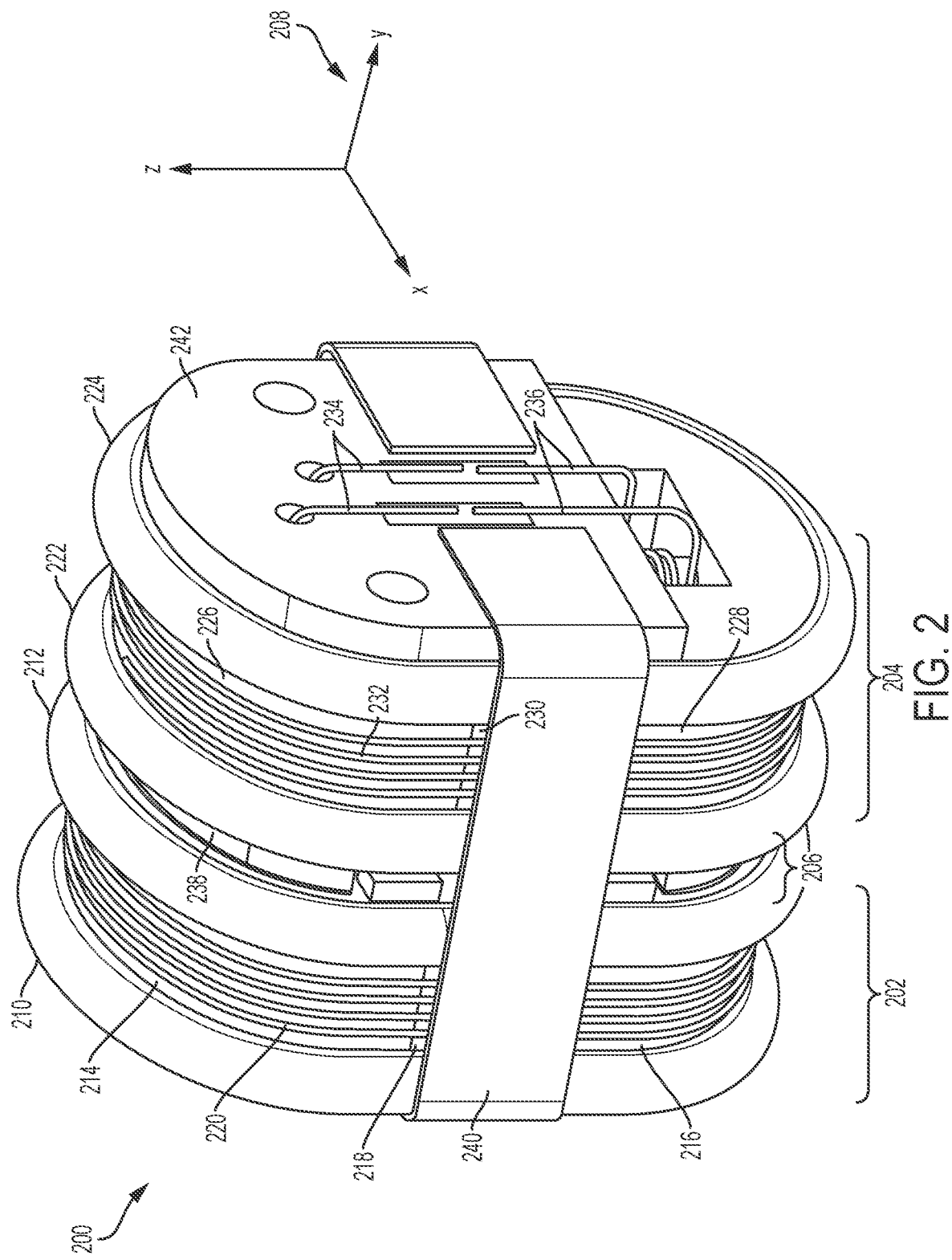
FIG. 2 illustrates a first view of a first exemplary alternate step drive.

FIG. 2 illustrates a first exemplary alternate step drive 200. The first exemplary alternate step drive 200 can represent an implementation of the alternate step drive 102. FIG. 2 shows a first view of the alternate step drive 200. As shown in FIG. 2, the alternate step drive 200 can include a first brake member or component 202 and a second brake member or component 204. A connector member or component 206 can at least be partially disposed between the first and second brake members 202 and 204. FIG. 2 further includes a coordinate system 208 for reference having an x-axis, a y-axis, and a z-axis, each of which is perpendicular to any other axis.

The first brake component 202 can include a first rubber component 210, a second rubber component 212, a first non-compressible component 214, a second non-compressible component 216, and a compressible component 218. The compressible component 218 can be positioned between the first and second non-compressible components 214 and 216. The compressible component 218 can be formed of a rubber material, a foam material, an elastic material component, or metal springs, or any combination thereof. The first and second non-compressible components 216 and 218 can be formed from a plastic material or a metal material. In various embodiments, the first and second rubber components 210 and 212 can be formed of a material other than rubber such as any soft material capable of providing a frictional surface when pressed against an inner wall of a container.

The first and second rubber components 210 and 212 can be positioned around the outside or periphery of both the first and second non-compressible components 214 and 216. As shown in FIG. 2, the first rubber component 210 can be positioned around a first end of the first brake component 202 and the second rubber component 212 can be positioned around a second end of the first brake component 202. A wire 220 can be wrapped around the first brake component 202. Specifically, the wire 220 can be wrapped around the first and second non-compressible components 214 and 216. The wire 220 can be wrapped around the first and second non-compressible components 214 and 216 any number of times. The wire 220 can be a shape memory alloy (SMA) wire or other wire capable of contracting based on, for example, application of a current.

In various embodiments, the wire 220 can be a Nitinol wire. When a current is applied to the Nitinol wire 220, the Nitinol wire 220 can contract. When the Nitinol wire 220 contracts, the Nitinol wire 220 can draw the first and second non-compressible components 214 and 216 together while compressing the compressible component 220. As a result, applying a current to the Nitinol wire 220 can cause the first brake component 202 to contract in the z-dimension.

When the current is removed from the Nitinol wire 220, the Nitinol wire 220 can expand or relax. In turn, the compressible material 218 can expand to apply a force to push the first and second non-compressible components 214 and 216 away from one another. As a result, the first brake component 202 can expand in the z-dimension. When the first brake component 202 expands, the first and second rubber components 210 and 212 can be pressed against the inner wall(s) of a drug container (not shown for simplicity). Pressing the first and second rubber components 210 and 212 against the inner wall(s) of a drug container can prevent or restrict movement of the first brake component 202 in the y-dimension.

The second brake component 204 can include features similar to the first brake component 202 and can operate in a manner similar to the first brake component 202. In particular, the second brake component 204 can include a first rubber component 222, a second rubber component 224, a first non-compressible component 226, a second non-compressible component 228, and a compressible component 230, each arranged in a manner similar to the corresponding component of the first brake component 202 and formed from a material similar to the corresponding component of the first brake component 202.

The second brake component 204 can further include a wire 232 wrapped around the first and second non-compressible components 226 and 228. In various embodiments, the wire 232 can be a SMA wire such as, for example, a Nitinol wire. Accordingly, by applying a current to the Nitinol wire 232, the second brake component 204 can be contracted in the z-dimension and by removing the current the second brake component 204 can be expanded in z-dimension. As with the first brake component 202, the second brake component 204 can be similarly controlled to allow or restrict movement in the y-dimension by causing the first and second rubber components 222 and 224 to engage or disengage from the internal wall(s) of a drug container.

The alternate step drive 200 can further include a wire 234 and a wire 236. The wires 234 and 236 can be routed through internal portions of the alternate step drive (as disclosed further herein). The wires 234 and 236 can also be SMA wires such as, for example, Nitinol wires that can contract and compress the connector component 206. As an example, the connector component 206 can include a compressible material 238 which can be, for example, a rubber material. When currents are applied to the Nitinol wires 234 and 236, the first non-compressible components 214 and 226 can be drawn together and the second non-compressible components 216 and 228 can be drawn together, respectively, thereby compressing the compressible material 238 in the y-dimension. By removing the current from the Nitinol wires 234 and 236, the compressible material 238 can be allowed to expand in the y-dimension. As a result, the first non-compressible components 214 and 226 can be pushed away from one another and the second non-compressible components 216 and 228 can be pushed away from one another.

The alternate step drive 200 can be controlled to move along the y-dimension (e.g., along the interior of a drug container) by alternating the application of currents to the Nitinol wires 220, 232, 234, and 236. To do so, the first and second brake components 202 and 204 can selectively engage and disengage the interior portion of the drug container to either allow movement or restrict movement in the y-dimension. Further, the connector component 206 can be controlled to move the first and second brake components 202 and 204 in the y-dimension.

As further shown in FIG. 2, the alternate step drive 200 can include a protector component 240. The protector component 240 can be wrapped around the first and second brake components 202 and 204 and can be formed of a plastic material or a metal material. The protector component 240 can prevent over extension of the alternate step drive 200 in the y-dimension by restricting expansion.

The alternate step drive can also include a controller 242. The controller 242 can be a processor, motherboard, application specific integrated circuit, or any other electrical or circuit component that can be used to control operation of the alternate step drive 200. The controller 242 can be electrically coupled to each of the wires 220, 232, 234, and 236 and can control when a current is applied or not applied to any of the wires 220, 232, 234, and 236. As a result, the controller 242 can control movement of the alternate step drive 200.

Figure 3:
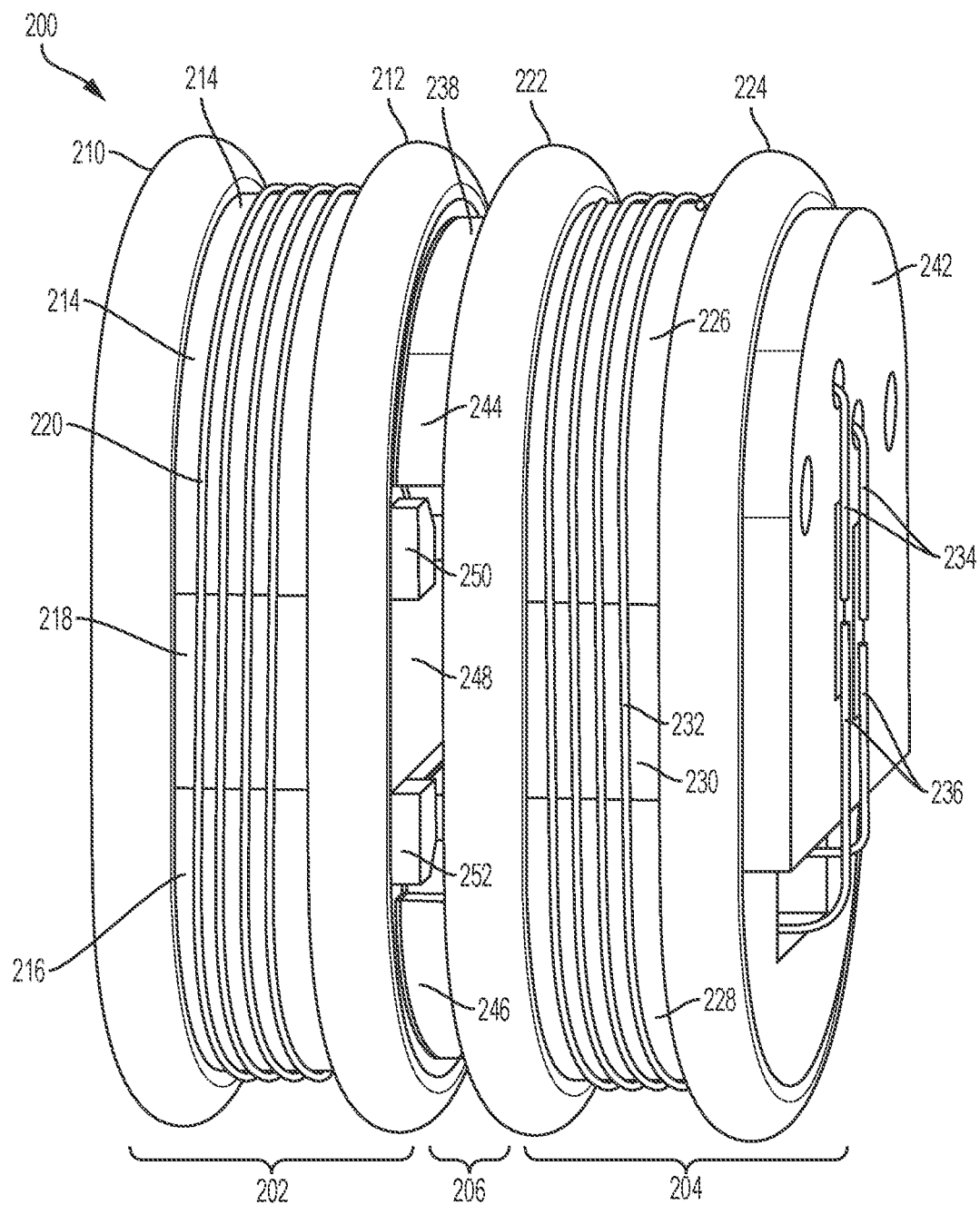
FIG. 3 illustrates a second view of the first exemplary alternate step drive.

FIG. 3 illustrates a partial side view of the alternate step drive 200. The protector component 240 is not shown in FIG. 3 for clarity. As shown in FIG. 3, the compressible component 238 includes a first portion 244 positioned between the first non-compressible components 214 and 226 and a second portion 246 positioned between the second non-compressible components 216 and 228. An opening 248 can be positioned between the first portion 244 and the second portion 246 of the compressible component 238. The first non-compressible component 214 can include a first extension 250 that extends into a portion of the opening 248. The second non-compressible component 216 can include a second extension 252 that also extends into a portion of the opening 248. The first and second extensions 250 and 252 can prevent over compression of the alternate step drive 200. Specifically, the first and second extensions 250 and 252 can prevent the over compression of the first portion 244 and the second portion 246 of the compressible component 238 by the first and second brake components 202 and 204 when the wires 234 and 236 are contracted. In various embodiments, the first and second extensions 250 and 252 can be considered bosses that can prevent over-compression.

Figure 4:
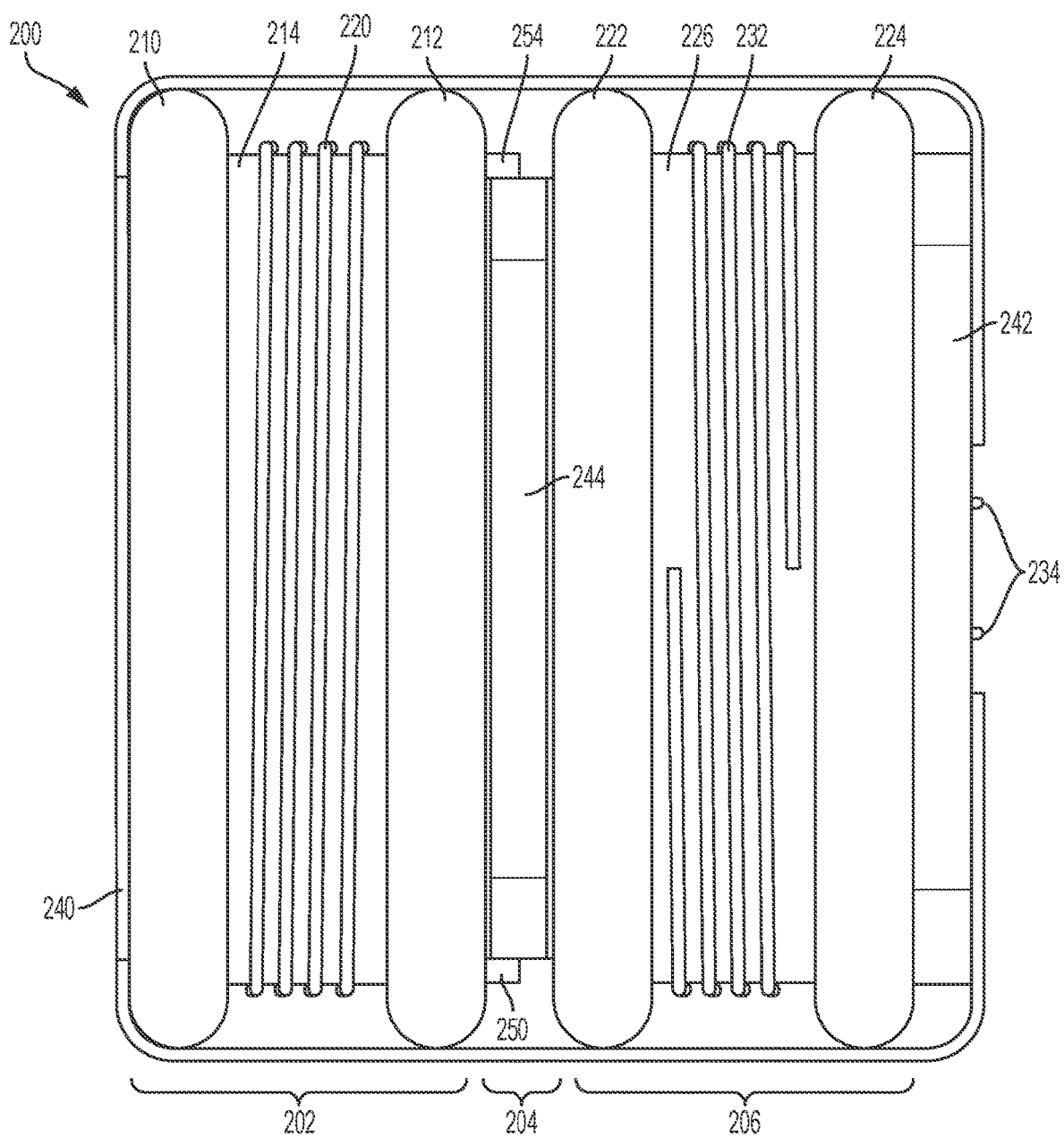
FIG. 4 illustrates a third view of the first exemplary alternate step drive.

FIG. 4 illustrates a top view of the alternate step drive 200. As shown in FIG. 4, the protector component 240 can be positioned around the alternate step drive 200. Specifically, the protector component 240 can be positioned adjacent to the first rubber component 210, around the sides of the alternate step drive 200, and along a portion of the controller 242. As shown, the protector component 240 can prevent over extension of the alternate step drive 200. FIG. 4 further shows the first extension 250 of the first non-compressible component 214 as well as an additional extension 254 of the first non-compressible component 214 (not depicted in FIGS. 2 and 3). The extensions 250 and 254 can prevent over compression of the compressible component 238 as disclosed herein.

Figure 5:
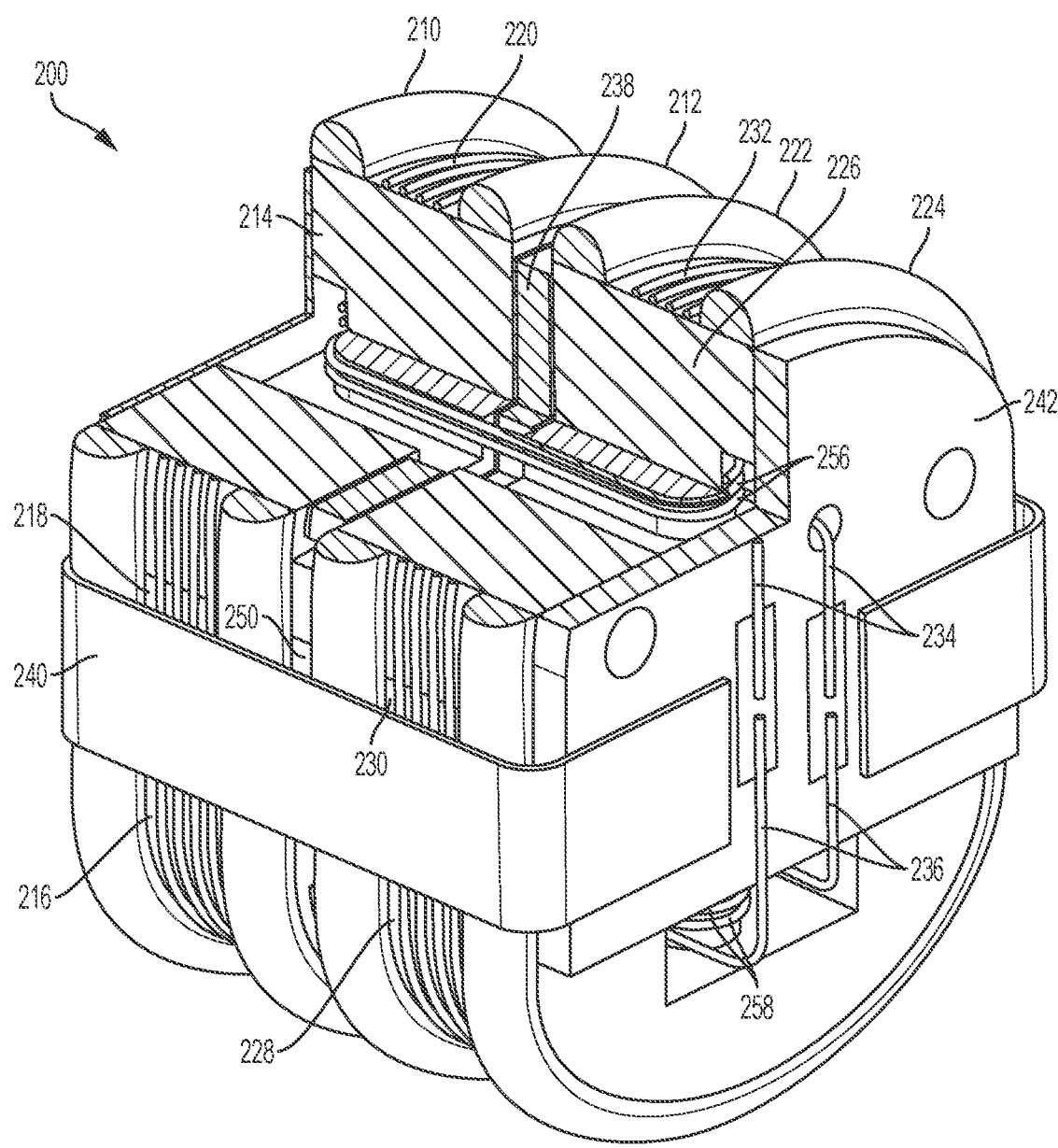
FIG. 5 illustrates a fourth view of the first exemplary alternate step drive.

FIG. 5 illustrates an isometric view of the alternate step drive 200. FIG. 5 shows a cutout of a top portion of the alternate step drive 200 to reveal an exemplary internal arrangement of the components of the alternate step drive 200. In particular, wire 256 is shown as being routed through an interior portion of the alternate step drive 200, through openings in the first non-compressible components 214 and 226 and the compressible component 238. The wire 256 can be coupled to the wire 234 (or can be the same wire). The wire 256 can also be a shape memory wire or other wire capable of contraction such as a Nitinol wire. The wire 256 can be wrapped around the openings as shown any number of times. FIG. 5 shows that by contracting the wire 256, the first non-compressible components 214 and 226 are drawn closer together by compressing the compressible component 238.

In a similar manner, wire 258 can be routed through an interior portion of the alternate step drive 200, through openings in the second non-compressible components 216 and 228 and the compressible component 238. The wire 258 can be coupled to the wire 234 (or can be the same wire) and can also be a shape memory wire or other wire capable of contraction such as a Nitinol wire. Accordingly, by contracting the wire 256, the second non-compressible components 216 and 228 are drawn closer together by compressing the compressible component 238. The wires 256 and 258 can be operated or activated together to compress and expand the connector component 206 of the alternate step drive 200.

Figure 6:
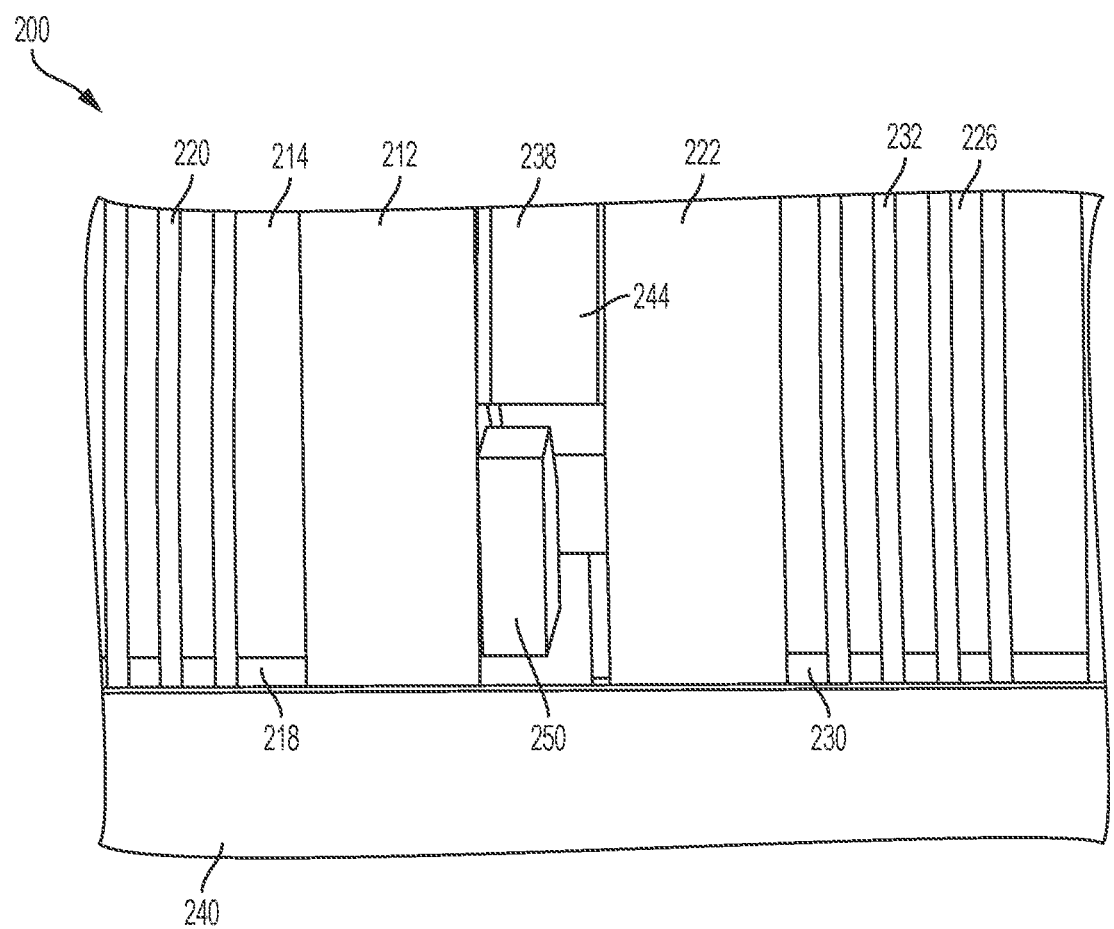
FIG. 6 illustrates a close-up view of a portion of the first exemplary alternate step drive.

FIG. 6 illustrates a close-up view of a portion of the alternate step drive 200. Specifically, FIG. 6 illustrates a close-up view of the first extension 250 of the first non-compressible component 214. As shown in FIG. 6, the first extension 250 is positioned below the first portion 244 of the compressible component 238. The first extension 250 can help prevent over compression of the alternate step drive 200 by preventing the first portion 244 of the compressible component 238 from being compressed by more than a desired amount.

Figure 7:
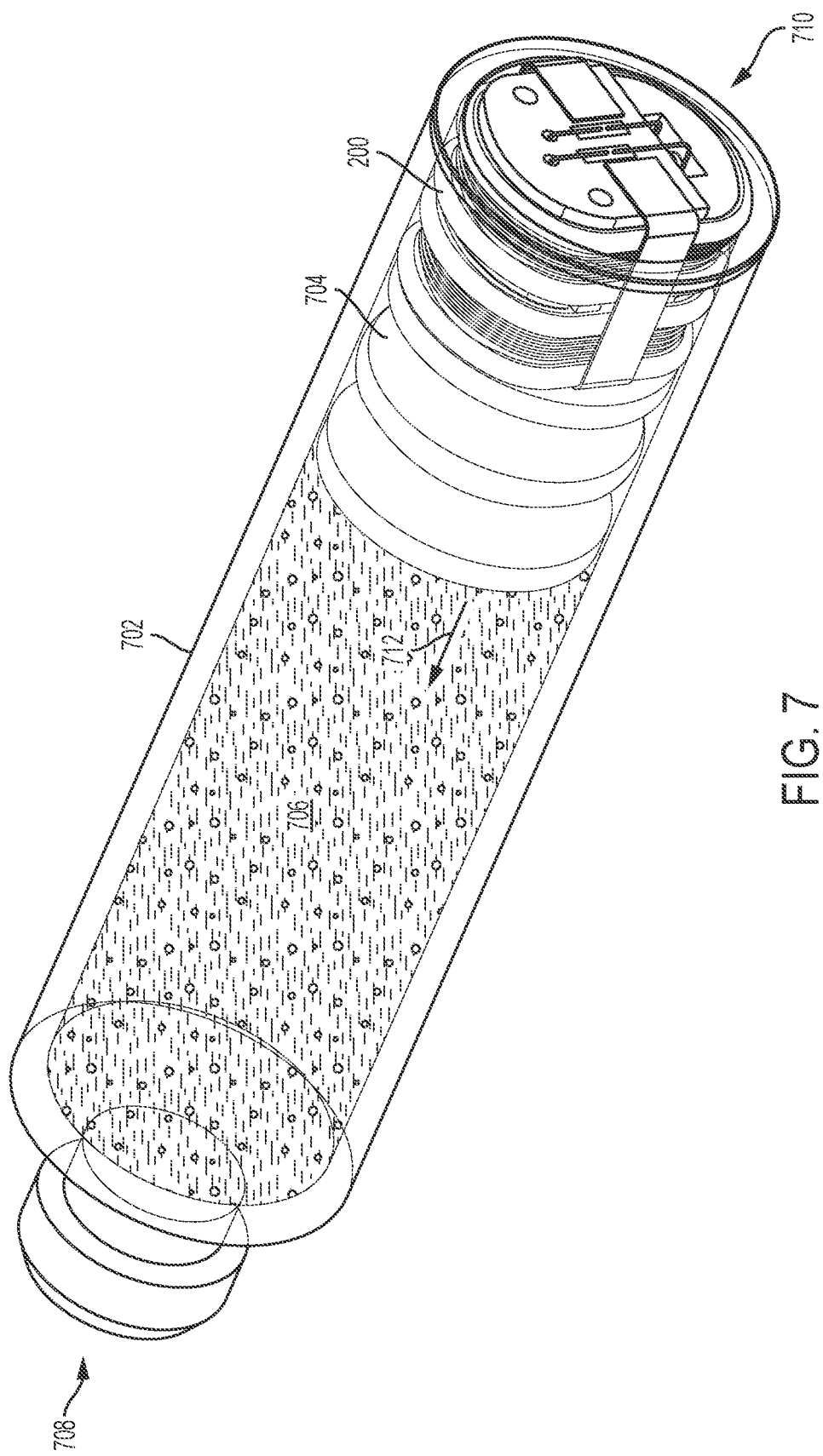
FIG. 7 illustrates a first view of the first exemplary alternate step drive within a container.

FIG. 7 illustrates the alternate step drive 200 within a container 702. FIG. 7 shows a first view of the alternate step drive 200 within the container 702. The container 702 can be any type of cartridge or vial including, for example, an International Organization for Standardization (ISO) drug cartridge (e.g., a 3 mL ISO drug cartridge). The container 702 can include a plunger 704 and can store a liquid 706 that can be any liquid drug or other therapeutic agent. The container 702 can have a first end 708 and a second end 710. The first end 708 can have an opening or port for the liquid drug 708 to exit the container 702. The second end 710 can be open to enable placement of the alternate step drive 200 into the container 702 as shown. The plunger 704 can form a seal with the container 702 to contain the liquid drug 706.

The plunger 704 can be moved in a direction 712 toward the first end 708 of the container 702 to expel the liquid drug 706 from the container 702. As disclosed herein, the alternate step drive 200 can be used to drive the plunger 704 toward the first end 708 of the container 702. The alternate step drive 200 can be coupled to the plunger 704 such that a force applied in the direction 712 by the alternate step drive 200 can cause the plunger 704 to move incrementally in the direction 712.

Figure 8:
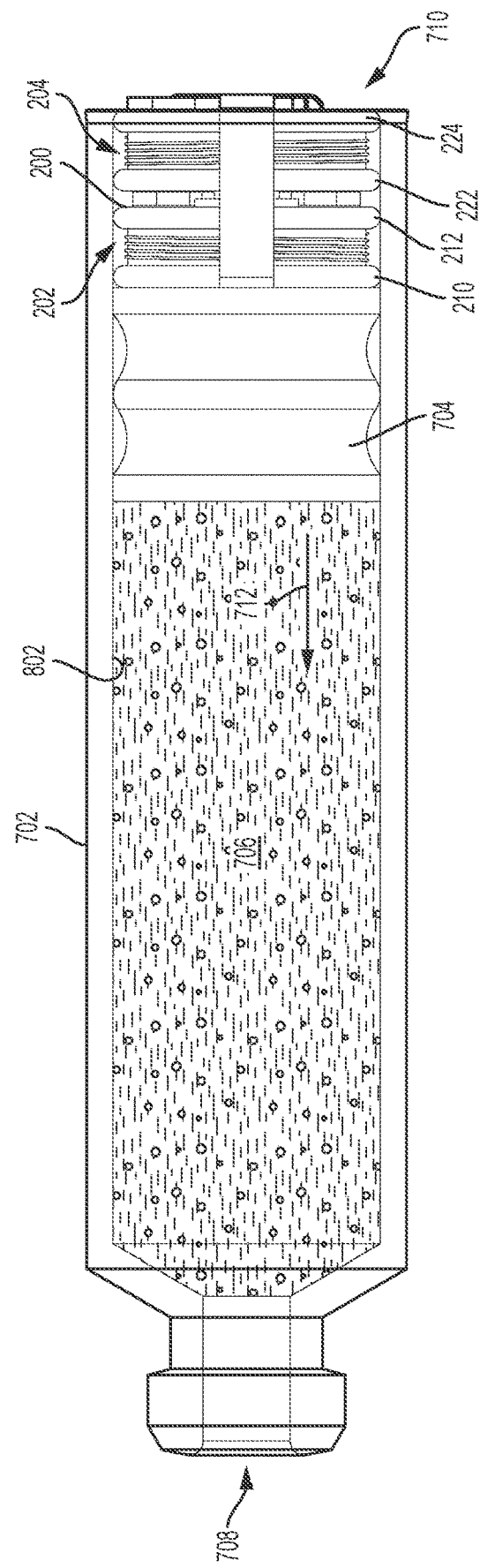
FIG. 8 illustrates a second view of the first exemplary alternate step drive within the container.

FIG. 8 illustrates a side view of the alternate step drive 200 within the container 702. As shown, the plunger 704 is positioned adjacent to an end of the alternate step drive 200—for example, adjacent to the first rubber component 210. FIG. 8 further shows an interior wall or portion 802 of the container 702. The interior wall 802 can be engaged and/or disengaged by the first and second brake components 202 and 204. As shown in FIG. 8, the first and second rubber components 210 and 212 of the first brake component 202 are pressed against the interior wall 802 of the container 702. Similarly, the first and second rubber components 222 and 224 of the second brake component 204 are pressed against the interior wall 802 of the container 702. Accordingly, both the first and second brake components 202 and 204 are engaged with the interior wall 802 to prevent movement of the first and second brake components 202 and 204.

In various embodiments, the plunger 704 can be positioned adjacent to the first rubber component 704 such that movement of the alternate step drive 200 can cause the plunger 704 to be moved. In various embodiments, the plunger 704 can be coupled (e.g., directly attached) to the alternate step drive 200.

Figure 9:
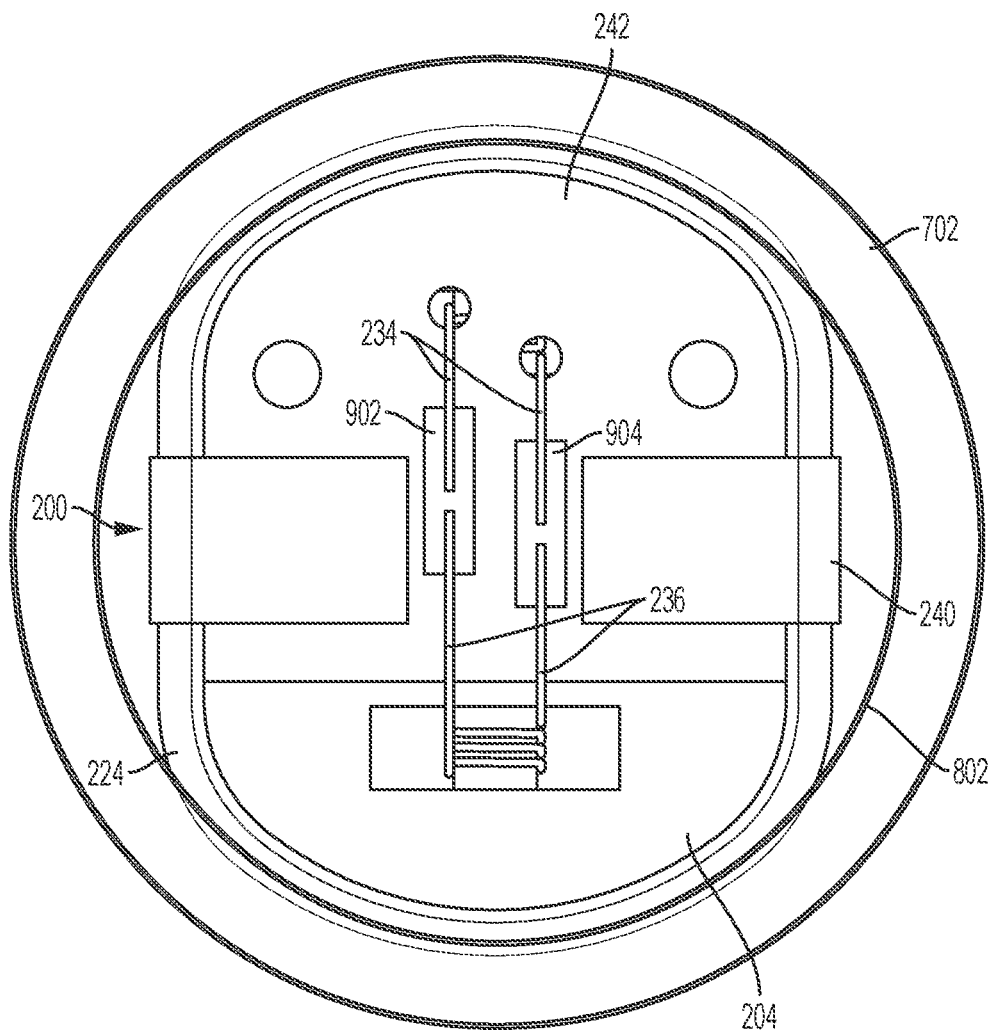
FIG. 9 illustrates a third view of the first exemplary alternate step drive within the container.

FIG. 9 illustrates a rear view of the alternate step drive 200 within the container 702. As shown, the second brake component 204 is engaged with the interior wall 802 of the container 702. Contact pad or terminal 902 couples a first end of wire 234 to a first end of wire 236 and contact pad or terminal 904 couples a second end of wire 234 to a second end of wire 236. The first and second wires 234 and 236 can be controlled to contract and/or expand at substantially the same time or can be controlled independently. When the second brake component 204 is disengaged, as disclosed herein, the first and second rubber components 222 and 224 can be pulled away from the inner wall 802 (e.g., so as to no longer contact the inner wall 802), thereby allowing the second brake component 204 to be moved within the container 702 (e.g., along the y-axis as shown in FIG. 2).

Figure 10:
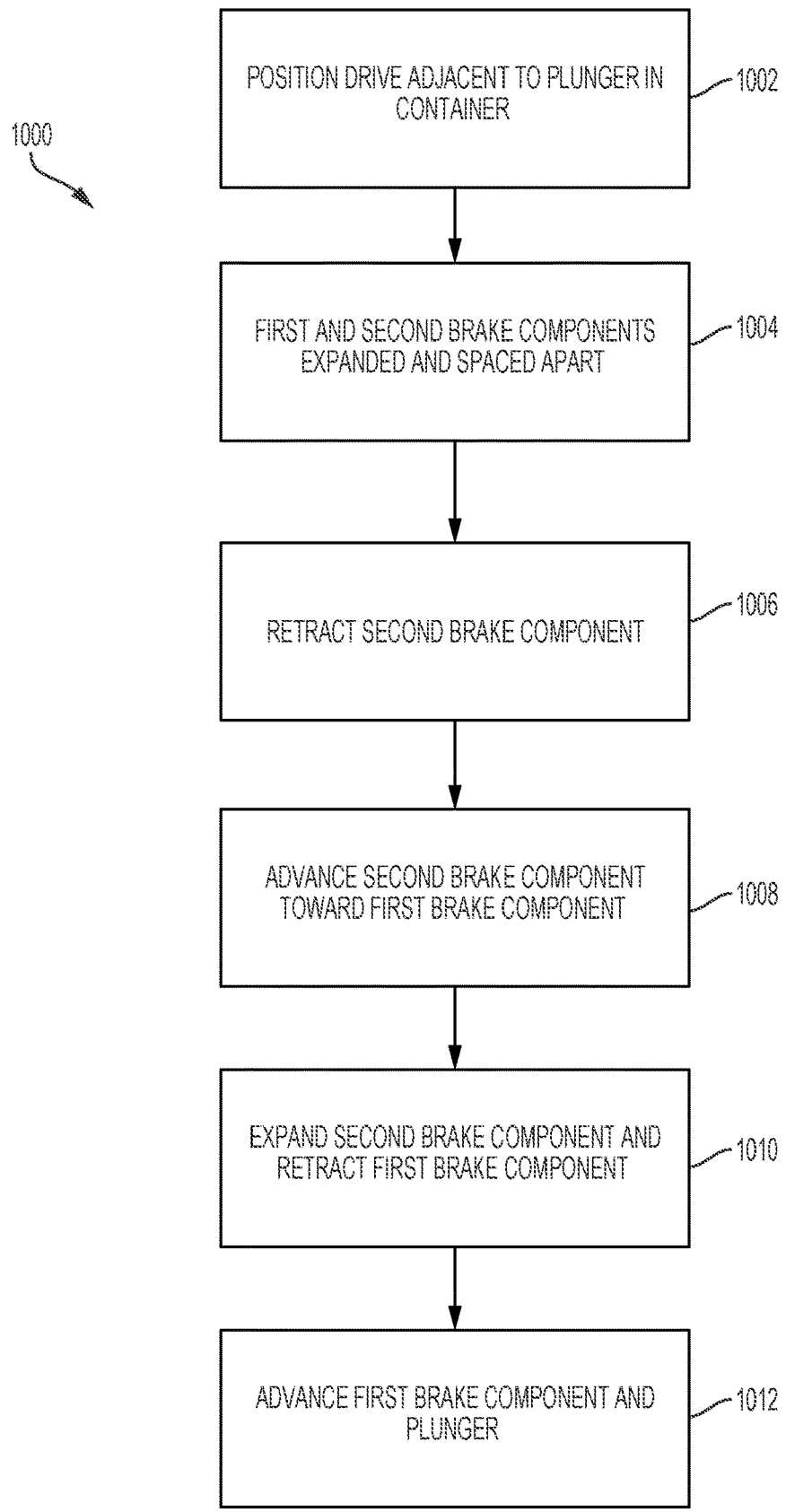
FIG. 10 illustrates an exemplary method of operation for the first exemplary alternate step drive.

FIG. 10 illustrates an exemplary method of operation 1000 for the alternate step drive 200. At 1002, the alternate step drive 200 can be positioned adjacent to a plunger within a drug cartridge holding a liquid drug. In various embodiments, the alternate step drive 200 can be coupled to the plunger directly. The alternate step drive 200 can be positioned within an open end of the drug cartridge. The drug cartridge can be an ISO drug cartridge and can store any type of therapeutic agent including any liquid drug. The drug cartridge can be coupled to a user. The first brake component 202 can be positioned adjacent to the plunger. The second brake component 204 can be positioned closer to the open end of the drug cartridge.

At 1004, the alternate step drive 200 can be in an initial operating state. As an example, the first and second brake components 202 and 204 can be expanded so as to engage the interior wall of the drug cartridge. In the initial operating state, the alternate step drive 200 can be configured to remain in a fixed position. Further, the first and second brake components 202 and 204 can be spaced apart by a maximum amount provided by the alternate step drive 200.

At 1006, the second brake component 204 can be disengaged by retracting the second brake component 204. The first brake component 202 can remain engaged with the interior wall of the drug cartridge.

At 1008, one or more wires of the alternate step drive 200 can be contracted to pull the second brake component 204 toward the first brake component 202 while compressing the compressible material 238. The second brake component 204 can be moved closer to the plunger as the first brake component 202 remains fixed.

At 1010, the second brake component 204 can be engaged with the interior wall of the drug cartridge by expanding the second brake component 204. Subsequently, the first brake component 202 can be disengaged by retracting the first brake component 202.

At 1012, the one or more wires activated to pull the second brake component 204 toward the first brake component 202 can be deactivated. As a result, with the first brake component 202 retracted, the first brake component 202 can be pushed toward the plunger by expansion of the compressible material 238. The plunger can consequently be moved forward by a predetermined amount (e.g., a predetermined amount of displacement).

The method of operation 1000 can be repeated as desired to continue to incrementally move the alternate step drive 200 and the plunger further into the drug cartridge, thereby expelling a desired amount of liquid drug from the cartridge for delivery to the user. The method of operation 1000 can represent a sequence of operations that can be implemented in sequence from any beginning initial step to provide the incremental movement of the plunger as disclosed herein.

FIGS. 11A-11B illustrate a step size 1102 of the alternate step drive 200. FIG. 11A illustrates the alternate step drive 200 prior to advancing the plunger 704 toward the first end 708 of the cartridge 702. As an example, as shown in FIG. 11A, the first brake component 202 can be in an expanded state so as to be engaged with the interior wall of the drug cartridge 702 and the compressible material 238 can be in a compressed state by the second brake component 204 being pulled toward the first brake component 202.

FIG. 11B illustrates the alternate step drive 200 after the plunger 704 has been advanced toward the first end 708 of the cartridge 702. As an example, the plunger 704 can be advanced by the first brake component 202 pushing on the plunger 704. The first brake component 202 can be pushed toward the plunger 704 when the first brake component 202 is disengaged and pushed toward the first end 708 by the compressible material 238 expanding. As shown, the plunger 704 has been advanced a distance corresponding to a step size 1102. In various embodiments, the step size 1102 can be adjusted to provide a desired amount of displacement when the alternate step drive 200 is moved.

The alternate step drive 200 can be considered to be an alternate step drive with a wire drive 200 based on the inclusion and use of one or more shape memory wires (e.g., SMA wires and/or Nitinol wires) for providing the drive mechanism for actuating the various components of the alternate step drive 200. In various embodiments, the alternate step drive 200 can be implemented using piezo actuators instead of shape memory wires (e.g., Nitinol wires).

The alternate step drive 200 is disclosed as including a controller 242 directly attached or coupled to the alternate step drive 200 (e.g., heat-staked to the second brake component 204) but is not so limited. In various embodiments, a controller for operating the alternate step drive 200 can be remote from alternate step drive 200. For example, the alternate step drive 200 can include a receiver for receiving remote communications and/or instructions (or other control or configuration information) from a remote controller. The alternate step drive 200 and the remote controller can communicate over a variety of mediums using a variety of techniques including using infrared communications, optical communications, wired communications, and/or wireless communications in accordance with any known communications protocol or standard. Additionally, the alternate step drive 200 can include a transmitter for relaying data or communications to the remote controller that may include operational data associated with the alternate step drive 200. In various embodiments, the remote controller can be located within the same drug delivery device that contains the alternate step drive 200 and corresponding drug cartridge (e.g., within the same drug delivery device attached or coupled to a user). In various embodiments, the remote controller can be located in a device that is separate from the drug delivery device that contains the alternate step drive 200 and corresponding drug cartridge (e.g., within a handheld device that is separate and apart from the drug delivery device attached or coupled to a user).

Figure 12:
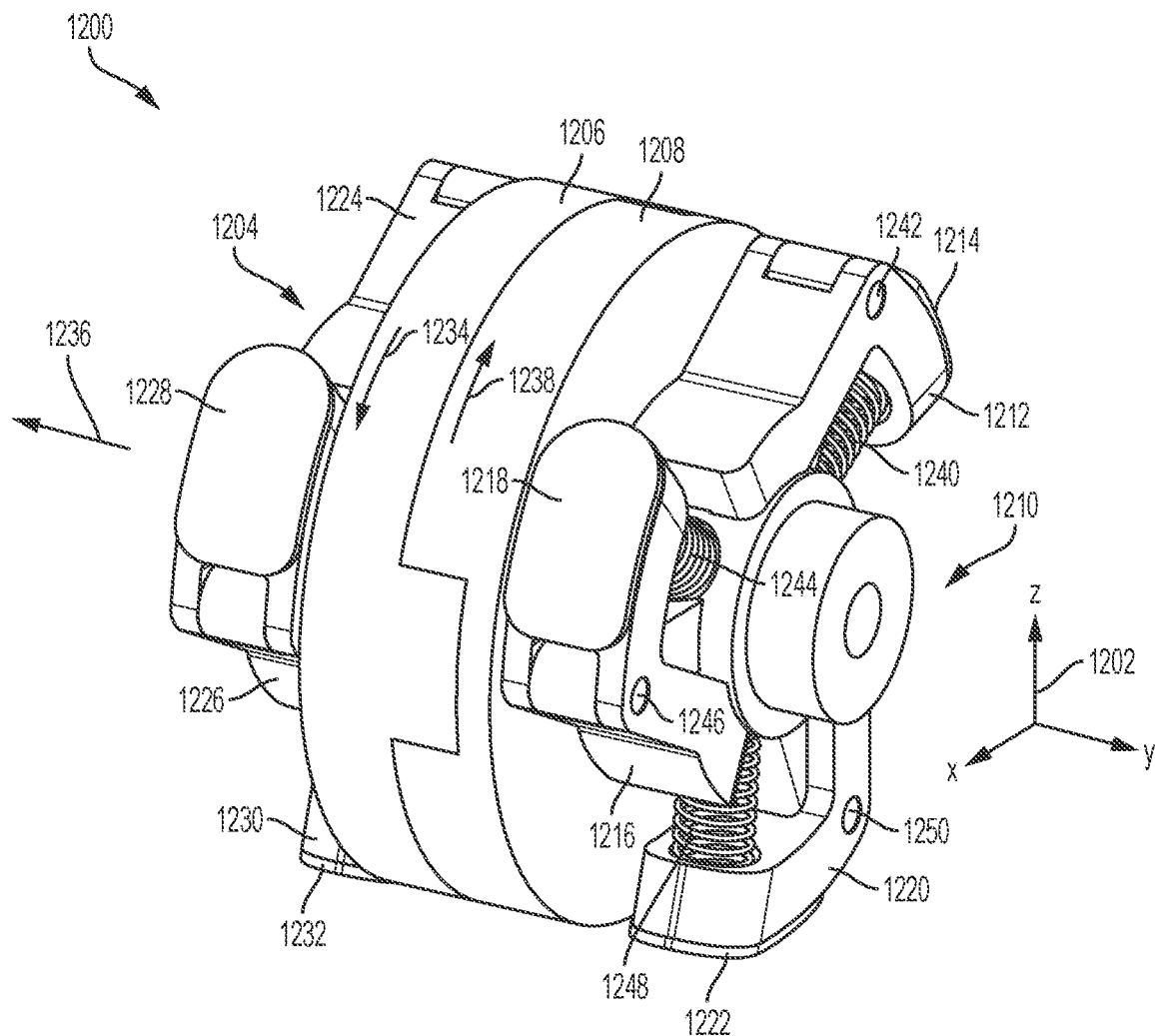
FIG. 12 illustrates a first view of a second exemplary alternate step drive.

FIG. 12 illustrates a second exemplary alternate step drive 1200. The second exemplary alternate step drive 1200 can represent an implementation of the alternate step drive 102. FIG. 12 shows a first view of the alternate step drive 1200. FIG. 12 includes a coordinate system 1202 for reference having an x-axis, a y-axis, and a z-axis, each of which is perpendicular to any other axis.

As shown in FIG. 12, the alternate step drive 1200 can include a first or front brake component 1204, a first or front cap component 1206, a second or end cap component 1208, and a second or end (or back) brake component 1210. The end brake component 1210 includes a first brake arm 1212 with a first brake pad 1214, a second brake arm 1216 with a second brake pad 1218, and a third brake arm 1220 with a third brake pad 1222. The front brake component 1204 can similarly also include three brake arms each having a brake pad—a first brake arm 1224 with a first brake pad (not shown in FIG. 12), a second brake arm 1226 with a second brake pad 1228, and a third brake arm 1230 with a third brake pad 1232. The brake pads can be formed of rubber.

The front brake component 1204 can operate as a first braking system and the end brake component 1210 can operate as a second braking system. The front and back brake components 1204 and 1210 can selectively engage and disengage an interior wall of a cartridge (e.g., an ISO drug cartridge). When the front brake component 1204 is engaged, the first, second, and third arms 1224, 1226, and 1230 can be pressed against the inner wall of the cartridge, restricting movement of the front cap component 1206 in the y-dimension. When the front brake component 1204 is disengaged, the first, second, and third arms 1224, 1226, and 1230 can be released from being pressed against the inner wall of the cartridge, allowing movement of the front cap component 1206 in the y-dimension.

Similarly, when the end brake component 1210 is engaged, the first, second, and third arms 1212, 1216, and 1220 can be pressed against the inner wall of the cartridge, restricting movement of the end cap component 1208 in the y-dimension. When the end brake component 1210 is disengaged, the first, second, and third arms 1212, 1216, and 1220 can be released from being pressed against the inner wall of the cartridge, allowing movement of the end cap component 1208 in the y-dimension.

As shown in FIG. 12, a spring 1240 can be positioned between the end cap component 1208 and the brake arm 1212. In an initial state of operation, the spring 1240 can bias the brake arm 1212 outward to press the brake pad 1214 against the inner wall of a cartridge. As further shown in FIG. 12, a brake pin 1242 can be positioned through aligned openings of the brake arm 1212 and the end cap component 1208. The brake pin 1242 can provide a point of rotation for the brake arm 1212. Specifically, in a subsequent state of operation, to disengage the brake arm 1212, the brake arm 1212 can be rotated about the brake pin 1242. In doing so, the spring 1240 is compressed and the brake pad 1214 is released from being pressed against the inner wall of the cartridge. To re-engage the brake arm 1212, the brake arm 1212 can be rotated about the brake pin 1242 as the spring 1240 provides a force to help rotate the brake arm 1212 and press the brake pad 1214 against the inner wall of the cartridge. In this manner, the brake arm 1212 can be selectively engaged and disengaged to provide a braking function.

The brake arms 1216 and 1220 can be similarly manipulated and operated based on a similar arrangement of components. As shown in FIG. 12, a spring 1244 is positioned between the end cap component 1208 and the brake arm 1216. A brake pin 1246 is positioned through aligned openings of the brake arm 1216 and the end cap component 1208. Similarly, a spring 1248 is positioned between the end cap component 1208 and the brake arm 1220. A brake pin 1250 is positioned through aligned openings of the brake arm 1220 and the end cap component 1208. This arrangement of the brake arms 1212, 1216, and 1220 enables the end braking component 1210 to be selectively activated/engaged and deactivated/disengaged to provide or not to provide a braking function, respectively, as desired. Although not depicted in FIG. 12, the front braking component 1204 can include similar components arranged and operated in a similar manner to provide the same functionality as disclosed herein for the end braking component 1210.

The front cap component 1206 and the end cap component 1208 can enclose or cover a rotational motor (not shown in FIG. 12). When the rotational motor (described further herein) rotates in a first direction 1234, the front brake component 1204 can be caused to disengage. The rotation can further cause the front cap 1206 to then move in the y-dimension in a direction 1236. As the rotation of the motor in the direction 1234 comes to a stop, the movement can lastly cause the front brake component 1204 to be re-engaged. In a subsequent stage of operation, the rotational motor can rotate in a second direction 1238 to cause the end brake component 1210 to disengage, the end cap 1208 to move in the y-dimension in the direction 1236, and then the end brake component 1210 to re-engage.

By repeating the cycle of rotating in the first direction 1234 and then the second direction 1238, the alternate step drive 1200 can be moved incrementally in the direction 1236—by first moving the front cap component 1206 forward in the direction 1236 and then moving the end cap component 1208 forward in the direction 1236. The alternate step drive 1200 can be positioned adjacent to or can be directly coupled to a plunger. The alternate step drive 1200 can be used to advance the plunger incrementally, thereby allowing the plunger to expel a liquid drug from a container in which the alternate step drive 1200 and plunger are positioned.

Figure 13:
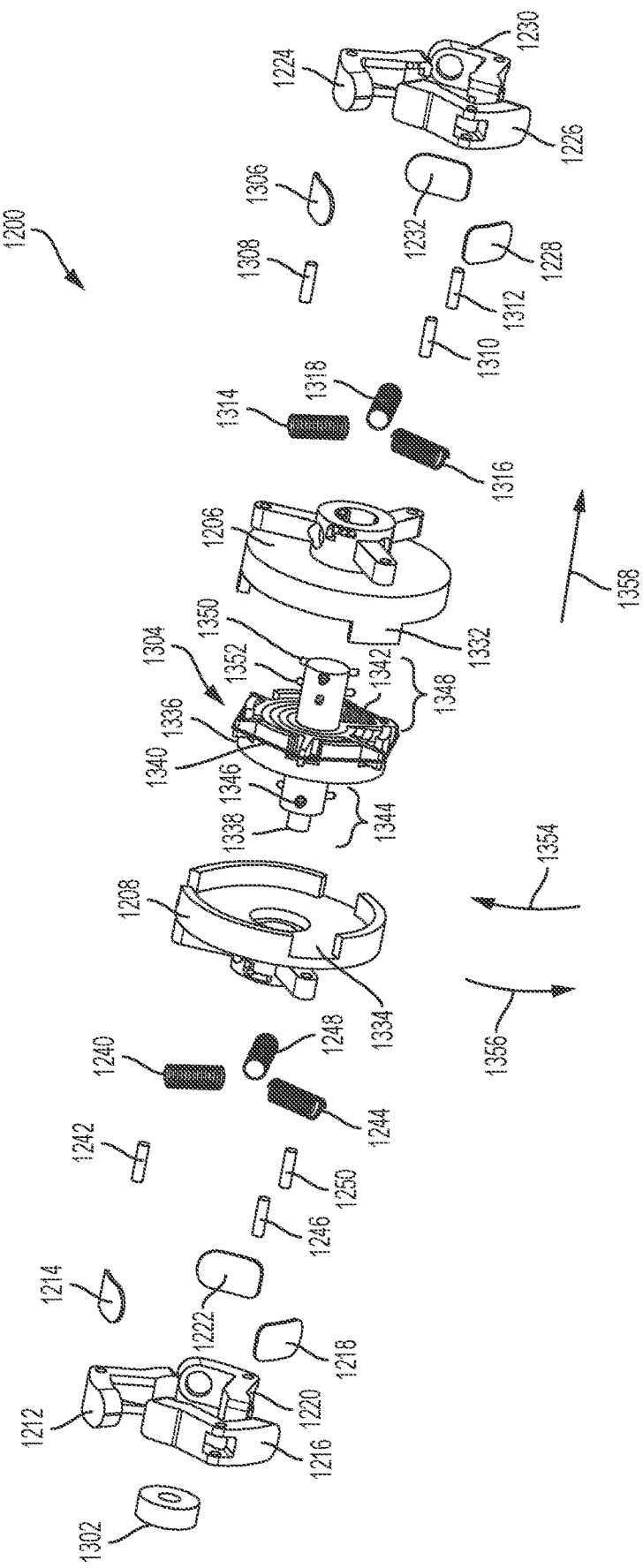
FIG. 13 illustrates an exploded view of the second exemplary alternate step drive.

FIG. 13 illustrates an exploded view of the alternate step drive 1200. As shown in the FIG. 13, the alternate step drive 1200 can include an end brake cap component 1302, the brake arms 1212, 1216, and 1220, the brake pads 1214, 1218, and 1222, the end cap component 1208, a rotational motor 1304, the front cap component 1206, the brake arms 1224, 1226, and 1230, and the brake pads 1232 and 1228. A brake pad 1306 can correspond to the brake arm 1224.

The brake arm 1224 can be coupled to the front cap component 1206 by a brake pin 1308. Similarly, the brake arms 1226 and 1230 can be coupled to the front cap component 1206 by brake pins 1310 and 1312, respectively. A spring 1314 can be positioned between the front cap component 1206 and the brake arm 1224. Similarly, springs 1316 and 1318 can be positioned between the front cap component 1206 and the brake arms 1226 and 1230, respectively.

The rotational motor 1304 can be positioned between the front cap component 1206 and the end cap component 1208. The front cap component 1206 can include one or more extensions 1332. The end cap component 1208 can include one or more openings 1334. The corresponding extensions 1332 and openings 1334 can be fitted together to form an interlock, preventing the front cap component 1206 and the end cap component 1208 from rotating separately while allowing each to move independently in the y-dimension.

The rotational motor 1304 can include a main body 1336 and a central shaft 1338. A wire 1340 can be wrapped around a periphery of the main body 1336 and can be coupled to a spring 1342. The wire 1340 can be a shape memory wire such as, for example, a Nitinol wire (or SMA wire). A first portion 1344 of the central shaft 1338 can be positioned through an opening of the end cap component 1208 and can engage or be coupled to the end brake cap component 1302. A first set of pins 1346 can be positioned on the first portion 1344 of the central shaft 1338 and can engage the brake arms 1212, 1216, and 1220. The number of pins within the first set of pins 1346 can match the number of brake arms 1212, 1216, and 1220 such that each brake arm 1212, 1216, and 1220 is paired with a single, specific pin from the first set of pins 1346.

A second portion 1348 of the central shaft 1338 can be positioned through an opening of the front cap component 1206. A first set of pins 1350 can be positioned on the second portion 1348 of the central shaft 1338 and can engage the brake arms 1224, 1226, and 1230. The number of pins within the first set of pins 1350 can match the number of brake arms 1224, 1226, and 1230 such that each brake arm 1224, 1226, and 1230 is paired with a single, specific pin from the first set of pins 1350.

When a current is applied to the Nitinol wire 1340, the Nitinol wire 1340 can contract, thereby causing the central shaft 1338 to rotate in a first direction 1354 (corresponding to the direction 1234 of FIG. 12). When the central shaft 1338 is rotated in the direction 1354, the first set of pins 1350 can engage the brake arms 1224, 1226, and 1230. Specifically, the first set of pins 1350 can cause the brake arms 1224, 1226, and 1230 to rotate about the brake pins 1308, 1310, and 1312, respectively. As a result, the brake arms 1224, 1226, 1230 can be disengaged from an inner wall of a cartridge as the springs 1314, 1316, and 1318 are compressed. Further, a second set of pins 1352 can engage the front cap component 1206 to cause it to move in a direction 1358 (along with the brake arms 1224, 1226, and 1230).

When the current is removed from the Nitinol wire 1340, the Nitinol wire 1340 can expand or relax and the spring 1342 can pull on the Nitinol wire 1340 causing the central shaft 1338 to rotate in a second direction 1356 (corresponding to the direction 1238 of FIG. 12). When the central shaft 1338 is rotated in the direction 1356, the first set of pins 1346 can engage the brake arms 1212, 1216, and 1220. Specifically, the first set of pins 1346 can cause the brake arms 1212, 1216, and 1220 to rotate about the pins 1242, 1246, and 1250, respectively. As a result, the brake arms 1212, 1216, and 1220 can be disengaged from an inner wall of a cartridge as the springs 1240, 1244, and 1244 are compressed. Further, the second set of pins 1352 can engage the end cap component 1208 to cause the end cap component 1208 to move in the direction 1358 (along with the brake arms 1212, 1216, and 1220).

By alternating the application and the removal of a current to the Nitinol wire 1340, the alternate step drive 1200 can be caused to incrementally move in the direction 1358. In various embodiments, when the Nitinol wire 1340 is activated, the front cap component 1206 can be advanced in the direction 1358 and separated from the end cap component 1208. When the Nitinol wire 1340 is deactivated, the end cap component 1208 can be advanced in the direction 1358, thereby closing any gap between the front and end cap components 1206 and 1208. Accordingly, when coupled to a plunger positioned within a drug cartridge, the alternate step drive 1200 can incrementally move the plunger in the direction 1358 to expel a portion of a stored liquid drug from the cartridge.

In various embodiments, during a first stage of operation, when the central shaft 1338 is rotated in the first direction 1354, the first set of pins 1350 ensure the front brake arms 1224, 1226, and 1230 are disengaged. During the movement in the first direction 1354, the front cap component 1206 is caused to be moved in the direction 1358. As a result, the front and end cap components 1206 and 1208 are displaced by a predetermined amount. At the end of the movement in the first direction 1354, the front brake arms 1224, 1226, and 1230 are re-engaged.

During a second stage of operation, when the central shaft 1338 is rotated in the second direction 1356, the first set of pins 1346 ensure the end brake arms 1212, 1216, and 1220 are disengaged. Further, during the movement in the second direction 1356, the end cap component 1208 is caused to be moved in the direction 1358. The gap between the end cap component 1208 and the front cap component 1206 is removed or closed. At the end of the movement in the second direction 1356, the end brake arms 1212, 1216, and 1220 are re-engaged.

The front brake arms 1224, 1226, and 1230 can be cammed or shaped to engage with the first set of pins 1350 in a manner that disengages the front brake arms 1224, 1226, and 1230 when the central shaft 1338 is moved in the first direction 1354 while ensuring the front brake arms 1224, 1226, and 1230 remain engaged when the central shaft 1338 is moved in the second direction 1356. Similarly, the end brake arms 1212, 1216, and 1220 can be cammed or shaped to engage with the first set of pins 1346 in a manner that disengages the end brake arms 1212, 1216, and 1220 when the central shaft 1338 is moved in the second direction 1356 while ensuring the end brake arms 1212, 1216, and 1220 remain engaged when the central shaft 1338 is moved in the first direction 1354.

Figure 14:
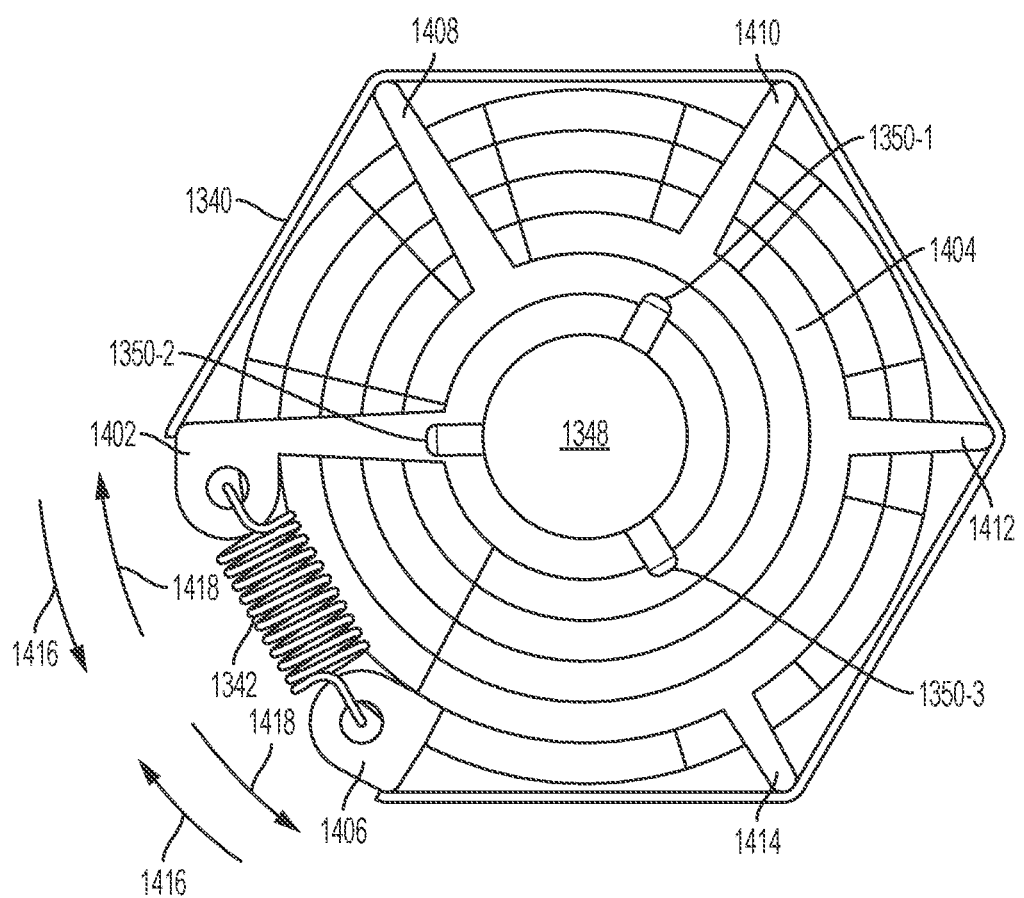
FIG. 14 illustrates a portion of a rotational motor of the second exemplary alternate step drive.

FIG. 14 illustrates a front view of a portion of the rotational motor 1304. In particular, FIG. 14 shows an exemplary routing and arrangement of the wire 1340. As shown, the spring 1342 is coupled to a first extension component 1402 of a base component 1404 and is also coupled to a second extension component 1406 of the base component 1404. The wire 1340 is also coupled to the first and second extension components 1402 and 1406. The wire 1340 is wrapped around additional extension components 1408, 1410, 1412, and 1414. As further shown in FIG. 14, the second portion 1348 of the central shaft 1338 extends from a center of the base component 1404. The individual pins 1350-1, 1350-2, and 1350-3 of the first set of pins 1350 are shown projecting from the second portion 1348 of the central shaft 1338. Any number of extension components can be used. In various embodiments, the extension components can be equally spaced around a perimeter of the rotational motor 1304.

When a current is applied to the Nitinol wire 1340, the Nitinol wire 1340 can contract, thereby causing the first and second extension components 1402 and 1406 to be pulled apart and thereby rotate relative to one another as shown by indicators 1418. When the current is removed from the Nitinol wire 1340, the Nitinol wire 1340 can relax. As a result, the spring 1342 can pull the first and second extension components 1402 and 1406 back together as shown by indicators 1416. FIG. 14 illustrates the arrangement of the components of the rotational motor 1304 when the wire 1340 is not activated (e.g., when a current is not being applied to the wire 1340).

Figure 15:
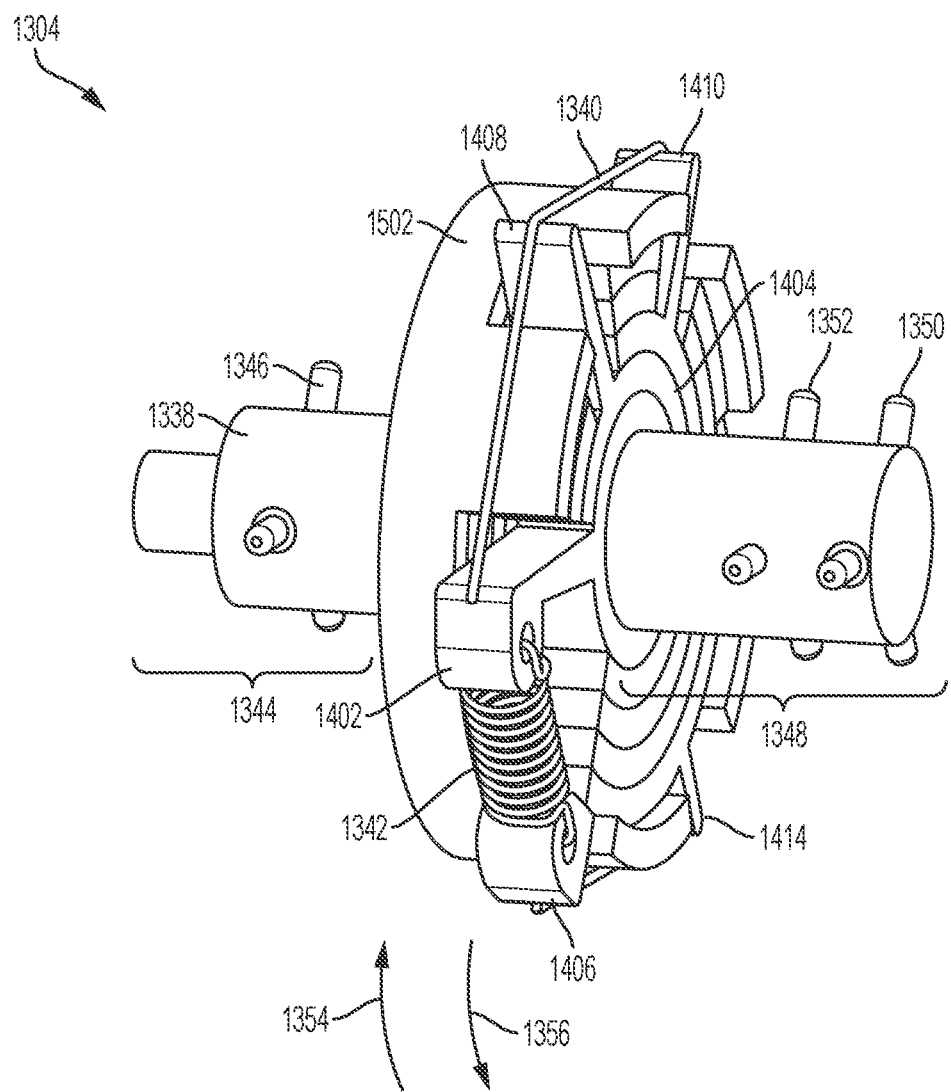
FIG. 15 illustrates the rotational motor of the second exemplary alternate step drive.

FIG. 15 illustrates a partial side view of the rotational motor 1304. As shown, the base component 1404 is surrounded or covered by a cover component 1502. The cover component 1502 includes openings for each of the extension components 1402, 1406, 1408, 1410, 1412 (not shown in FIG. 15), and 1414. The central shaft component 1338 is shown positioned through a center of the base component 1404, with the base component 1404 coupled to each of the extension components 1402, 1406, 1408, 1410, 1412, and 1414.

As disclosed herein, when the wire 1340 contracts, the central shaft component 1338 can rotate in the direction 1354. As a result, the pins 1346, 1350, and 1352 all rotate in the direction 1354. The amount of rotation can be any amount including, for example, approximately 20 degrees. When the wire 1340 is released from being contracted, the central shaft component 1338 can be rotated back in the direction 1356 to its initial position (e.g., as shown in FIG. 15). The pins 1346, 1350, and 1352 can also all rotate in the direction 1356.

Figure 16:
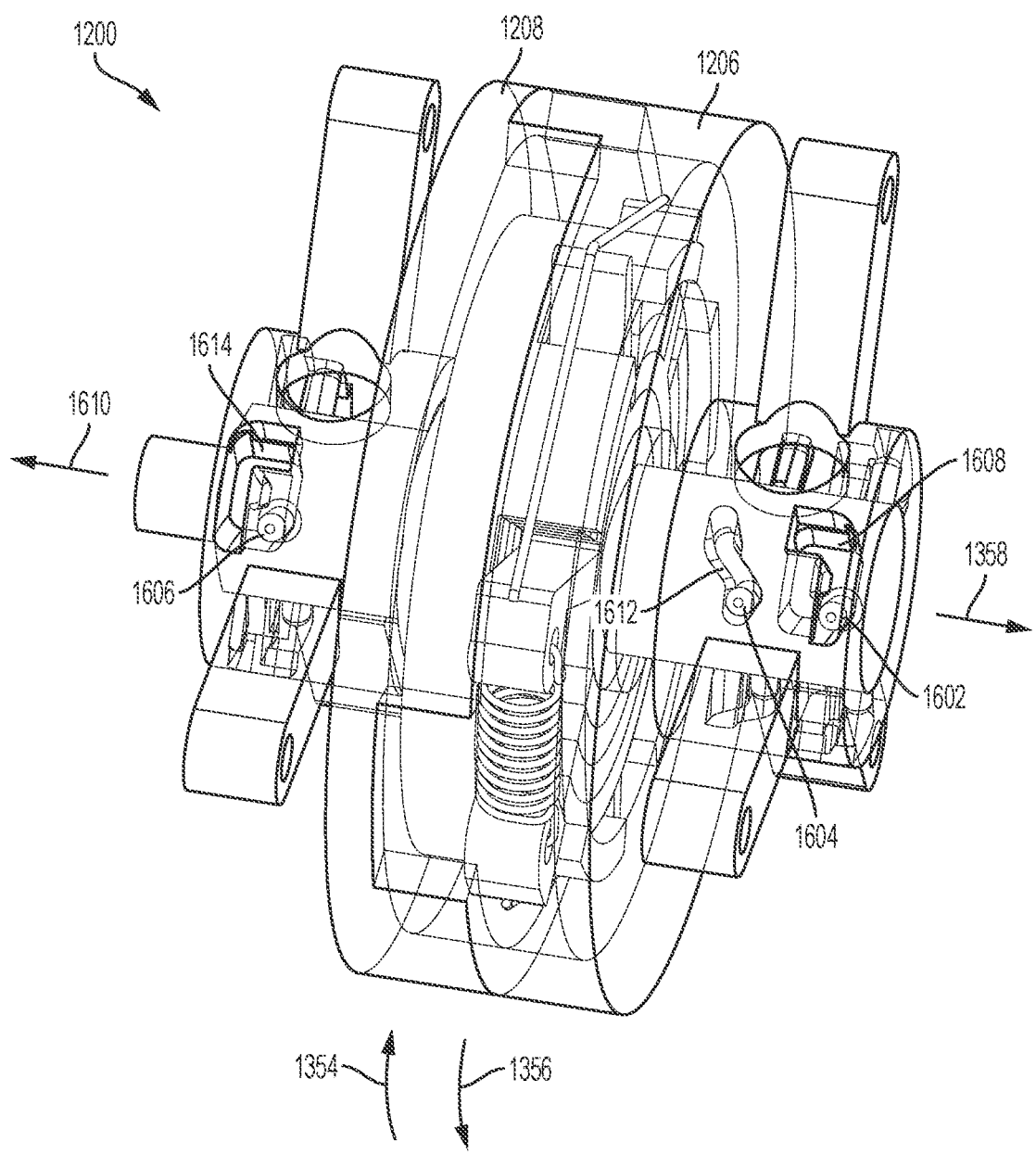
FIG. 16 illustrates a portion of the second exemplary alternate step drive.

FIG. 16 illustrates a portion of the alternate step drive 1200. Specifically, FIG. 16 illustrates a partial side view of the alternate step drive 1200 with the front and end caps 1206 and 1208 shown in phantom and the front and back brake components 1204 and 1210 not shown to reveal an exemplary arrangement of internal components of the alternate step drive 1200. FIG. 16 shows an exemplary arrangement and coupling between the central shaft component 1338 and the end cap component 1208 and the front cap component 1206.

Pin 1602 can represent a pin from the set of pins 1350. Pin 1604 can represent a pin from the set of pins 1352. Pin 1606 can represent a pin from the set of pins 1346. The pin 1602 can be positioned within a slot area 1608. The slot area 1608 can be an opening or channel for guiding movement of the pin 1602 as the central shaft component 1338 is rotated. The slot area 1608 can be formed on or as part of an internal portion of the front cap component 1206. The slot area 1608 can be shaped and arranged to allow the pin 1602 to engage a front brake arm (e.g., the brake arm 1226) when the central shaft 1338 is rotated in the direction 1354. Specifically, when the central shaft 1338 is rotated in the direction 1354, the slot area 1608 allows the pin 1602 to engage the front brake arm as it also moves in the direction 1354 and then in the direction 1610. During this time, the pin 1602 initially causes the corresponding front brake arm to be disengaged and then re-engaged at the end of the rotation of the central shaft component 1338 in the direction 1354 (e.g., when the pin 1602 has moved in the direction 1610 as allowed by the slot area 1608). Accordingly, movement of the central shaft 1338 in the direction 1354 causes the pin 1602 to be moved in the slot area 1608 which is shaped to allow the pin 1602 to disengage and then re-engage a corresponding front brake arm.

The slot area 1608 can be a cammed region or shaped internal region of the front cap component 1206. Each of the other pins in the set of pins 1350 can be positioned in similarly shaped slot areas to similarly disengage and then re-engage corresponding brake arms when the central shaft 1338 is rotated in the direction 1354.

Pin 1604 can be positioned within a slot area 1612. Slot area 1612 can also be a cammed region or shaped internal region of the front cap component 1206. The slot area 1612 can have an s-shape or bent slotted shape. When the central shaft 1338 is rotated in the direction 1354, the pin 1604 moves in the direction 1354 within the slot area 1612. The movement of the pin 1604 within the slot area 1612 causes the front cap component 1206 to move in the direction 1358 as the pin 1604 is rotated in the direction 1354 (as the front brakes are disengaged). Each of the other pins in the set of pins 1352 can be positioned in similarly shaped slot areas to similarly contribute to advancing the front cap component 1206 in the direction 1358 when the central shaft 1338 is rotated in the direction 1354.

The slot area 1608 can be further shaped to prevent or block the pin 1602 from engaging the corresponding brake arm when the central shaft 1338 is rotated in the direction 1356. Accordingly, when the central shaft 1338 is rotated in the direction 1356, the pin 1602 can be prevented from releasing the corresponding brake. Each of the other pins in the set of pins 1350 can be similarly manipulated by similarly shaped corresponding slot areas, such that the front brake component 1204 remains engaged when the central shaft is rotated back in the direction 1356.

Pin 1606 can be positioned in slot area 1614. Slot area 1614 can be shaped and arranged to prevent the pin 1606 from engaging a corresponding back brake arm (e.g., back brake arm 1216) as the central shaft component is rotated in the direction 1354. However, the slot area 1614 can allow the pin 1606 to engage the corresponding back brake arm as the central shaft 1338 is rotated in the direction 1356. In this way, the slot areas 1608 and 1614 can be inverses of one another such that pin 1606 causes an end brake arm to be disengaged and then re-engaged as the central shaft 1338 is rotated in the direction 1356 as the slot area 1608 prevents the pin 1602 from disengaging a corresponding front brake arm.

The slot area 1614 can be a cammed region or shaped internal region of the end cap component 1208. Each of the other pins in the set of pins 1346 can be positioned in similarly shaped slot areas to similarly disengage and then re-engage corresponding brake arms when the central shaft 1338 is rotated in the direction 1356. Further, these slot areas can prevent the pins 1346 from engaging the corresponding brake arms when the central shaft is rotated in the direction 1354.

In this way, the front brake component 1204 is disengaged when the central shaft is rotated in the direction 1354 (and then re-engaged at the completion of this rotation) while the end brake component 1210 remains engaged. Correspondingly, the end brake component 1210 is disengaged when the central shaft is rotated in the direction 1356 (and then re-engaged at the completion of this rotation) while the front brake component 1204 remains engaged. When the end brake component 1210 is disengaged, the pin 1604 rotates down the slot area 1612 in the direction 1356. The movement of the pin 1604 causes the end cap component 1208 to be advanced in the direction 1358. As a result, the entire step drive 1200 is incrementally advanced in the direction 1358.

Figure 17B:
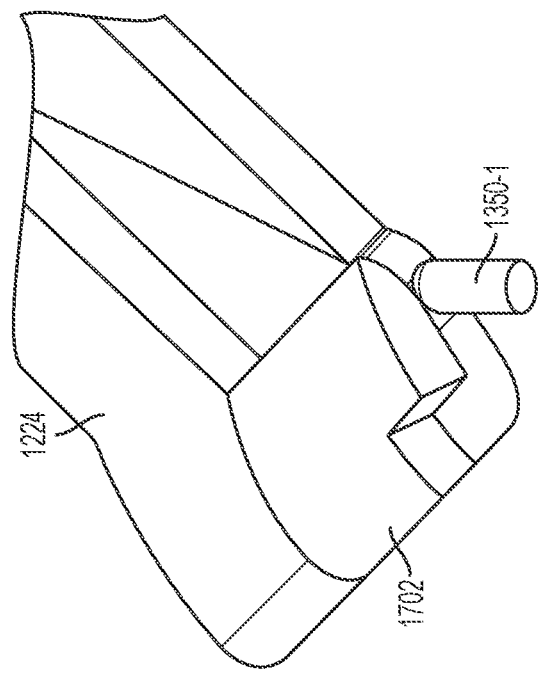
FIG. 17B illustrates a second view of the brake arm of the second exemplary alternate step drive.
Figure 17A:
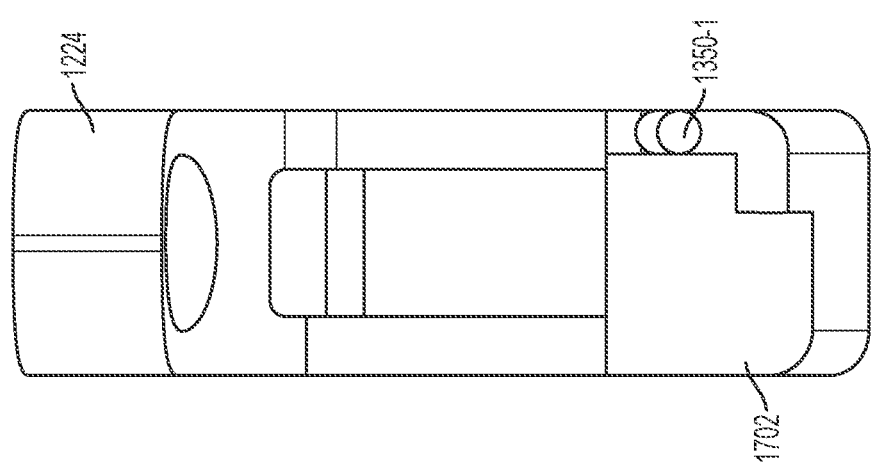
FIG. 17A illustrates a first view of a brake arm of the second exemplary alternate step drive.

FIGS. 17A-17B illustrate an exemplary arrangement of a brake arm (e.g., the brake arm 1224) relative to a pin (e.g., the pin 1350-1) for engaging and disengaging the brake arm. A first view of the brake arm 1224 is shown in FIG. 17A and FIG. 17B shows a second view of the brake arm 1224. The pin 1350-1 is shown as making contact in proximity to a bottom portion of the brake arm 1224. The bottom portion of the brake arm 1224 can be shaped (e.g., using a combination of proud portions and cutout portions) such that the pin 1350-1 engages the brake arm 1224 during a first desired portion of the rotational stroke of the rotational motor 1304—to release the brake arm 1224 from pressing against an inner wall of a cartridge—and disengages the brake arm 1224 during a second desired portion of the rotational stroke of the rotational motor 1304—to allow the brake arm 1224 to move and be pressed against the inner wall of the cartridge. FIG. 17A shows a proud portion 1702 of the brake arm 1224 that can restrict the ability of the pin 1350-1 to engage the brake arm 1224. FIG. 17B shows a close-up side view of the brake arm of FIG. 17A. As shown in FIG. 17B, the proud portion 1702 is shown relative to the pin 1350-1.

Figure 18:
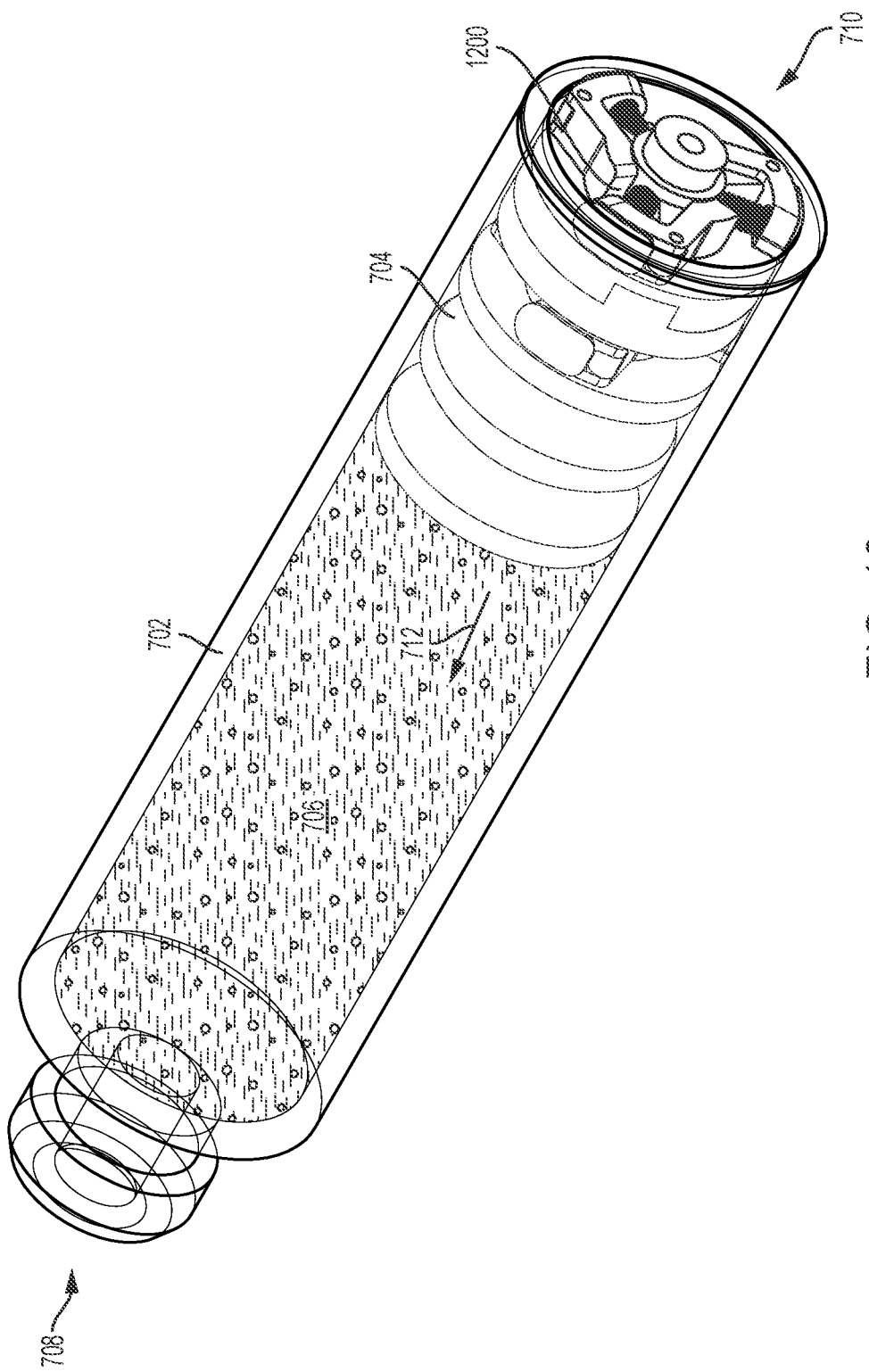
FIG. 18 illustrates a first view of the second exemplary alternate step drive within a container.

FIG. 18 illustrates the alternate step drive 1200 within the container 702. As shown in FIG. 18, the alternate step drive 1200 can be positioned adjacent to the plunger 704. In various embodiments, the alternate step drive 1200 can be directly coupled or connected to the plunger 704. The alternate step drive 1200 can be positioned within the container 702 through the open end 710 of the container 702. As disclosed herein, the alternate step drive 1200 can be used to drive the plunger 704 toward the first end 708 of the container 702. The alternate step drive 1200 can be coupled to the plunger 704 such that a force applied in the direction 712 by the alternate step drive 200 can cause the plunger 704 to move incrementally in the direction 712.

Figure 19:
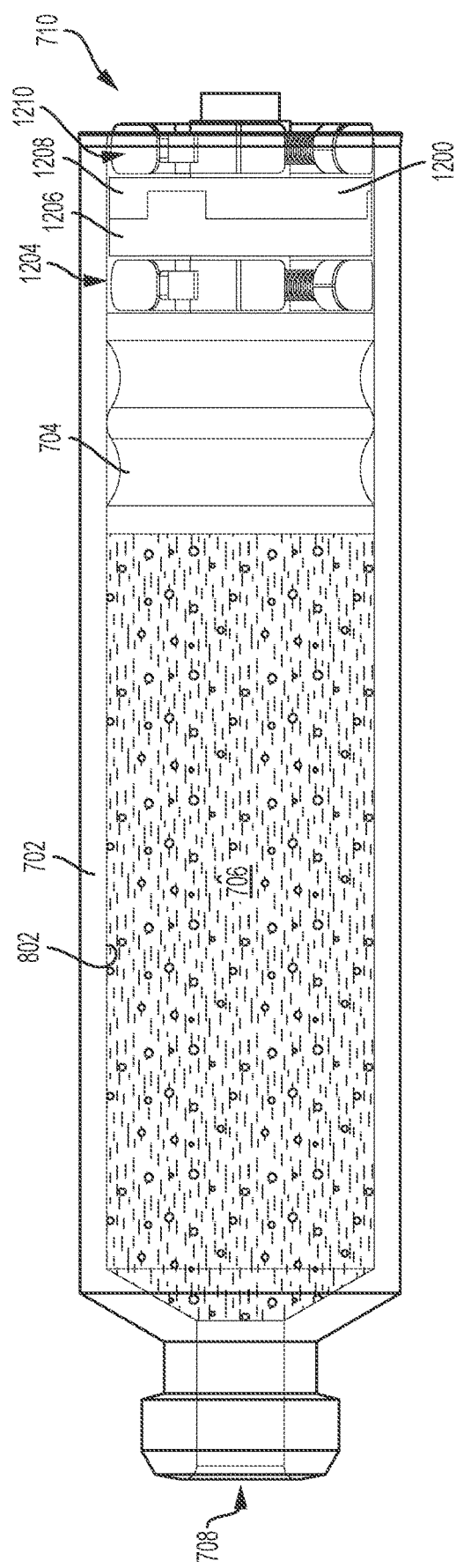
FIG. 19 illustrates a second view of the second exemplary alternate step drive within the container.

FIG. 19 illustrates a side view of the alternate step drive 1200 within the container 702. As shown, the plunger 704 can be positioned adjacent to an end of the alternate step drive 2100—for example, adjacent to the front brake component 1204. The interior wall 802 can be engaged and/or disengaged by the front and back brake components 1204 and 1210. As shown in FIG. 19, the front and back brake components 1204 and 1210 are pressed against the interior wall 802 of the container 702 to prevent movement of the alternate step drive 1200.

Figure 20:
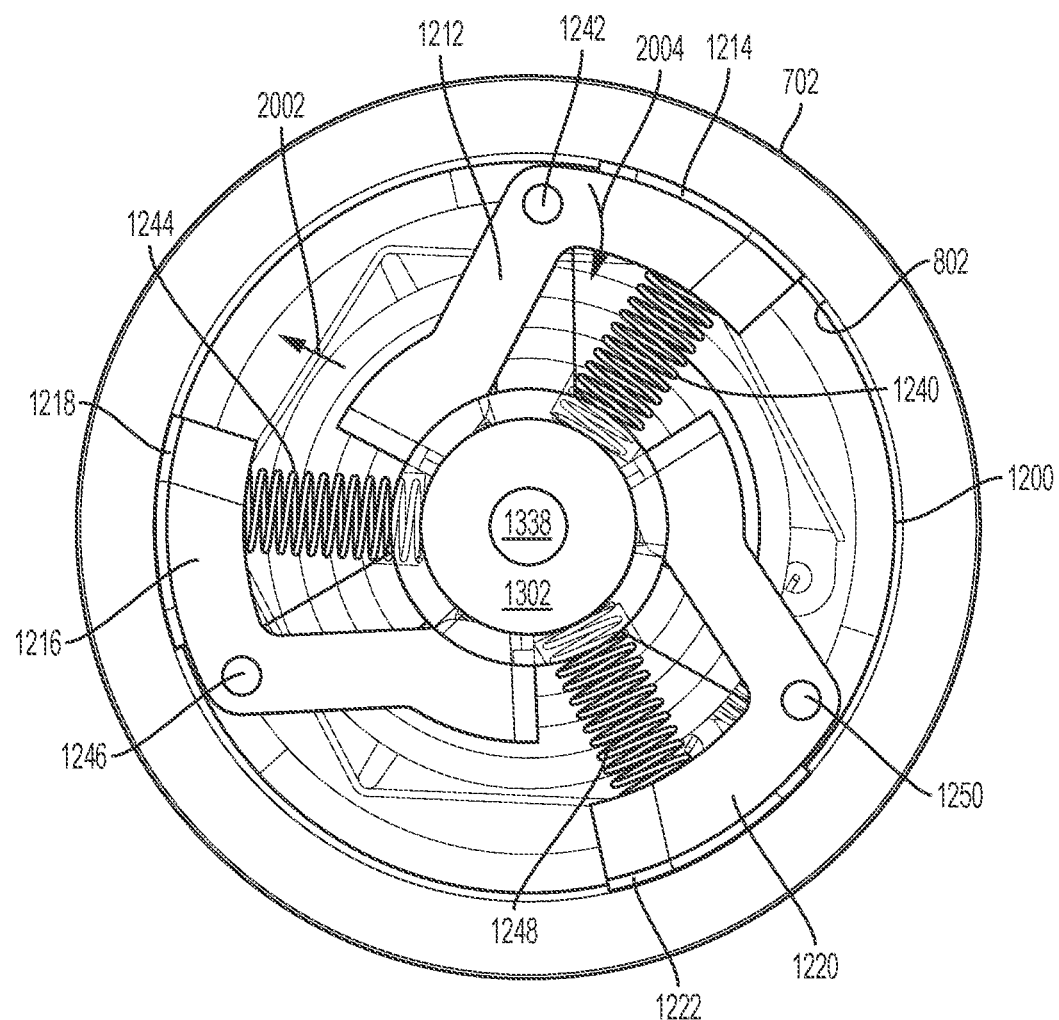
FIG. 20 illustrates a third view of the second exemplary alternate step drive within the container.

FIG. 20 illustrates a rear view of the alternate step drive 1200 within the container 702. As shown, each of the brake arms 1212, 1216, and 1220 are engaged and pressed against the inner wall 802 of the cartridge 702. As an example, the spring 1240 is extended and presses the brake pad 1214 of the brake arm 1212 against the inner wall 802. In various embodiments, the spring 1240 can bias the brake arm 1212 against the inner wall 802. To release the brake arm 1212, an end of the brake arm 1212 can be pushed in a direction 2002. The brake arm 1212 can be pushed in the direction 2002 by one of the pins in the set 1350, based on the allowed movement of the pins 1350 as disclosed in relation to FIGS. 16, 17A, and 17B. In doing so, the brake arm 1212 can rotate about the brake pin 1242 in a direction 2004, thereby pulling the brake pad 1214 off of the inner wall 802. Once the brake pad 1214 is substantially pulled off from the inner wall 802, the brake arm 1212 will no longer restrict movement of the end cap component 1208. The other brake arms 1216 and 1220 can be similarly controlled and manipulated to selectively engage and disengage the inner wall 802.

Figure 21:
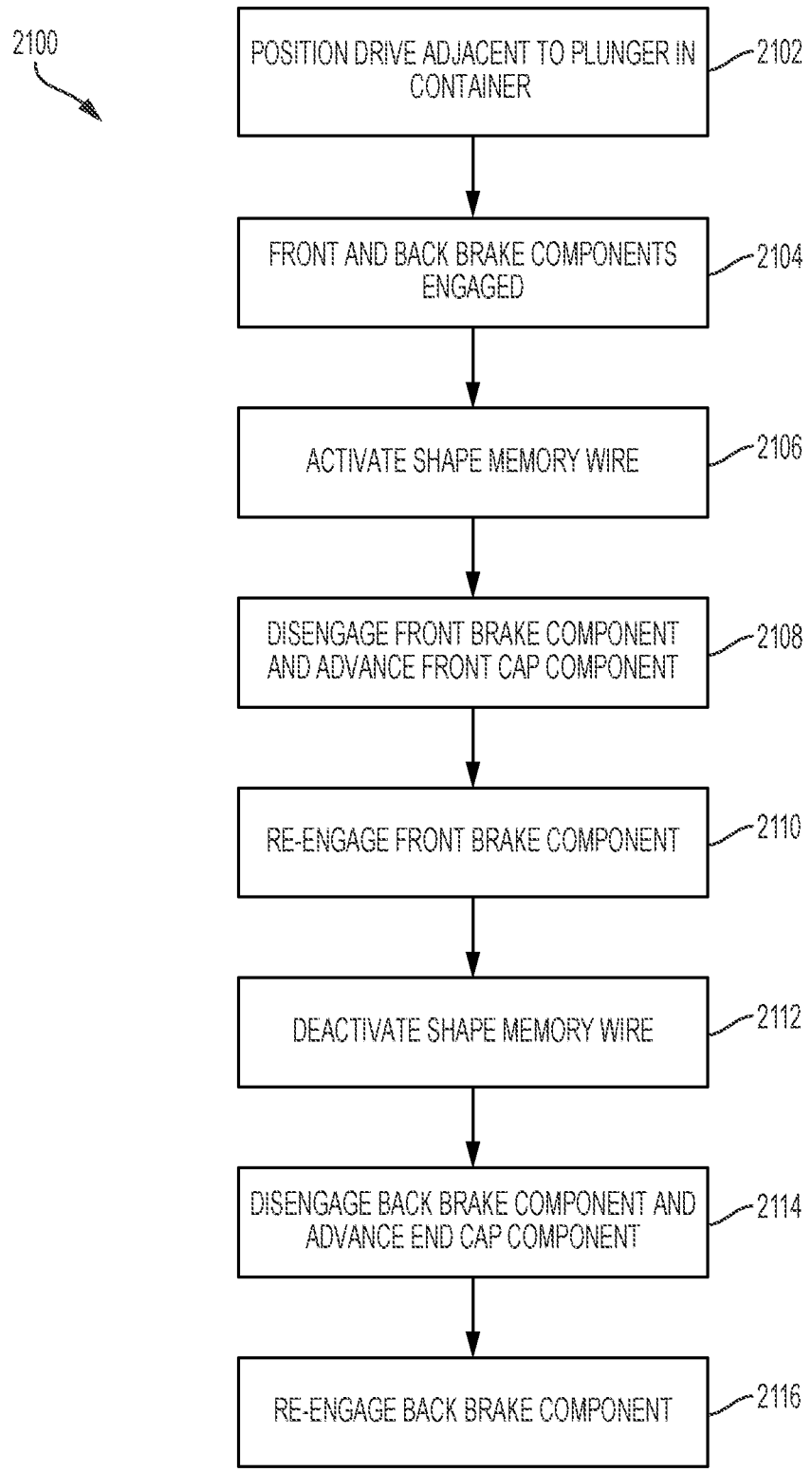
FIG. 21 illustrates an exemplary method of operation for the second exemplary alternate step drive.

FIG. 21 illustrates an exemplary method of operation 2100 for the alternate step drive 1200. At 2102, the alternate step drive 1200 can be positioned adjacent to a plunger within a drug cartridge holding a liquid drug. In various embodiments, the alternate step drive 1200 can be directly coupled or connected to the plunger. The alternate step drive 1200 can be positioned within an open end of the drug cartridge. The drug cartridge can be an ISO drug cartridge and can store any type of therapeutic agent including any liquid drug. The drug cartridge can be coupled to a user. The front brake component 1204 can be positioned adjacent to the plunger. The end brake component 1210 can be positioned closer to the open end of the drug cartridge.

At 2104, the alternate step drive 1200 can be in an initial operating state. As an example, the front and end brake components 1204 and 1210 can be engaged with the interior wall of the drug cartridge. In the initial operating state, the alternate step drive 1200 can be configured to remain in a fixed position.

At 2106, the Nitinol wire 1340 can be activated. The Nitinol wire 1340 can be activated by applying a current to the Nitinol wire 1340. When activated, the Nitinol wire 1340 can contract.

At 2108, the central shaft 1338 of the alternate step drive 1200 can be rotated in a first direction in response to the Nitinol wire 1340 being activated. As the central shaft component 1338 is being rotated in the first direction, the front brake component 1204 can be disengaged from the inner wall of the drug cartridge. Further, the front cap component 1206 (and the front brake component 1204) can be moved forward toward the plunger by an incremental distance. The movement of the front cap component 1206 can drive the plunger forward to expel a portion of a stored liquid drug from the drug container.

At 2110, the rotation of the central shaft component 1338 of the alternate step drive 1200 in the first direction can come to a halt. The front brake component 1204 can re-engage the inner wall of the drug container at approximately the same time rotation in the first direction is ended.

At 2112, the Nitinol wire 1340 can be deactivated. The Nitinol wire can be deactivated by removing application of a current to the Nitinol wire 1340. When deactivated, the Nitinol wire 1340 can relax.

At 2114, the central shaft 1338 of the alternate step drive 1200 can be rotated in a second, opposite direction in response to the Nitinol wire 1340 being deactivated. As the central shaft component 1338 is being rotated in the second direction, the end brake component 1210 can be disengaged from the inner wall of the drug cartridge. Further, the end cap component 1208 (and the end brake component 1210) can be moved forward toward the plunger by an incremental distance. Specifically, the end cap component 1208 can be moved toward the front cap component 1206 to be positioned adjacent to the front cap component 1206.

At 2116, the rotation of the central shaft component 1338 of the alternate step drive 1200 in the second direction can come to a halt. The end brake component 1210 can re-engage the inner wall of the drug container at approximately the same time rotation in the second direction is ended.

At 2108, the front cap component 1206 can be separated from the end cap component 1208 by a predetermined amount (e.g., forming a gap in the same direction of the movement of the front cap component 1206). At 2114, the movement of the end cap component 1208 as the front cap component 1206 is held fixed can close any gap between the front and end cap components 1206 and 1208. In this way, a back portion of the alternate step drive 1200 advances to re-engage a front portion of the alternate step drive 1200.

The method of operation 2100 can be repeated as desired to continue to incrementally move the alternate step drive 1200 and the plunger further into the drug cartridge, thereby expelling a desired amount of liquid drug from the cartridge for delivery to the user. The method of operation 1200 can represent a sequence of operations that can be implemented in sequence from any beginning initial step to provide the incremental movement of the plunger as disclosed herein.

Figure 22:
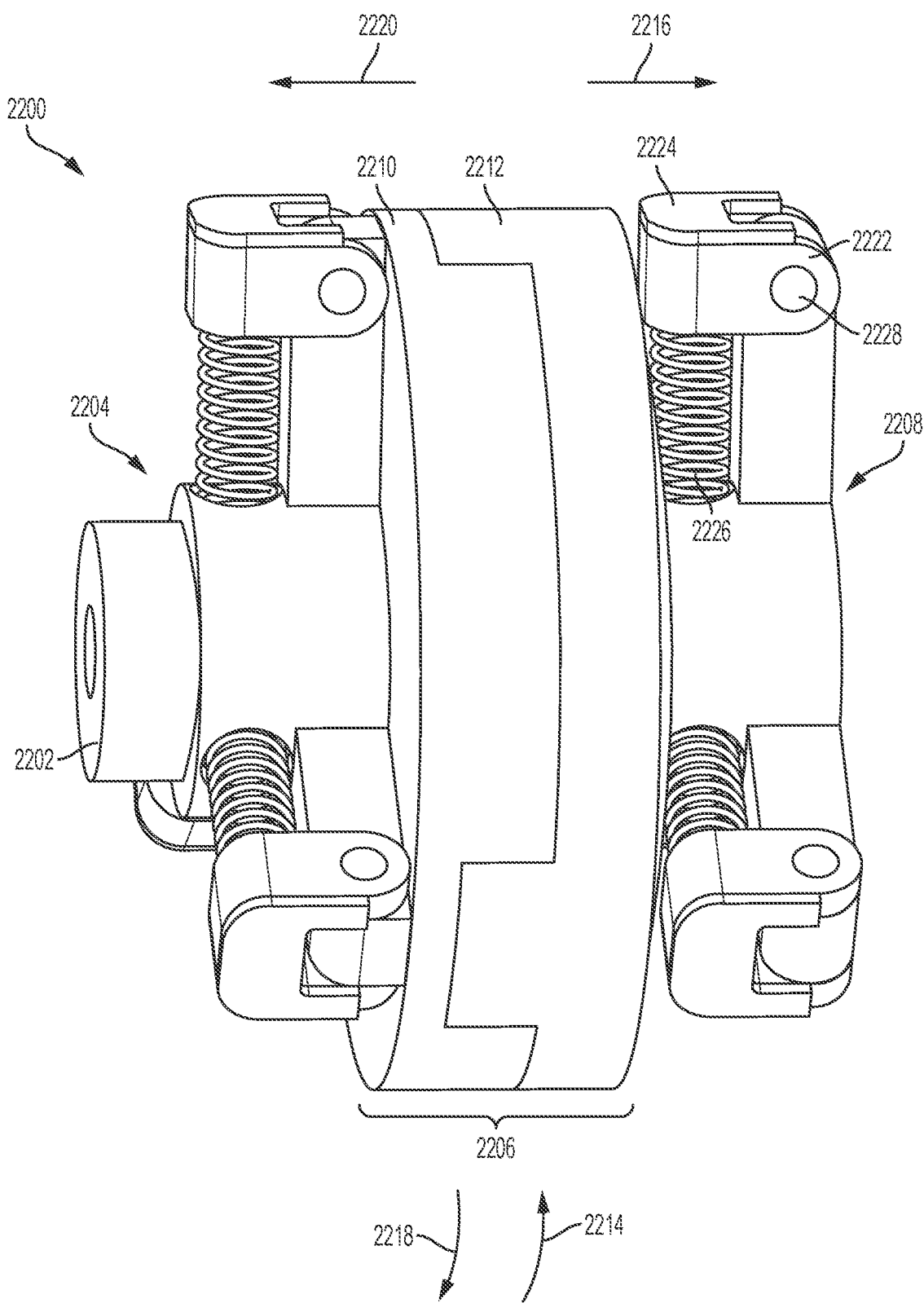
FIG. 22 illustrates a third exemplary alternate step drive.

FIG. 22 illustrates a third exemplary alternate step drive 2200. The alternate step drive 2200 can be a variation of the alternate step drive 1200 and can include many of the same or similar features, components, and functionality of the alternate step drive 1200. The alternate step drive 2200 can be operated in a similar manner as the alternate step drive 1200 to expel a portion of a stored liquid drug from a container.

As shown in FIG. 22, the alternate step drive 2200 can include an end brake cap 2202, a first or end brake component 2204, a body or center component 2206, and a second or front brake component 2208. The center component 2206 can include a first or end cap component 2210 and a second or a front cap component 2212. The end cap component 2210 can substantially correspond to the end cap component 1208. The front cap component 2210 can substantially correspond to the front cap component 1206. Overall, the end cap component 2210 and the front cap component 2212 can include substantially the same features and can be operated in a substantially similar manner as the end cap component 1208 and the front cap component 1206, respectively.

The center component 2206 can house a rotational motor (not shown in FIG. 22) that can operate and include features substantially the same as the rotational motor 1304. For example, an internal portion of the rotational motor can rotate a portion of the alternate step drive 2200 in a first direction 2214 to incrementally move the front cap component 2212 in a direction 2216. When the internal portion of the rotational motor rotates the portion of the alternate step drive 2200 in a second direction 2218, the end cap component 2210 can be incrementally moved in the direction 2216. In this manner, the alternate step drive 2200 can be operated and include features substantially the same as the alternate step drive 1200.

The end brake component 2204 and the front brake component 2208 can each be self-energizing brakes. Specifically, the end brake component 2204 and the front brake component 2208 can prevent or restrict movement of the alternate step drive 2200 in a direction 2220 independently—for example, without further input or control from any other component of the alternate step drive 2200. In various embodiments, the end brake component 2204 and the front brake component 2208 can be arranged to allow movement in the direction 2216 while restricting movement in the direction 2220.

As shown in FIG. 22, the front brake component 2208 can include a brake arm 2222 having a brake pad 2224. The brake arm 2222 can be biased to make contact with an inner wall of a drug cartridge by a spring 2226. The brake arm 2222 can be coupled to the front cap component 2212 by a brake pin 2228. The front brake component 2208 can include any number of brake arms arranged in a similar manner. In an embodiment, the front brake component 2208 can include three brake arms.

The arrangement of the brake arm 2222 can allow the front brake component 2208 to move in the direction 2216—for example, by the front cap component 2212. However, movement in the direction 2220 can be restricted. This functionality can be provided based on the arrangement of the brake arm 2222 components and does not require engagement of pins with the brake arms of the front brake component 2208 as is used with the alternate step drive 1200. The end brake component 2204 can also include any number of brake arms similarly arranged.

The alternate step drive 2200 can be coupled to a plunger in a manner similarly to that described in relation to the alternate step drive 1200. Accordingly, the alternate step drive 2200 can be operated to drive a plunger in the direction 2216 to expel a liquid drug from a drug cartridge in which the plunger and alternate step drive 2200 are positioned. Accordingly, the alternate step drive 2200 can provide similar functionality as the alternate step drive 1200 with a different braking system that includes fewer components and reduced operational complexity.

The alternate step drive 1200 can be considered to be an alternate step drive with a wire rotation drive 1200. The alternate step drive 2200 can be considered to be an alternate step drive with a wire rotation drive and self-energizing brakes 2200. In various embodiments, the alternate step drive 1200 and/or the alternate step drive 2200 can be implemented using a rotational motor and can include any number of brake arms.

In various embodiments, the alternate step drive 1200 and the alternate step drive 2220 can include a controller directly attached or coupled to the devices. In various embodiments, a controller for operating the alternate step drive 1200 or the alternate step drive 2200 can be remote from the devices. As described in relation to the alternate step drive 200, the alternate step drive 1200 and the alternate step drive 2200 can facilitate bidirectional communications with the remote controller over a variety of mediums using a variety of techniques including infrared communications, optical communications, wired communications, or wireless communications in accordance with any known communications protocol or standard. In various embodiments, the remote controller can be located within the same drug delivery device that contains the alternate step drive 1200 or 2200 and corresponding drug cartridge (e.g., within the same drug delivery device attached or coupled to a user). In various embodiments, the remote controller can be located in a device that is separate from the drug delivery device that contains the alternate step drive 1200 or 2200 and corresponding drug cartridge (e.g., within a handheld device that is separate and apart from the drug delivery device attached or coupled to a user).

Figure 23A:
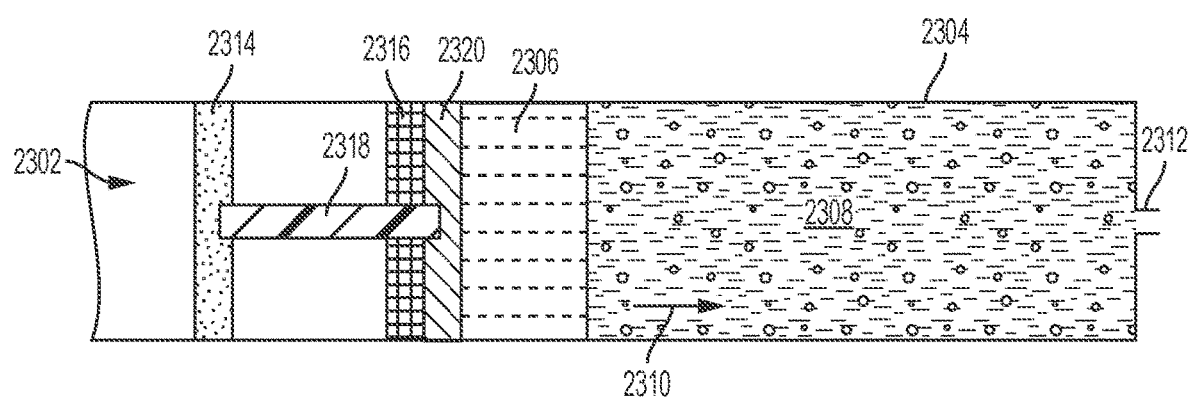
FIG. 23A illustrates a first stage of operation of a schematic representation of a resetting step drive.

FIG. 23A-23D illustrate operation of an exemplary resetting drive or resetting step drive 2302. FIGS. 23A-23F illustrate the resetting drive 2302 schematically. As shown in FIG. 23A, the resetting drive 2302 can be positioned within a cartridge 2304 and can be coupled to a plunger 2306. The cartridge 2304 can represent any type of cartridge, vial, or container for holding or storing a liquid 2308 such as, for example, a liquid drug or other therapeutic agent. The plunger 2306 can be formed from a rubber material. The plunger 2306 can form a seal with the cartridge 2304 to retain and store the liquid drug 2308. When the plunger 2306 is advanced in a direction 2310, the plunger 2306 can expel a portion of the liquid drug 2308 from an exit port or outlet 2312 of the cartridge 2304 for delivery to a patient or user.

The resetting drive 2302 can be operated to advance the plunger 2306 in the direction 2310. Accordingly, the resetting drive 2302 can operate as a drive system or a portion thereof that can determine an amount of the liquid drug 2308 that is delivered to the user by regulating advancement of the plunger 2306 to expel the liquid drug 2308 from the container 2304.

The resetting drive 2302 can include a first brake member or component 2314, a second brake member or component 2316, a connector member or component 2318, and a plunger coupling member or component 2320. The connector component 2318 can be coupled to the first brake component 2314 and the plunger coupling component 2320. To advance the plunger 2306, the second brake component 2316 can remain in a fixed position as the first brake component 2314, the connecting member 2318, and the plunger coupling component 2320 move in unison in the direction 2310, thereby pushing the plunger 2306 in the direction 2310. As a result, a portion of the stored liquid drug 2308 is expelled from the container 2304.

The plunger 2310 can be advanced until the first brake component 2314 is positioned next to the second brake component 2306. When the first brake component 2314 is adjacent to the second brake component 2316, the second brake component 2316 can be allowed to move in the direction 2310 as the first brake component 2314, the connector component 2318, and the plunger coupling component 2320 are held in fixed positions. In this way, the resetting drive 2302 is reset to await initiation of another cycle for advancing the plunger 2306.

FIGS. 23A-23D illustrate a sequence of steps or operations implemented by the resetting drive 2302 to provide a driving force on the plunger 2306. FIG. 23A shows a first operational state of the resetting drive 2302. In particular, the second brake component 2316 is positioned adjacent to the plunger coupling component 2320 and the first brake component 2314 is spaced apart from the second brake component 2316.

Figure 23B:
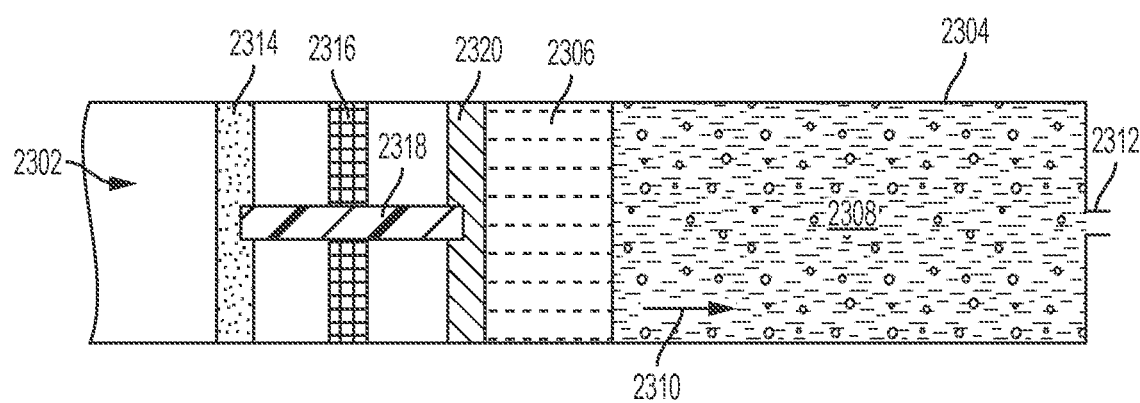
FIG. 23B illustrates a second stage of operation of the schematic representation of the resetting step drive.

FIG. 23B illustrates a second operational state of the resetting drive 2302, or a subsequent operational state of the resetting drive 2302 relative to the depiction of the resetting drive 2302 in FIG. 23A. As shown, the first brake component 2314, the connector component 2318, and the plunger coupling component 2320 have each moved in the direction 2310 and the second brake component 2316 has remained in a fixed position. The second brake component 2316 can be coupled to the connector component 2318 in a manner that allows the connector component 2318 to move in the direction 2310 while the positioning of the second brake component 2316 remains fixed.

The first brake component 2314, the connector component 2318, and the plunger coupling component 2320 can each move in the direction 2310 by the same approximate amount relative to the depiction of these components in FIG. 23A. As a result, the plunger 2306 has been advanced in the direction 2310 by approximately the same amount.

Figure 23C:
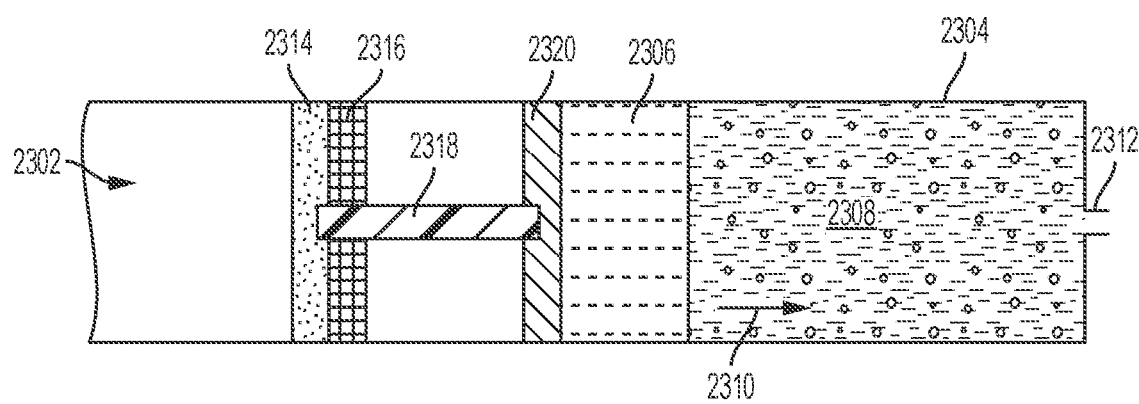
FIG. 23C illustrates a third stage of operation of the schematic representation of the resetting step drive.

FIG. 23C illustrates a third operational state of the resetting drive 2302, or a subsequent operational state of the resetting drive 2302 relative to the depiction of the resetting drive 2302 in FIG. 23B. As shown, the first brake component 2314, the connector component 2318, and the plunger coupling component 2320 have each moved further in the direction 2310 while the second brake component 2316 has remained in a fixed position. The plunger 2306 has also moved further in the direction 2310. The first brake component 2314 is adjacent to the second brake component 2316. As a result, further forward movement of the first brake component 2314 (and therefore the plunger 2316) is restricted.

Figure 23D:
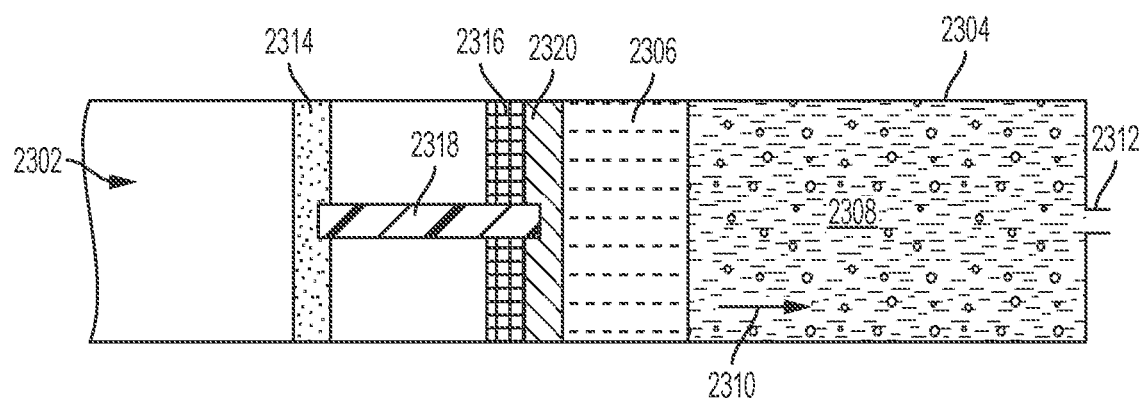
FIG. 23D illustrates a fourth stage of operation of the schematic representation of the resetting step drive.

FIG. 23D illustrates a fourth operational state of the resetting drive 2302, or a subsequent operational state of the resetting drive 2302 relative to the depiction of the resetting drive 2302 in FIG. 23C. As shown, the second brake component 2316 has been moved in the direction 2310 as the first brake component 2314, the connector component 2318, and the plunger coupling component 2320 have remained in a fixed position. The second brake component 2316 has been advanced to a position adjacent to the plunger coupling component 2320. Moving the second brake component 2316 to the position shown in FIG. 23D "resets" the resetting drive 2302 such that the plunger 2306 can be further advanced in the direction 2310.

FIGS. 23A-23C can represent operational states of the resetting drive 2302 during a first cycle of operation. FIG. 23D can represent an operational state of the resetting drive during the start of a second cycle of operation, as the first brake component 2314, the connector component 2318, and the plunger coupling component 2320 are ready to be advanced further in the direction 2310.

The resetting drive 2302 can be controlled to expel any portion of the liquid drug 2308 to the user. As an example, the resetting drive 2302 can be controlled to deliver substantially all of the liquid drug 2308 to the user in a single dose. Alternatively, the resetting drive 2302 can be controlled to deliver the liquid drug to the user over two or more doses (multiple or multi-doses). In various embodiments, the liquid drug 2308 can be insulin and the resetting drive 2302 can operate as a drive system for an insulin delivery system capable of precisely controlling bolus or basal amounts of insulin to the user. The resetting drive 2302 can be configured to provide a desired step size for advancing the plunger 2306 to provide precise control of the amount of the liquid drug 2308 expelled from the container 2304.

Figure 24:
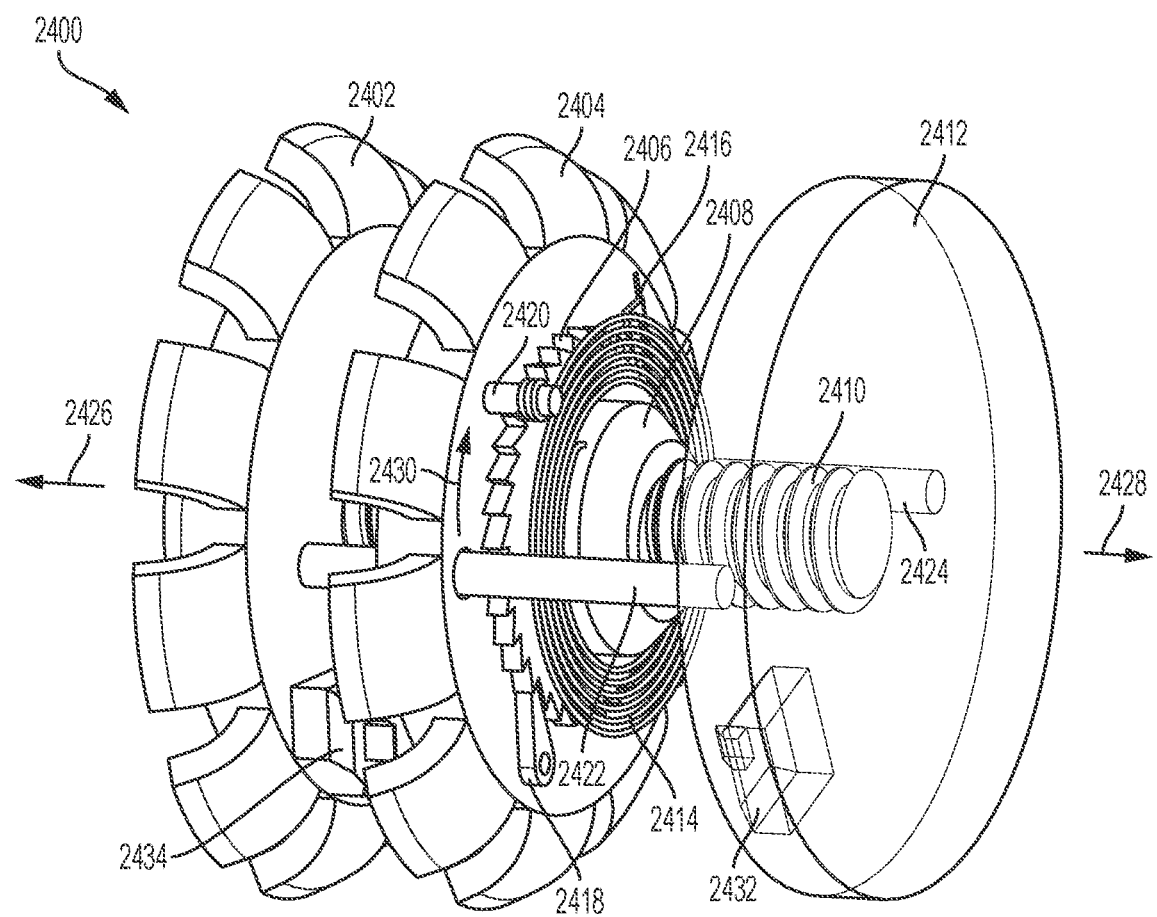
FIG. 24 illustrates a first view of a first exemplary resetting lead screw drive.

FIG. 24 illustrates a first exemplary resetting lead screw drive 2400. The first exemplary resetting lead screw drive 2400 can represent an implementation of the resetting drive 2300. As shown in FIG. 24, the resetting lead screw drive 200 can include a first brake member or component 2402, a second brake member or component 2404, a ratchet gear 2406, a nut 2408, a threaded shank or lead screw 2410, a plunger coupling member or component 2412, and a spring 2414. The lead screw 2410 can be positioned through the nut 2408, the ratchet 2406, and the second brake 2404. The lead screw 2410 can be coupled to the plunger coupling component 2412.

As further shown in FIG. 24, the resetting lead screw drive 2400 can include a drive pawl 2416, a stop pawl 2418, an extension member 2420, a first shaft component 2422, and a second shaft component 2424. The spring 2414 can be coupled to the nut 2408 and can be coupled to the extension member 2420. The extension member 2420 can extend from the second brake component 2404. The first and second shaft components 2422 and 2424 can be coupled to the plunger coupling component 2412 and can be positioned through the second brake component 2404.

The resetting lead screw drive 2400 can be used to drive a plunger (not shown in FIG. 24). The plunger can be coupled (e.g., directly attached or connected) to the plunger coupling component 2412. The resetting lead screw drive 2400 and the plunger can be positioned within a drug container. The first and second brake components 2402 and 2404 can be one-way brakes or self-energizing brakes that prevent or restrict movement in a direction 2426 while allowing movement in a direction 2428 (e.g., opposite the direction 2426). Accordingly, to expel a portion of liquid drug from a drug container, the resetting lead screw drive 2400 can be advanced in the direction 2428 to advance an attached plunger in the same direction.

To advance the resetting lead screw drive 2400 in the direction 2428, the drive pawl 2416 can be operated to rotate the ratchet 2406 in a direction 2430. The stop pawl 2418 can prevent the ratchet from rotating in a direction opposite the direction 2430. The ratchet 2406 and the nut 2408 can be coupled together such that the rotation of the ratchet 2406 can be transferred to the nut 2408. Since the second brake component 2404 prevents movement in the direction 2426, the rotation of the nut 2408 pushes the lead screw 2410 in the direction 2428. The lead screw 2410 can also be coupled to the first brake member 2402. Accordingly, as the lead screw 2410 is advanced in the direction 2428, the first brake component 2402 and the plunger coupling component 2412 are also similarly advanced in the direction 2428. As the lead screw 2410, the first brake component 2402, and the plunger coupling component 2412 move in unison, the second brake component 2404 is held in a fixed position.

As the ratchet 2406 is rotated in the direction 2430, the spring 2414 can be tightened to store the associated torque. Further, as the first brake component 2402 is advanced in the direction 2428, the first brake component 2402 is moved closer to the stationary second brake component 2404. When the first brake component 2402 is positioned adjacent to the second brake component 2404, a ramp component 2434 positioned on the first brake component 2402 can disengage the stop pawl 2418 from the ratchet 2406. When the stop pawl 2418 is disengaged from the ratchet 2406, the stored energy from the spring 2414 causes the ratchet 2406 to rotate in a direction opposite the direction 2430. Additionally, the nut 2408 is caused to rotate with the ratchet 2406 in the direction opposite the direction 2430. Since the first brake component 2402 is stationary and restricted from moving in the direction 2426, the second brake component 2404 is advanced in the direction 2428 with the rotation of the nut 2408.

As the second brake component 2404 is advanced in the direction 2428, the first brake component 2402 and the plunger coupling component 2412 are held in fixed positions. The second brake component 2404 can be advanced until it is adjacent to the plunger coupling component 2412. When the second brake component is adjacent to the plunger coupling component 2412, a ramp component 2432 on the plunger coupling component 2412 can re-engage the stop pawl 2418 with the ratchet 2406. As a result, the rotation of the ratchet 2406 is stopped and the spring 2414 is restricted from unwinding further. The ratchet 2406 can then be rotated in the direction 2430 again to advance the first brake component 2402, the lead screw 2410, and the plunger coupling component 2412 as the second brake component 2404 is held in a fixed position.

In various embodiments, operation of the resetting lead screw drive 2400 to advance the first brake component 2402, the lead screw 2410, and the plunger coupling component 2412 as the second brake component 2404 is stationary can be considered a first cycle of operation. Operation of the resetting lead screw drive 2400 to advance the second brake component 2404 as the first brake component 2402, the lead screw 2410, and the plunger coupling component 2412 are held stationary can be considered a second cycle of operation (or a resetting operation). The various cycles of operation of the resetting lead screw drive 2400 can be repeated as desired to expel a desired amount of liquid drug from a container.

In various embodiments, each of the end and front brake components 2402 and 2408 can include a main body having a plurality of extension components. The extension components can make contact with an inner wall of a container to restrict movement in a first direction while allowing direction in a second, opposite direction. The main body can be rigid while the extension components can be flexible or bendable.

Figure 25:
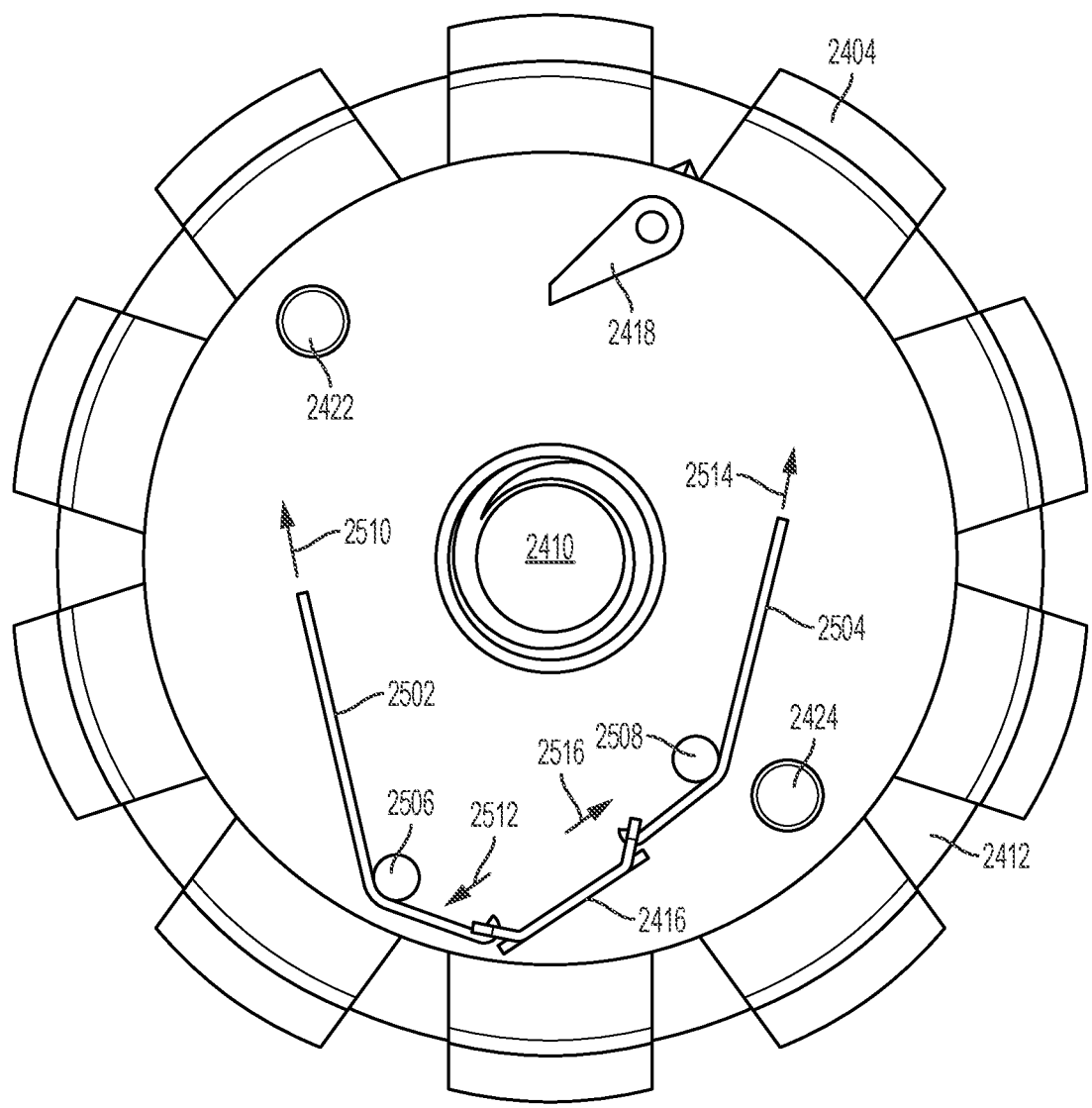
FIG. 25 illustrates a first view of a brake component of the first exemplary resetting lead screw drive.

FIG. 25 illustrates a view of the back of the second brake component 2404 (e.g., a view of the second brake component 2404 from the first brake component 2402 looking toward the plunger coupling component 2412). As shown in FIG. 25, the lead screw 2410 is positioned in a center of the second brake component 2404 and the first and second shaft components 2422 and 2422 are peripherally positioned through the second brake component 2404 on either side of the lead screw 2410. A component of the stop pawl 2418 and a component of the drive pawl 2416 are positioned on a back surface of the second brake component 2404.

The drive pawl 2416 can be coupled to a first wire 2502 and to a second wire 2504. The first wire 2502 can be coupled to a first end of the drive pawl 2416 and the second wire 2504 can be coupled to a second end of the drive pawl 2416. Each of the wires 2502 and 2504 can each be a shape memory wire including, for example, a Nitinol wire. The first wire 2502 can be routed around a first extension component 2506 and the second wire 2504 can be routed around a second extension component 2508.

When the first wire 2502 (e.g., as a Nitinol wire) is activated (e.g., by applying a current to the Nitinol wire), the Nitinol wire 2502 can contract. When the Nitinol wire 2502 contracts, it can be moved in a direction 2510, thereby causing the drive pawl 2416 to move in a direction 2512. Similarly, when the second wire 2504 (e.g., as a Nitinol wire) is activated (e.g., by applying a current to the Nitinol wire), the Nitinol wire 2504 can contract. When the Nitinol wire 2504 contracts, it can be moved in a direction 2514, thereby causing the drive pawl 2416 to move in a direction 2516. By alternating activation of the first and second Nitinol wires 2502 and 2504, the drive pawl 2416 can be moved back and forth repeatedly (in the directions 2512 and 2516). As a result, the ratchet 2406 can be rotated in the direction 2430 as shown in FIG. 24 through engagement of the dive pawl 2416 with the teeth of the ratchet 2406.

Figure 26:
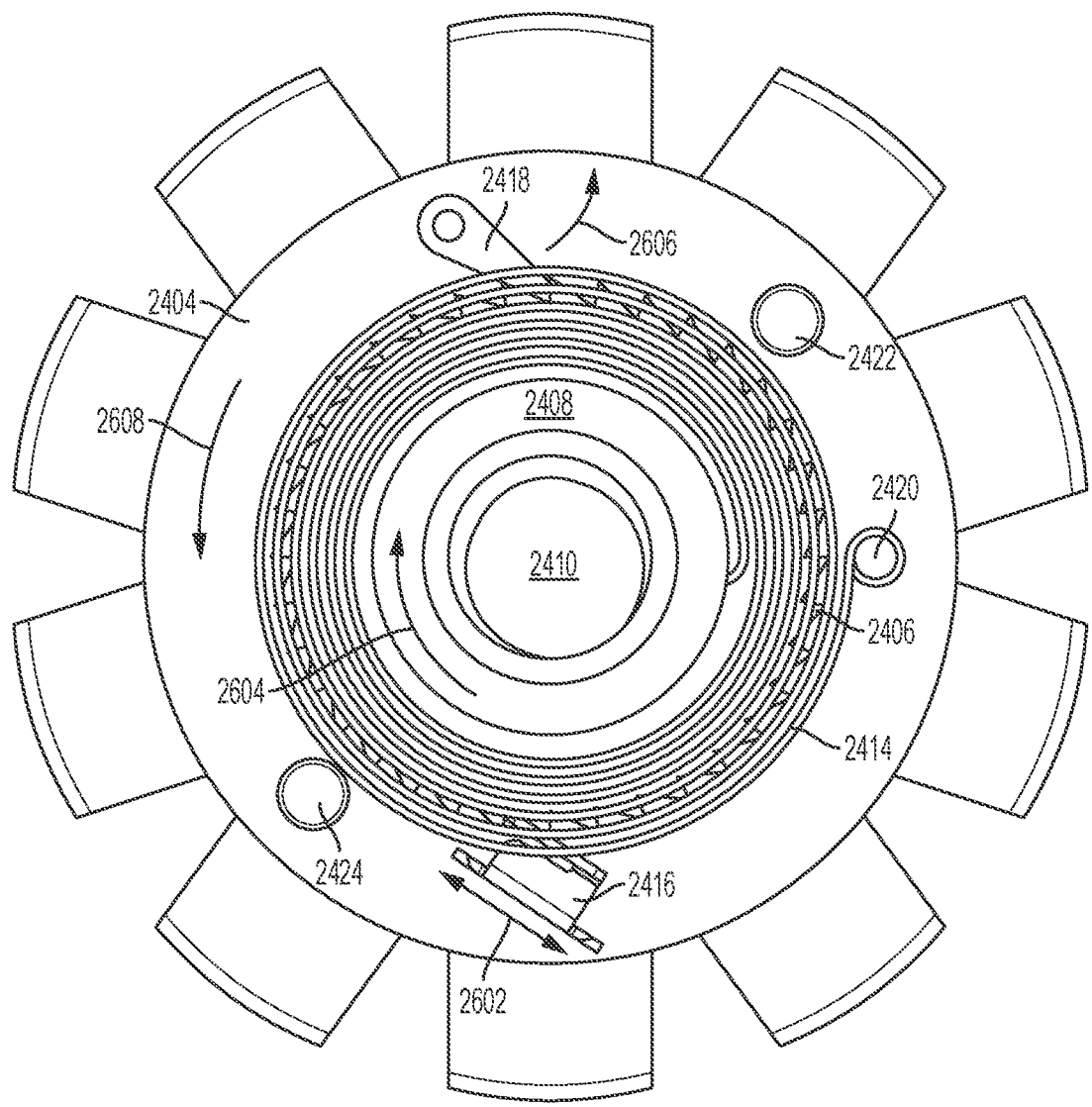
FIG. 26 illustrates a second view of the brake component of the first exemplary resetting lead screw drive.

FIG. 26 illustrates a view of the front of the second brake component 2404 (e.g., a view of the second brake component 2404 from the plunger coupling component 2414 looking toward the first brake component 2402). As shown in FIG. 26, the lead screw 2410 is positioned in a center of the second brake component 2404 and the first and second shaft components 2422 and 2422 are peripherally positioned through the second brake component 2404 on either side of the lead screw 2410. The nut 2408 is positioned around the lead screw 2410. The ratchet 2406 is positioned behind the nut 2408. The teeth of the ratchet 2406 are engaged by the drive pawl 2416 and the stop pawl 2418. The spring 2414 is coupled to the nut and the extension component 2420.

Indicator 2602 shows a movement of the drive pawl 2416 as the drive pawl 2416 is moved back and forth in the directions 2512 and 2516 as shown in FIG. 25. The movement of the drive pawl 2416 as shown by indicator 2602 causes the drive pawl 2416 to rotate the ratchet 2406 (and consequently the nut 2408) in a direction 2604. The direction 2604 can correspond to the direction 2430 shown in FIG. 24. As disclosed herein, the rotation of the nut 2408 can cause the spring 2414 to be tightened. The stop pawl 2418 as shown can engage the teeth of the ratchet 2406 to prevent the ratchet from rotating in a direction opposite to the direction 2604.

The stop pawl 2418 can be disengaged from the teeth of the ratchet 2406 when the stop pawl is rotated upward in a direction 2606. As disclosed herein, when the stop pawl 2418 is disengaged from the ratchet 2406, the ratchet 2406 and the nut 2408 can be allowed to move in a direction 2608. The stored energy from the wound spring 2414 can provide a force to cause the ratchet 2406 and the nut 2408 to rotate in the direction 2608.

The movement of the ratchet 2406 and the nut 2408 in the first direction 2604 can be considered a first portion of a cycle of operation of the resetting lead screw drive 2400. During the first portion of the cycle of operation, as disclosed herein, the first brake component 2402, the lead screw 2410, and the plunger coupling component 2412 can be moved in unison in a forward direction (e.g., in the direction 2428 as shown in FIG. 24) as the second brake component 2404 is maintained in a fixed position. The movement of the ratchet 2406 and the nut 2408 in the second direction 2608 can be considered a second portion of the cycle of operation of the resetting lead screw drive 2400. During the second portion of the cycle of operation, as disclosed herein, the second brake member can be moved in a forward direction (e.g., in the direction 2428 as shown in FIG. 24) as the first brake member 2402, the lead screw 2410, and the plunger coupling component 2412 are held in stationary positions. The second portion of the cycle of operation can be considered a resetting operation in reference to the resetting of the position of the second brake component 2404 relative to the other components of the resetting lead screw drive 2400.

Over a complete cycle, the resetting lead screw drive 2400 is moved forward, causing an attached plunger to be moved forward. The cycle can be repeated as desired to continue driving a plunger into a drug cartridge to expel a desired amount of liquid drug for delivery to a patient.

Figure 27:
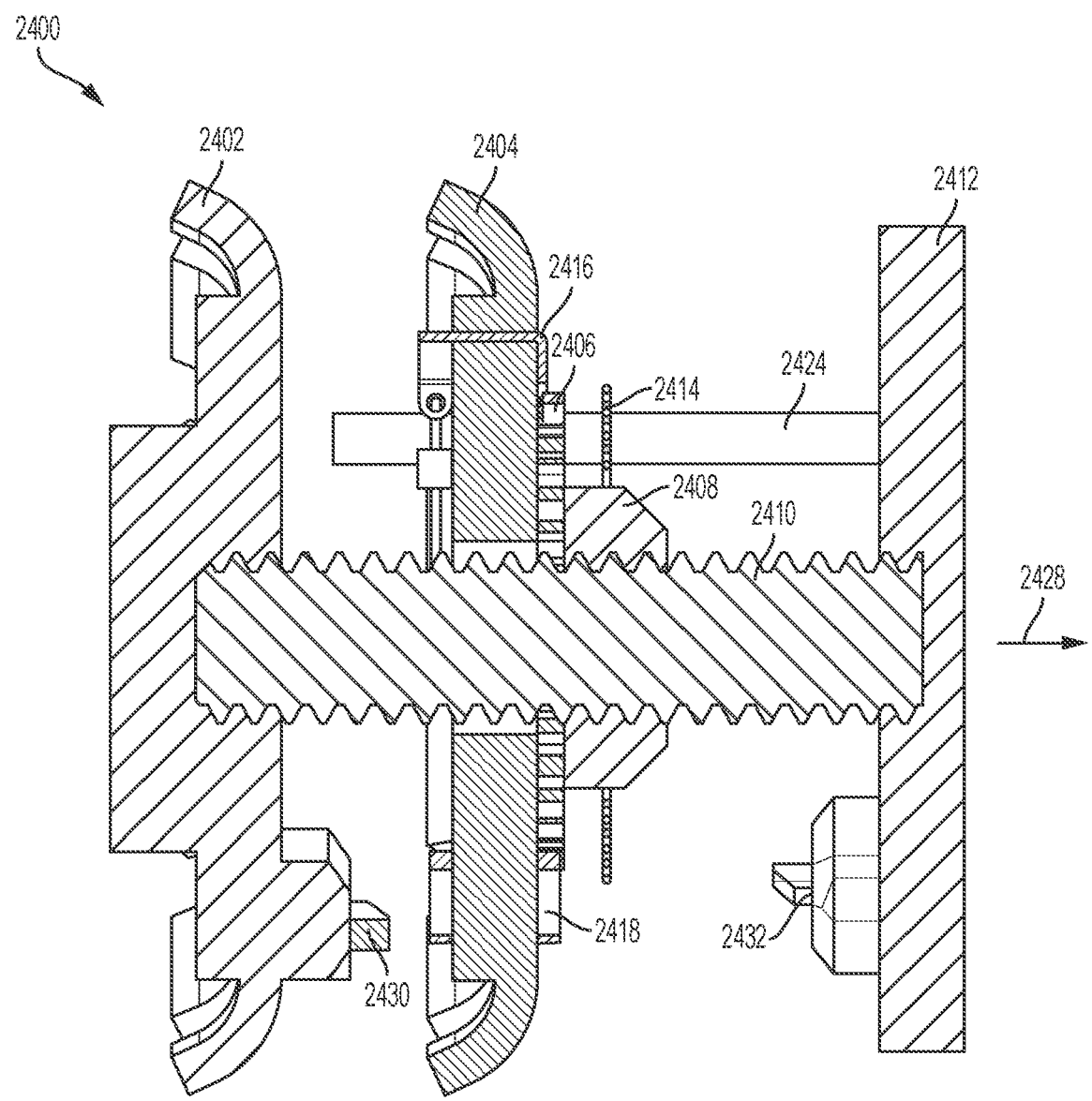
FIG. 27 illustrates a first stage of operation of the first exemplary resetting lead screw drive.
Figure 28:
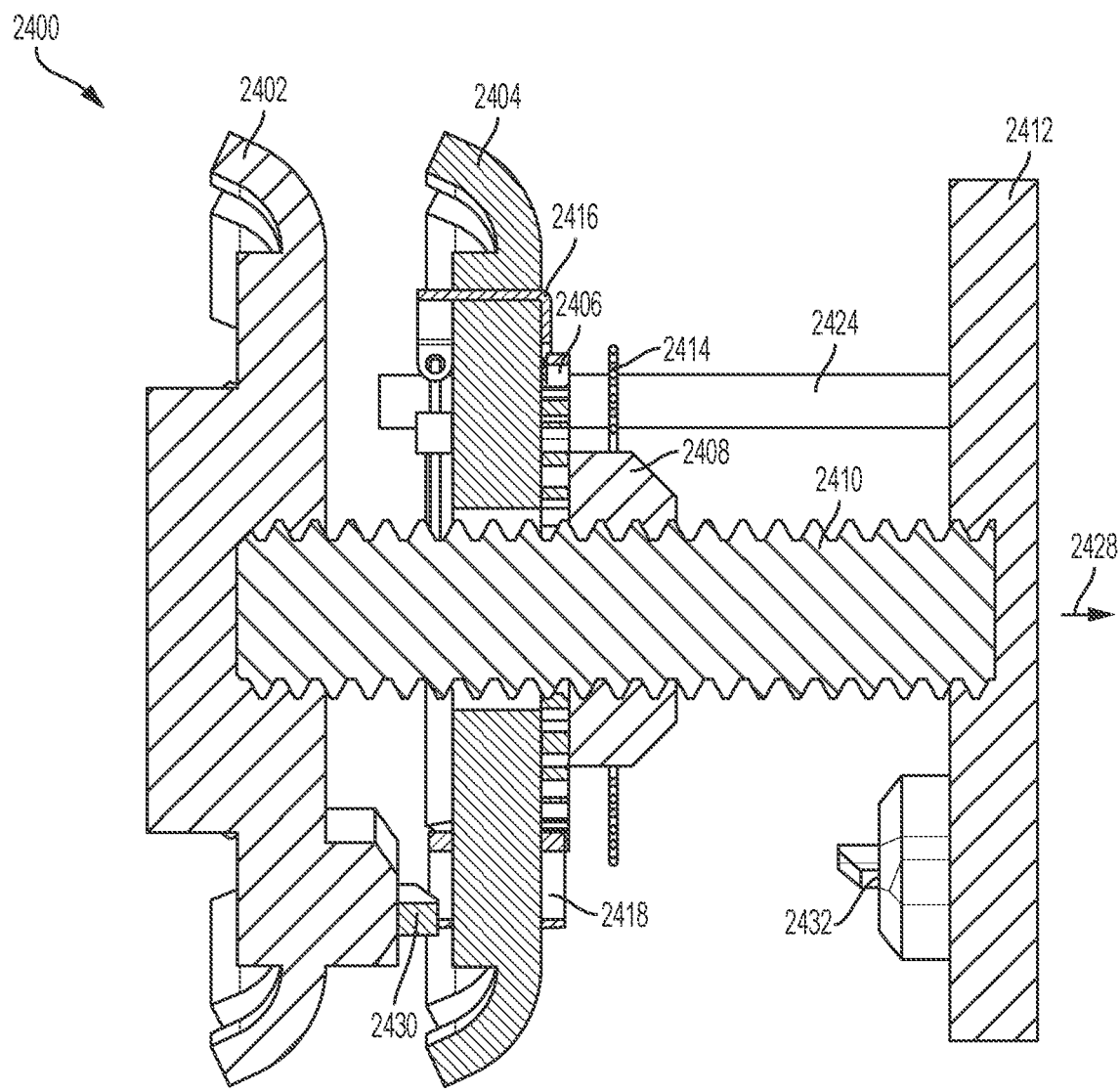
FIG. 28 illustrates a second stage of operation of the first exemplary resetting lead screw drive.
Figure 29:
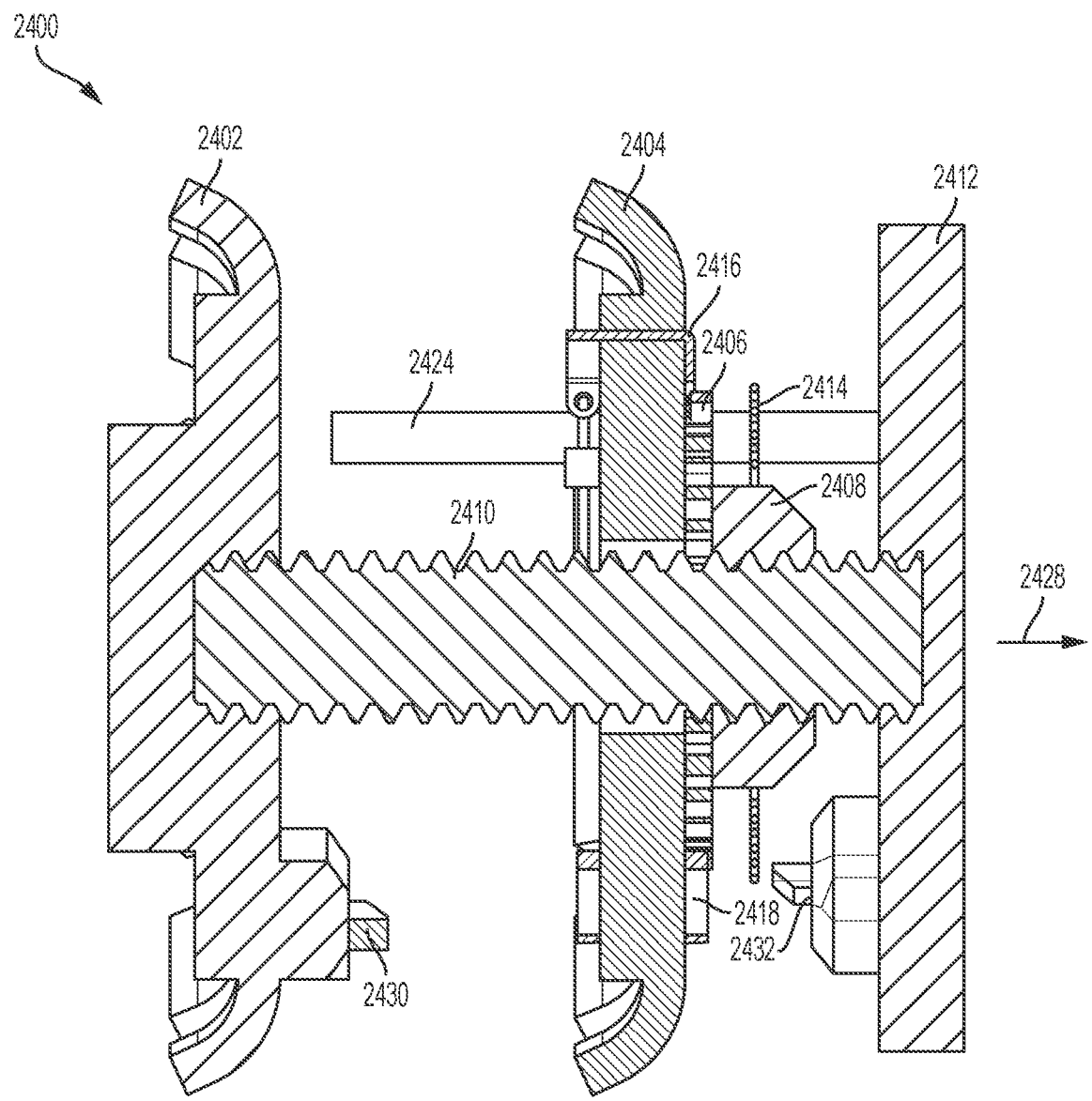
FIG. 29 illustrates a third stage of operation of the first exemplary resetting lead screw drive.

FIGS. 27-29 illustrate operation of the resetting lead screw drive 2400. Each of FIGS. 27-29 show a cross-sectional side view of the resetting lead screw drive 2400 during different stages of operation. FIGS. 27-29 show the arrangement of the various components of the resetting lead screw drive 2400. FIG. 27 shows the resetting lead screw drive 2400 as the second brake component 2404 is held in a fixed position as the first brake component 2402, the lead screw 2410, and the plunger coupling component 2412 are moved together in the direction 2428.

As shown in FIG. 27, the lead screw 2410 is coupled to the plunger coupling component 2412. The lead screw 2410 can push the plunger coupling component 2412 in the direction 2428 but does not rotate the plunger coupling component 2412. The lead screw 2410 is also coupled to the first brake component 2402. The lead screw 2410 can pull the first brake component 2402 in the direction 2428 but does not rotate the first brake component 2402. The lead screw 2410 is also positioned through center regions of the second brake component 2404, the ratchet 2406, and the nut 2408.

The lead screw is not directly coupled to the second brake component 2404 or the ratchet 2406 but is coupled to the nut 2408. Specifically, threads of the nut 2408 are engaged with threads of the lead screw 2410. Accordingly, rotation of the nut 2408 can cause the lead screw 2410 to rotate in response. The ratchet 2406 is coupled to the nut 2408 such that rotation of the ratchet 2406 can be imparted to the nut 2408. Rotation of the lead screw 2410 does not cause the second brake component 2404 to rotate.

FIG. 27 illustrates a stage of operation of the resetting lead screw drive 2400 during which the first brake component 2402 is moving in the direction 2428 but is not yet adjacent to the second brake component.

FIG. 28 illustrates a stage of operation of the resetting lead screw drive 2400 subsequent to the stage of operation shown in FIG. 27. As shown in FIG. 28, the first brake component 2402, the lead screw 2410, and the plunger coupling component 2412 have moved further in the direction 2428 relative to the depiction of these components in FIG. 27. The first brake component 2402 is (approximately) adjacent to the second brake component 2404 such that the ramp component 2434 can contact the stop pawl 2418. When the ramp component 2434 contacts the stop pawl 2418, the stop pawl 2418 can be disengaged from the ratchet 2406. As a result, the ratchet 2406 can be rotated in the opposite direction, as disclosed herein in relation to FIGS. 24-26, based on wound spring 2414 unwinding.

As the ratchet 2406 is rotated when the first brake component 2402 is held stationary, the nut 2408 can be rotated along the lead screw 2410 so as to move in the direction 2428 toward the plunger coupling component 2412. The second brake component 2404, coupled to the nut 2408 through the ratchet 2406, can also be advanced in the direction 2428.

FIG. 29 illustrates a stage of operation of the resetting lead screw drive 2400 subsequent to the stage of operation shown in FIG. 28. As shown in FIG. 29, the second brake component 2404 has moved further in the direction 2428 relative to the depiction of the second brake component 2404 in FIG. 28. The first brake component 2402, the lead screw 2410, and the plunger coupling component 2412 have remained stationary.

The second brake component 2404 is (approximately) adjacent to the plunger coupling component 2412 such that the ramp component 2432 can contact the stop pawl 2418. When the ramp component 2432 contacts the stop pawl 2418, the stop pawl 2418 can re-engage the ratchet 2406. As a result, rotation of the ratchet 2406 and the nut 2408 can be stopped. Further release or unwinding of the spring 2414 can also be stopped. The resetting lead screw drive 2400 is then ready to be operated to rotate the ratchet 2406 such that the first brake component 2402, the lead screw 2410, and the plunger coupling component 2412 are moved together in the direction 2428 while the second brake component 2404 is held in a fixed position, as shown in FIG. 27.

The stages of operation shown in FIGS. 27-29 can be repeated to incrementally move the components of the resetting lead screw drive 2400 in the direction 2428 as desired to expel liquid drug from a drug container.

Figure 30:
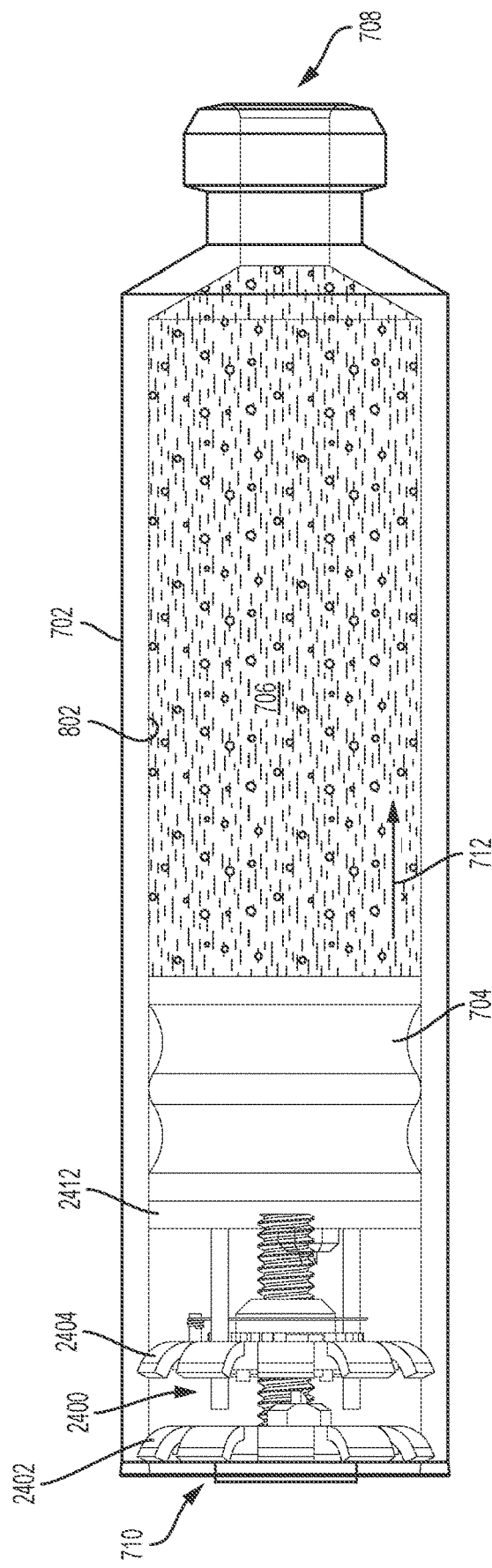
FIG. 30 illustrates the first exemplary resetting lead screw drive within a container.

FIG. 30 illustrates a side view of the resetting lead screw drive 2400 within the container 702. As shown in FIG. 30, the resetting lead screw drive 2400 can be positioned adjacent to the plunger 704. Specifically, the plunger coupling component 2412 can be coupled or connected to the plunger 704. The resetting lead screw drive 2400 can be positioned within the container 702 through the open end 710 of the container 702. The interior wall 802 can be engaged by the first and second brake components 2402 and 2404 to prevent movement in the direction toward the open end 710 of the container 702.

As disclosed herein, the resetting lead screw drive 2400 can be used to drive the plunger 704 toward the first end 708 of the container 702. The resetting lead screw drive 2400 can be coupled to the plunger 704 such that a force applied in the direction 712 by resetting lead screw drive 2400 can cause the plunger 704 to move incrementally in the direction 712, thereby causing a portion of the stored liquid drug 706 to be expelled from the container 702 (e.g., through an opening in the end 708).

Figure 31:
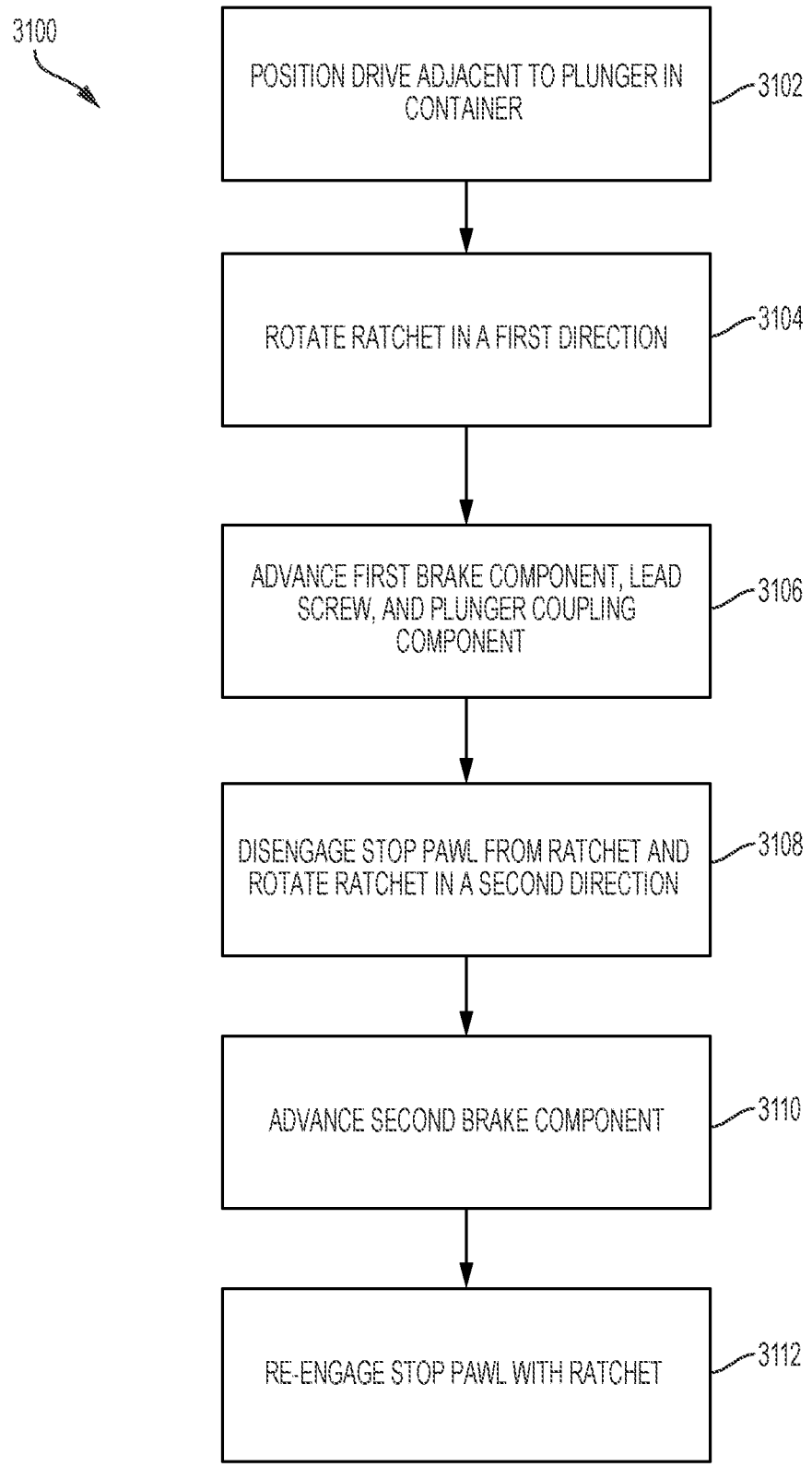
FIG. 31 illustrates an exemplary method of operation for the first exemplary resetting lead screw drive

FIG. 31 illustrates an exemplary method of operation 3100 for the resetting lead screw drive 2400. At 3102, the resetting lead screw drive 2400 can be positioned adjacent to a plunger within a drug cartridge holding a liquid drug. The resetting lead screw drive 2400 can be positioned within an open end of the drug cartridge. The plunger coupling component 2412 can be coupled to the plunger. The drug cartridge can be an ISO drug cartridge and can store any type of therapeutic agent including any liquid drug. The drug cartridge can be coupled to a user.

In an initial operational state, the first and second brake components 2402 and 2404 can be displaced from one another, with the second brake component 2404 positioned adjacent to the plunger coupling component 2412.

At 3104, the drive pawl 2416 can be moved so as to rotate the ratchet 2406 in a first direction (e.g., the direction 2430 as shown in FIG. 24). The drive pawl 2416 can be moved by alternatively activating and deactivating two Nitinol wires 2502 and 2504. Successively contracting and releasing each of the Nitinol wires 2502 and 2504 can cause the drive pawl 2416 to engage the teeth of the ratchet 2406. The rotation of the ratchet 2406 can cause the nut 2408 to rotate in the first direction. Further, as the nut 2408 is being rotated in the first direction, the spring 2414 can be tightened.

At 3106, the rotation of the nut 2408 can cause the lead screw 2410 to be advanced toward the plunger (e.g., in the direction 2428 as shown in FIG. 24). With the second brake component 2404 held in a fixed position, the movement of the lead screw 2410 can further cause the first brake component 2402 and the plunger coupling component 2412 to be advanced toward the plunger. As a result, the plunger can be advanced further into the container, causing a portion of the stored liquid drug to be expelled from the container.

At 3108, the first brake component 2402, the lead screw 2410, and the plunger coupling component 2412 can be advanced (along with the plunger of the container) until the first brake component 2402 is adjacent to the second brake component 2404. The ramp component 2434 of the first brake component 2402 can then contact the stop pawl 2418 to disengage the stop pawl 2418 from the ratchet 2406. As a result, the ratchet 2406 can be allowed to rotate in a second direction (e.g., in a direction opposite to the direction 2430 of FIG. 24). The tightened spring 2414 can be released and allowed to cause the nut 2408 to rotate in the second direction.

At 3110, the first brake component 2402, the lead screw 2410, and the plunger coupling component 2412 can be maintained in fixed positions. As the nut 2408 is rotated in the second direction, the second brake component 2404 can be caused to advance toward the plunger. The plunger can remain stationary as the second brake component 2404 is moved in the direction 2428.

At 3112, the second brake component 2404 can be advanced until the second brake component 2402 is adjacent to the plunger coupling component 2412. The ramp component 2432 of the plunger coupling component 2412 can then contact the stop pawl 2418 to re-engage the stop pawl 2418 with the ratchet 2406. As a result, the ratchet 2406 and the nut 2408 are restricted from rotating further in the second direction and the spring 2414 no longer unwinds. The resetting lead screw drive 2400 is now in a state awaiting movement of the drive pawl 2414 to once again rotate the ratchet 2406 in the first direction, to thereby cause the plunger to be advanced by the unified movement of the first brake component 2402, the lead screw 2410, and the plunger coupling component 2412.

The method of operation 3100 can be repeated as desired to continue to incrementally move the resetting lead screw drive 2400 and the plunger further into the drug cartridge, thereby expelling a desired amount of liquid drug from the cartridge for delivery to the user. The method of operation 3100 can represent a sequence of operations that can be implemented in sequence from any beginning initial step to provide the incremental movement of the plunger as disclosed herein. In various embodiments, the movement of the second brake component 2404 until the second brake component 2404 is adjacent the plunger coupling component 3212 (and the stop pawl 2418 is re-engaged) can be considered a resetting of the resetting lead screw drive 2400.

Figure 32:
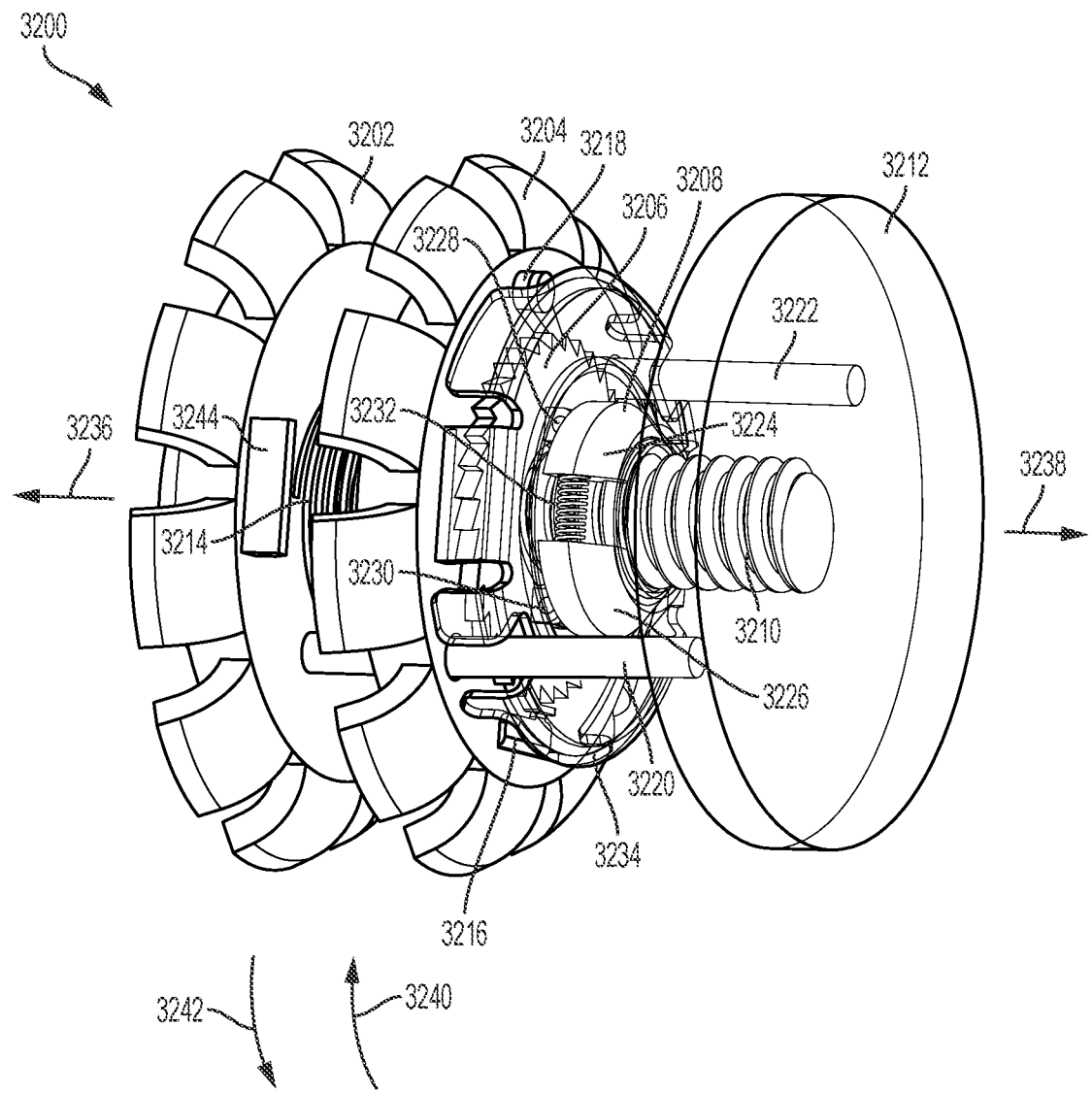
FIG. 32 illustrates a first view of a second exemplary resetting lead screw drive.

FIG. 32 illustrates a second exemplary resetting lead screw drive 3200. The second exemplary resetting lead screw drive 3200 can represent an implementation of the resetting drive 2300. As shown in FIG. 32, the resetting lead screw drive 3200 can include a first brake member or component 3202, a second brake member or component 3204, a ratchet gear 3206, a tilt nut 3208, a threaded shank or lead screw 3210, a plunger coupling member or component 3212, and a spring 3214. The lead screw 3210 can be positioned through the tilt nut 3208, the ratchet 3206, and the second brake component 3204. The lead screw 3210 can be coupled to the plunger coupling component 3212. The spring 3214 can be positioned between the first brake component 3202 and the second brake component 3204.

As further shown in FIG. 32, the resetting lead screw drive 3200 can include a drive pawl 3216, a stop pawl 3218, a first shaft component 3220, and a second shaft component 3222. The first and second shaft components 3220 and 3222 can be coupled to the plunger coupling component 3212 and can be positioned through the second brake component 3204.

The tilt nut 3208 can include a first tilt nut component 3224 and a second tilt nut component 3226. The first tilt nut component 3224 can be coupled to the ratchet 3206 by a first hinge 3228. The second tilt nut component 3226 can be coupled to the ratchet 3206 by a second hinge 3230. A first spring 3232 and a second spring (not shown in FIG. 32) can be positioned between the first tilt nut component 3224 and the second tilt nut component 3226. The first spring 3232 and the second spring can apply forces for pushing the first and second tilt nut components 3224 and 3226 apart and/or to rotate about the first and second hinges 3228 and 3230, respectively.

A cover component 3234 can be positioned over the tilt nut 3208. The cover component 3234 can maintain the tilt nut 3208 in the position as shown in FIG. 32—that is, engaged with the lead screw 3210. As disclosed herein, when at least a portion of the cover component 3234 is released, the tilt nut 3208 can be allowed to disengage the lead screw 3210. As a result, the first tilt nut component 3224 can rotate about the first hinge 3228 and the second tilt nut component 3226 can rotate about the second hinge 3230. In turn, the tilt nut 3208 becomes disengaged from the lead screw 3210.

The resetting lead screw drive 3200 can be used to drive a plunger (not shown in FIG. 3200). The plunger can be coupled to the plunger coupling component 3212. The resetting lead screw drive 3200 and the plunger can be positioned within a drug container. The first and second brake components 3202 and 3204 can be one-way brakes or self-energizing brakes that prevent or restrict movement in a direction 3236 while allowing movement in a direction 3238 (e.g., opposite the direction 3236). Accordingly, to expel a portion of liquid drug from a drug container, the resetting lead screw drive 3200 can be advanced in the direction 3238 to advance an attached plunger in the same direction.

To advance the resetting lead screw drive 3200 in the direction 3238, the drive pawl 3216 can be operated to rotate the ratchet 3206 in a direction 3240. The stop pawl 3218 can prevent the ratchet 3206 from rotating in a direction 3242 (e.g., opposite the direction 3240). When the first and second tilt nut components 3224 and 3226 are engaged with the lead screw 3210, the rotation of the ratchet 3206 can be transferred to the tilt nut 3208. Since the second brake component 3204 prevents movement in the direction 3236, the rotation of the tilt nut 3208 pushes the lead screw 3210 in the direction 3238. The lead screw 3210 can be coupled to the first brake component 3202. Accordingly, as the lead screw 3210 is advanced in the direction 3238, the first brake component 3202 and the plunger coupling component 3212 are also similarly advanced in the direction 3228. As the lead screw 3210 is moved in the direction 3238, the first brake component 3202 and the plunger coupling component 3212 move in unison, while the second brake component 3204 is held in a fixed position.

The movement of the first brake component 3202 in the direction 3238 reduces a distance separating the first brake component 3202 and the stationary second brake component 3204, while also compressing the spring 3214. As disclosed herein, when the first brake component 3202 is adjacent to the second brake component 3204, one or more ramp components 3244 can cause a portion of the cover component 3234 to be released. Releasing a portion of the cover component 3224 allows the first and second tilt nut components 3224 and 3236 to rotate about the first and second hinges 3228 and 3230, respectively, thereby disengaging from the lead screw 3210. With the tilt nut 3208 no longer engaged with the threads of the lead screw 3210, the spring 3214 can expand. When the spring 3214 expands, the spring 3214 can provide a force to push the second brake component 3204 in the direction 3228.

The first brake component 3202, the led screw 3210, and the plunger coupling component 3212 can remain in fixed positions as the spring 3214 pushes the second brake component 3204 in the direction 3238. The second brake component 3204 can be advanced until it is adjacent to the plunger coupling component 3212. When the second brake component 3204 is adjacent to the plunger coupling component 3212, the plunger coupling component 3212 can cause a portion of the cover component 3234 to re-engage the tilt nut 3208. As a result, the first and second tilt nut components 3224 and 3236 can be caused to rotate back to re-engage the lead screw 3210. After the tilt nut 3208 re-engages the lead screw 3210, the ratchet 2406 can once again be rotated in the direction 3240 to advance the first brake component 2402, the lead screw 2410, and the plunger coupling component 2412 as the second brake component 2404 is held in a fixed position. This cycle of movement can be repeated to expel a desired amount of liquid drug from a container as further disclosed herein.

The movement of the first brake component 3202, the lead screw 3210, and the plunger coupling component 3212 in the direction 3238 as the second brake component 3204 remains stationary can be considered a first cycle of operation of the resetting lead screw drive 3200. The movement of the second brake component 3204 in the direction 3238 as the first brake component 3202, the lead screw 3210, and the plunger coupling component 3212 remain stationary can be considered a second cycle of operation of the resetting lead screw drive 3200. This second cycle of operation can also be considered a resetting operation as subsequent to the movement of the second brake component 3204, the resetting lead screw drive 3200 is ready to advance the plunger forward again.

Figure 33:
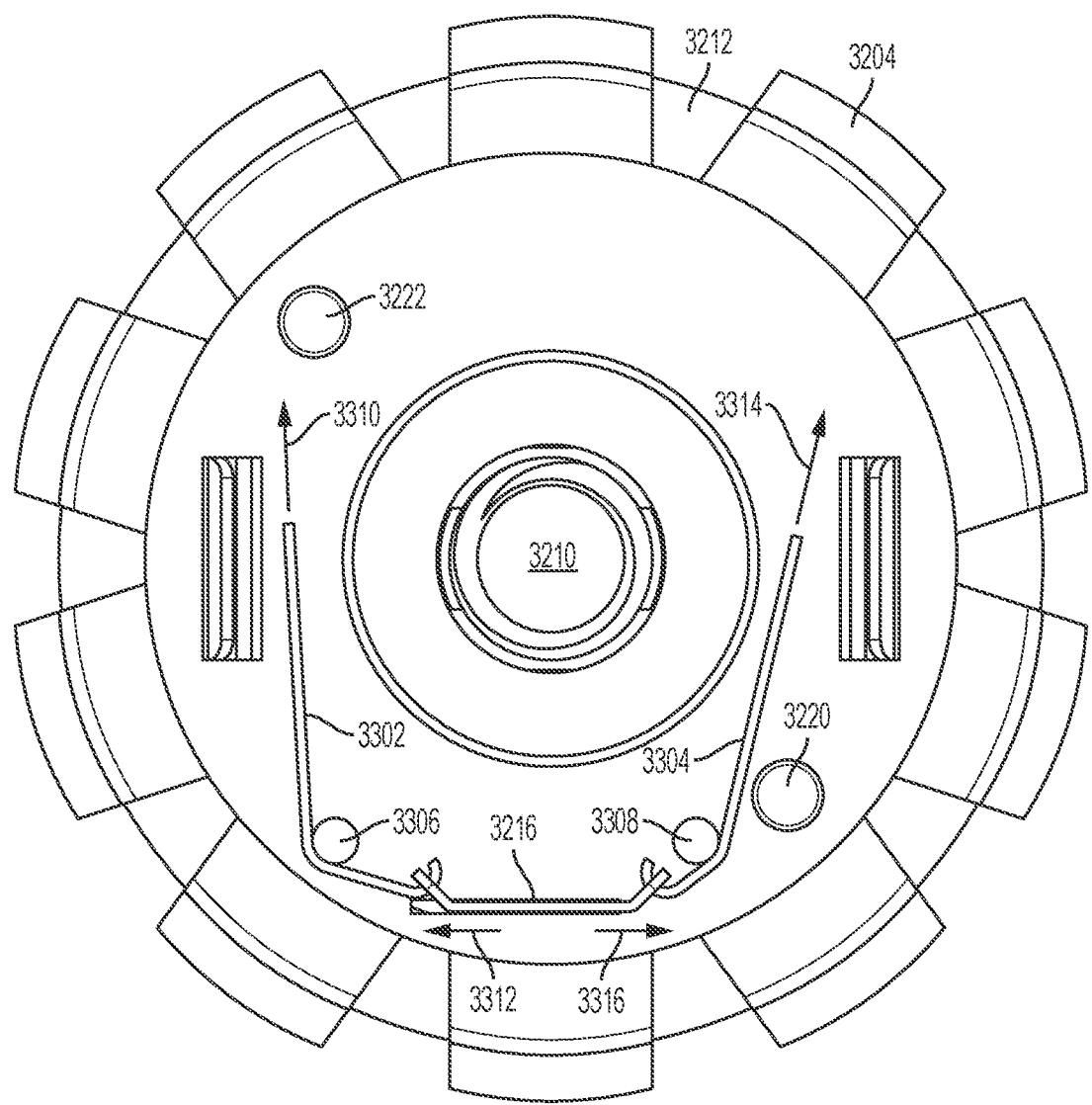
FIG. 33 illustrates a first view of a brake component of the second exemplary resetting lead screw drive.

FIG. 33 illustrates a view of the back of the second brake component 3202 (e.g., a view of the second brake component 3204 from the first brake component 3202 looking toward the plunger coupling component 3212). As shown in FIG. 33, the lead screw 3210 is positioned in a center of the second brake component 3204 and the first and second shaft components 3220 and 3222 are peripherally positioned through the second brake component 3204 on either side of the lead screw 3210. A component of the drive pawl 3216 is positioned on a back surface of the second brake component 3204.

The drive pawl 3216 can be coupled to a first wire 3302 and to a second wire 3304. The first wire 3302 can be coupled to a first end of the drive pawl 3216 and the second wire 3304 can be coupled to a second end of the drive pawl 3216. Each of the wires 3302 and 3304 can be a shape memory wire including, for example, a Nitinol wire. The first wire 3302 can be routed around a first extension component 3306 and the second wire 3304 can be routed around a second extension component 3308.

When the first wire 3302 (e.g., as a Nitinol wire) is activated (e.g., by applying a current to the Nitinol wire), the Nitinol wire 3302 can contract. When the Nitinol wire 3302 contracts, it can be moved in a direction 3310, thereby causing the drive pawl 3216 to move in a direction 3312. Similarly, when the second wire 3304 (e.g., as a Nitinol wire) is activated (e.g., by applying a current to the Nitinol wire), the Nitinol wire 3304 can contract. When the Nitinol wire 3304 contracts, it can be moved in a direction 3314, thereby causing the drive pawl 3216 to move in a direction 3316. By alternating activation of the first and second Nitinol wires 3302 and 3304, the drive pawl 3216 can be moved back and forth repeatedly. As a result, the ratchet 3206 can be rotated in the direction 3240 as shown in FIG. 32.

Figure 34:
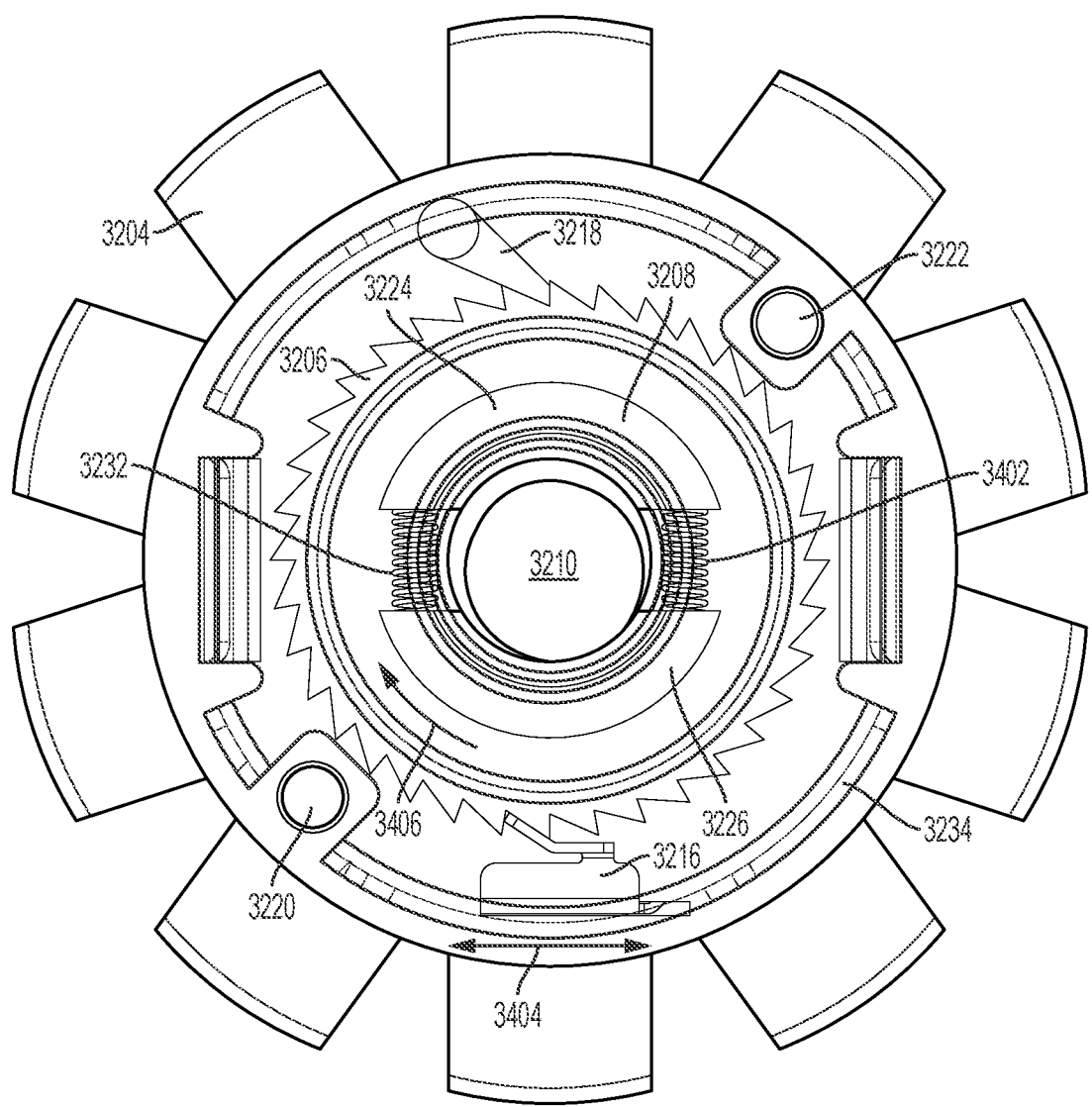
FIG. 34 illustrates a second view of the brake component of the second exemplary resetting lead screw drive.

FIG. 34 illustrates a view of the front of the second brake component 3204 (e.g., a view of the second brake component 3204 from the plunger coupling component 3214 looking toward the first brake component 3204). As shown in FIG. 34, the lead screw 3210 is positioned in a center of the second brake component 3204 and the first and second shaft components 3220 and 3222 are peripherally positioned through the second brake component 3204 on either side of the lead screw 3210. The tilt nut 3208 is positioned around the lead screw 3208. Specifically, the first tilt nut component 3224 and the second tilt nut component 3226 are engaged with the lead screw 3208. The spring 3222 and the spring 3404 are positioned between the first and second tilt nut components 3224 and 3226. The cover component 3224 or a portion thereof maintains the arrangement of the first and second tilt nut components 3224 and 3226 as shown in FIG. 34. The ratchet 3206 is positioned behind the tilt nut 3208. The teeth of the ratchet 3206 are engaged by the drive pawl 3216 and the stop pawl 3218.

Indicator 3404 shows a movement of the drive pawl 3216 as the drive pawl 3216 is moved back and forth in the directions 3312 and 3316 as shown in FIG. 33. The movement of the drive pawl 3216 as shown by indicator 3404 causes the drive pawl 3216 to rotate the ratchet 3206 (and consequently the tilt nut 3208) in a direction 3406. The direction 3406 can correspond to the direction 3240 shown in FIG. 32. The stop pawl 3218 as shown can engage the teeth of the ratchet 3206 to prevent the ratchet from rotating in a direction opposite to the direction 3406.

The movement of the ratchet 3206 and the tilt nut 3208 in the direction 3406 can be considered a first portion of a cycle of operation of the resetting lead screw drive 3200. During the first portion of the cycle of operation, as disclosed herein, the first brake member 3202, the lead screw 3210, and the plunger coupling component 3212 can be moved in unison in a forward direction (e.g., in the direction 3238 as shown in FIG. 32) as the second brake component 3204 is maintained in a fixed position.

A second portion of a cycle of operation of the resetting lead screw drive 3200 can occur when the tilt nut 3208 is disengaged from the lead screw. During the second portion of the cycle of operation, as disclosed herein, the second brake member can be moved in a forward direction (e.g., in the direction 3238 as shown in FIG. 32) as the first brake member 3202, the lead screw 3210, and the plunger coupling component 3212 are held in stationary positions.

Over a complete cycle, the resetting lead screw drive 2400 is moved forward, causing an attached plunger to be moved forward. The cycle can be repeated as desired to continue driving a plunger into a drug cartridge to expel a desired amount of liquid drug for delivery to a patient.

Figure 35:
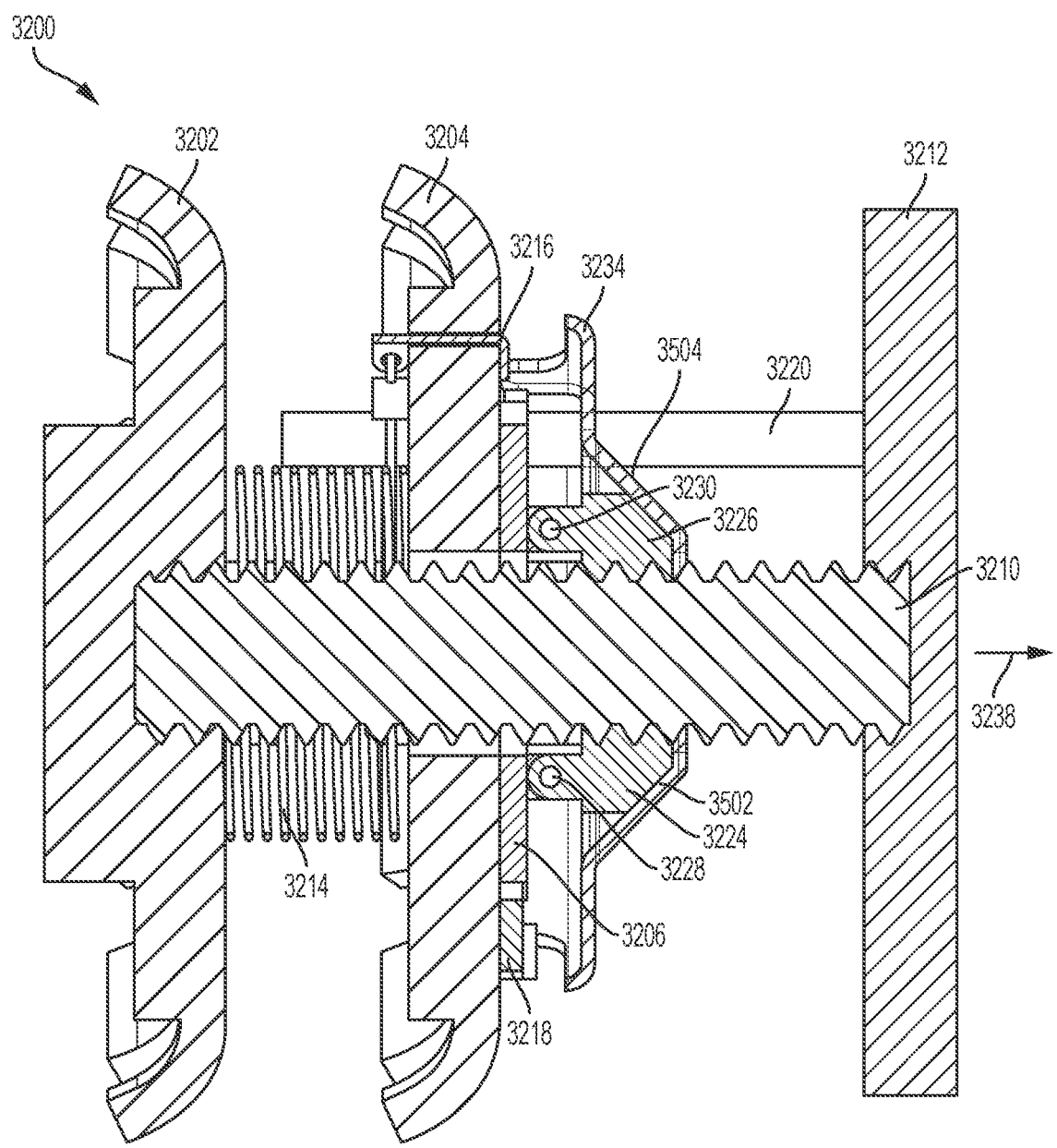
FIG. 35 illustrate a first cross-sectional side view of the second exemplary resetting lead screw drive.

FIG. 35 illustrates a first cross-sectional side view of the resetting lead screw drive 3200. FIG. 35 shows the arrangement of the various components of the resetting lead screw drive 3200. In particular, FIG. 35 shows the resetting lead screw drive 3200 as the second brake component 3204 is held in a fixed position as the first brake component 3202, the lead screw 3210, and the plunger coupling component 3212 are moved together in the direction 3238.

As shown in FIG. 35, the lead screw 3210 is coupled to the plunger coupling component 3212. The lead screw 3210 can push the plunger coupling component 3212 in the direction 3238 but does not rotate the plunger coupling component 3212. The lead screw 3210 is also coupled to the first brake component 3202. The lead screw 3210 can pull the first brake component 3202 in the direction 3238 but does not rotate the first brake component 3202. The lead screw 3210 is also positioned through center regions of the second brake component 3204, the ratchet 3206, and the tilt nut 3208.

The lead screw 3210 is not directly coupled to the second brake component 3204 or the ratchet 3206 but can be selectively coupled to the tilt nut 2408, as disclosed herein. Specifically, threads of the tilt nut 3208 can be selectively engaged with threads of the lead screw 3210. Accordingly, rotation of the tilt nut 3208 can cause the lead screw 3210 to rotate in response. The ratchet 3206 is coupled to the tilt nut 3208 such that rotation of the ratchet 3206 can be imparted to the tilt nut 3208

As further shown in FIG. 35, the first tilt nut component 3224 is coupled to the ratchet 3206 by the hinge 3228 and the second tilt nut component 3226 is coupled to the ratchet 3206 by the hinge 3238. The cover component 3234 is positioned over the ratchet 3206 and the tilt nut 3208. As a portion of the cover component 3234 or as separate components, the resetting lead screw drive 3200 can include a first top hat component 3502 and a second top hat component 3504. The first top hat component 3502 can be pressed down on the tilt nut component 3324, causing the tilt nut component 3224 to remain engaged with the lead screw 3210. Similarly, the second top hat component 3504 can be pressed down on the tilt nut component 3226, causing the tilt nut component 3236 to remain engaged with the lead screw 3210. When the first and second top hat components 3602 and 3604 are released, the tilt nut components 3224 and 3226 can be allowed to rotate about the first and second hinges 3228 and 3230, respectively. As a result, the first and second tilt nut components 3224 and 3226 can be disengaged from the lead screw 3210. In various embodiments, a single top hat component can be used—for example, the first and second top hat components 3502 and 3504 can be coupled together to form one operational unit.

When the tilt nut 3208 is no longer engaged with the lead screw 3210, the spring 3214 can be allowed to expand and can drive the second brake component 3204 in the direction 3238 while the first brake component 3202, the lead screw 3210, and the plunger coupling component 3212 remain in fixed positions. In this way, the resetting lead screw drive 3200 "resets" by advancing the second brake component 3204 forward until it is adjacent to the plunger coupling component 3212. Once adjacent to the plunger coupling component 3212, the plunger coupling component 3212 can force the first and second top hat components 3602 and 3604 back into the positions shown in FIG. 35, thereby causing the tilt nut 3208 to re-engage the lead screw 3210.

Figure 36:
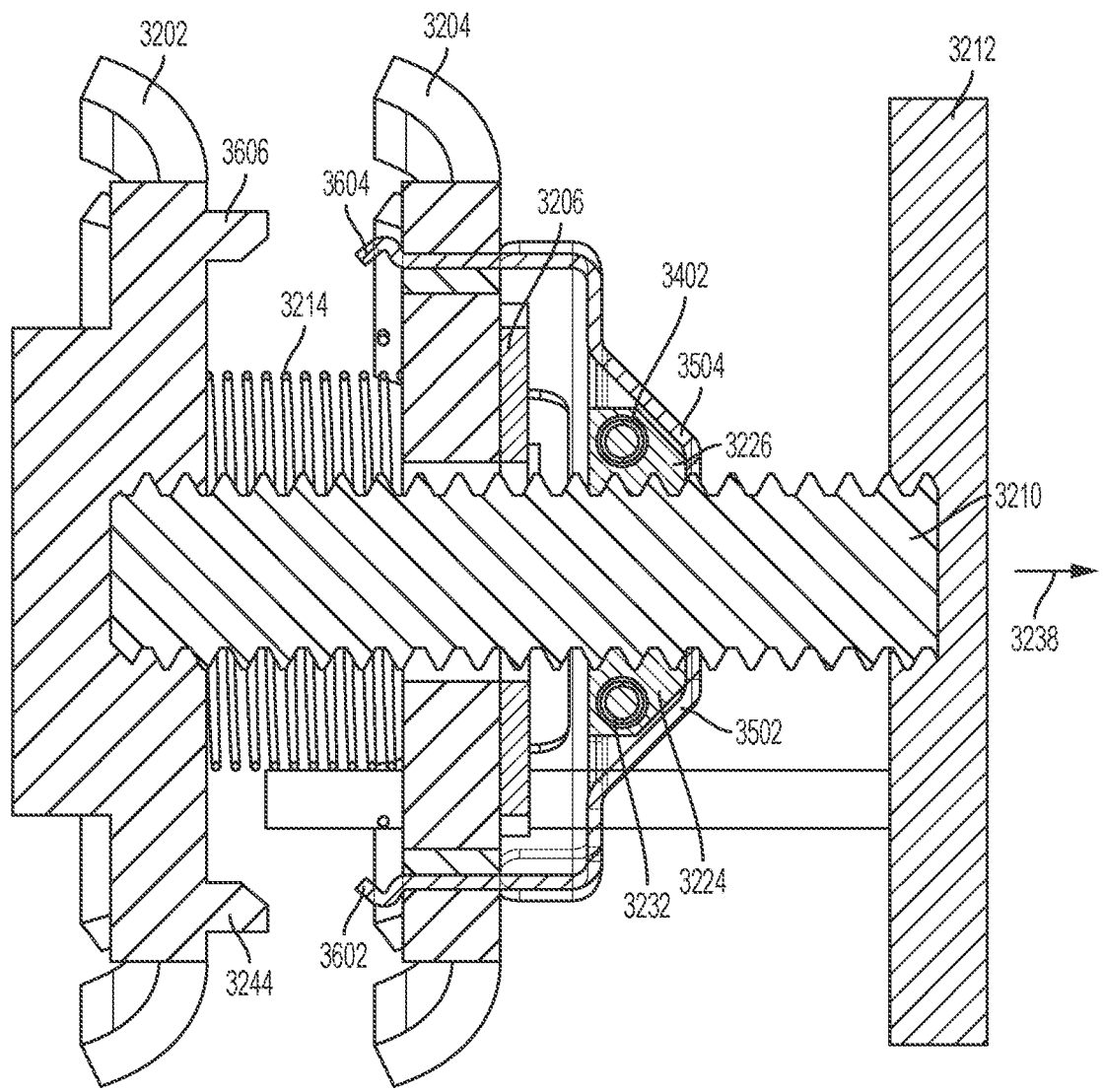
FIG. 36 illustrate a second cross-sectional side view of the second exemplary resetting lead screw drive.

FIG. 36 illustrates a second cross-sectional side view of the resetting lead screw drive 3200. FIG. 36 shows the arrangement of the various components of the resetting lead screw drive 3200 that can disengage the tilt nut 3208 from the lead screw 3210. In particular, FIG. 36 shows the resetting lead screw drive 3200 as the second brake component 3204 is held in a fixed position as the first brake component 3202, the lead screw 3210, and the plunger coupling component 3212 are moved together in the direction 3238.

As further shown in FIG. 36, the first top hat component 3502 can be coupled to a first top hat snap 3602. The first top hat snap 3602 can be positioned through the second brake component 3404. A second top hat snap 3604 can be coupled to the second top hat component 3504 and can also be positioned through the second brake component 3404. As shown in FIG. 36, the positioning of the top hat snaps 3602 and 3604 maintain the positioning of the top hat components 3502 and 3504, respectively.

When the first brake component 3202 is adjacent to the second brake component 3204, the ramp component 3244 can engage the top hat snap 3602. Similarly, a ramp component 3606 can engage the top hat snap 3604. When the top hat snaps 3602 and 3604 are engaged by the ramp components 3244 and 3606, respectively, the top hat snaps 3602 and 3604 can be dislodged (e.g., moved from a steady state position), thereby disengaging the first and second top hat components 3502 and 3504, respectively. Specifically, the first and second top hat components 3502 and 3504 can be released from covering the first and second tilt nut components 3224 and 3226. As a result of disengaging the top hat snaps 3602 and 3604, the spring 3214 can drive the second brake component forward in the direction 3238. In various embodiments, with a single top hat component, the top hat snaps 3602 and 3604 can also release the top hat component.

Further, because the top hat components 3502 and 3504 no longer restrict movement of the tilt nut components 3224 and 3226. The tilt nut components 3224 and 3226 can rotate about the hinges 3228 and 3230, respectively, causing the tilt nut 3208 to disengage from the lead screw 3210. The second brake component 3204 is free to move forward in the direction 3238. Once the second brake component 3204 reaches the plunger coupling component 3212, the top hat components 3502 and 3504 and top hat snaps 3602 and 3604 can be directed back into their initial positions. Further, the tilt nut 3408 re-engages the lead screw 3210.

Figure 37:
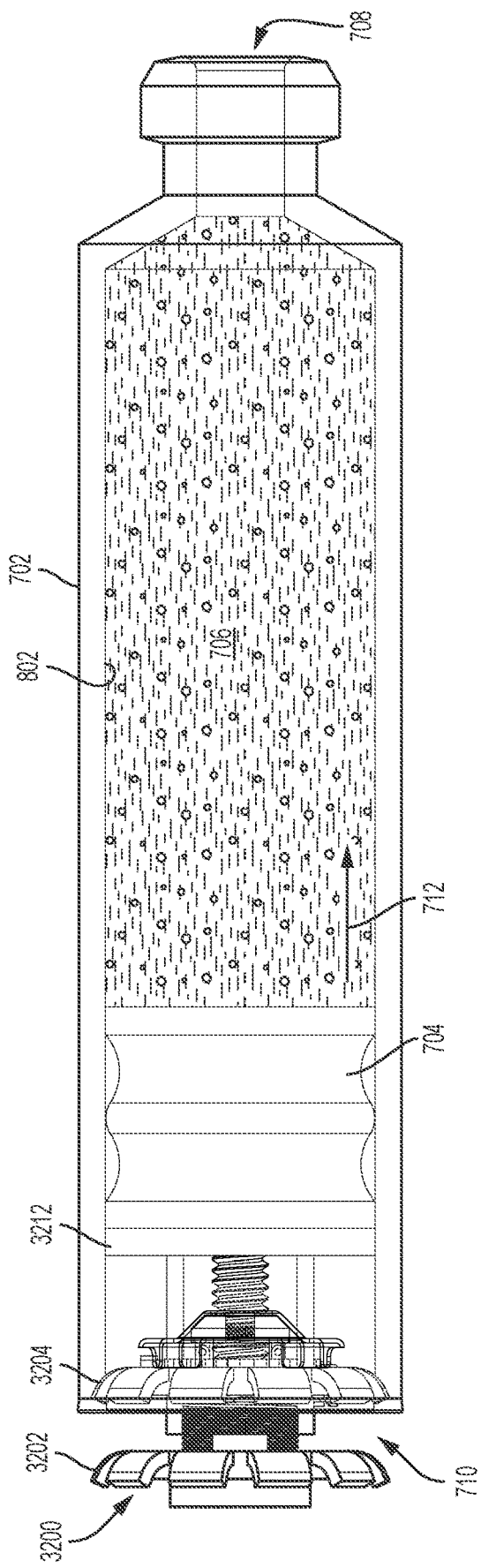
FIG. 37 illustrates a first view of the second exemplary resetting lead screw drive within a container.

FIG. 37 illustrates a side view of the resetting lead screw drive 3200 within the container 702. As shown in FIG. 37, the resetting lead screw drive 3200 can be positioned adjacent to the plunger 704. Specifically, the plunger coupling component 3212 can be coupled or connected to the plunger 704. The resetting lead screw drive 3200 can be positioned within the container 702 through the open end 710 of the container 702. The interior wall 802 can be engaged by the first and second brake components 3202 and 3204 to prevent movement in the direction toward the open end 710 of the container 702.

As disclosed herein, the resetting lead screw drive 3200 can be used to drive the plunger 704 toward the first end 708 of the container 702. The resetting lead screw drive 3200 can be coupled to the plunger 704 such that a force applied in the direction 712 by resetting lead screw drive 3200 can cause the plunger 704 to move incrementally in the direction 712, thereby causing a portion of the stored liquid drug 706 to expelled from the container 702 (e.g., through an opening in the end 708).

Figure 38:
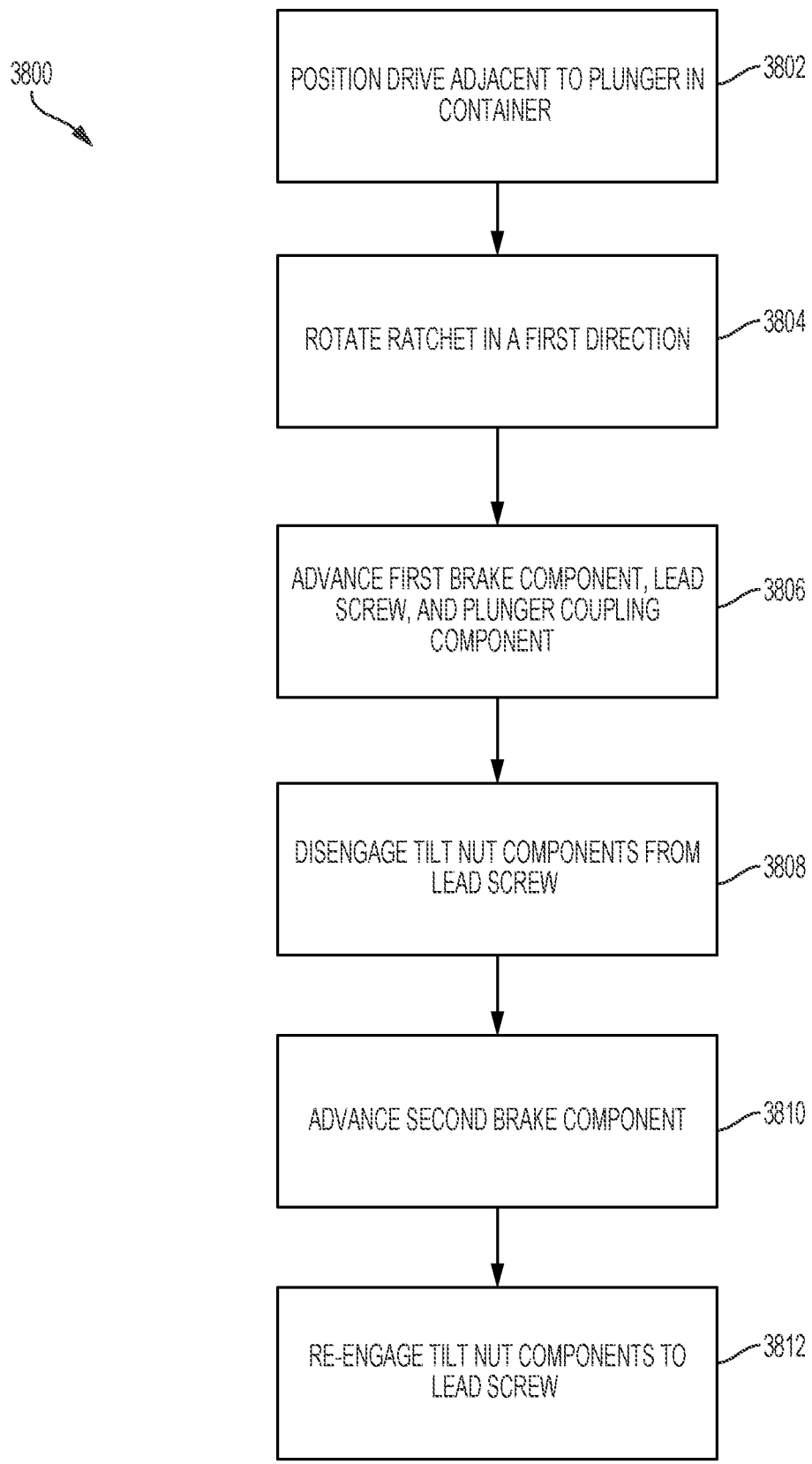
FIG. 38 illustrates an exemplary method of operation for the second exemplary resetting lead screw drive.

FIG. 38 illustrates an exemplary method of operation 3800 for the resetting lead screw drive 3200. At 3802, the resetting lead screw drive 3200 can be positioned adjacent to a plunger within a drug cartridge holding a liquid drug. The resetting lead screw drive 3200 can be positioned within an open end of the drug cartridge. The plunger coupling component 3212 can be coupled to the plunger. The drug cartridge can be an ISO drug cartridge and can store any type of therapeutic agent including any liquid drug. The drug cartridge can be coupled to a user.

In an initial operational state, the first and second brake components 3202 and 3204 can be displaced from one another, with the second brake component 3204 positioned adjacent to the plunger coupling component 3212.

At 3804, the drive pawl 3216 can be moved so as to rotate the ratchet 3206 in a first direction (e.g., the direction 3240 as shown in FIG. 32). The drive pawl 3216 can be moved by alternatively activating and deactivating two Nitinol wires 3302 and 3304. Successively contracting and releasing each of the Nitinol wires 3302 and 3304 can cause the drive pawl 3216 to engage the teeth of the ratchet 3206. The rotation of the ratchet 3206 can cause the nut 3208 to rotate in the first direction.

At 3806, the rotation of the nut 3208 can cause the lead screw 3210 to be advanced toward the plunger (e.g., in the direction 3238 as shown in FIG. 32). With the second brake component 3204 held in a fixed position, the movement of the lead screw 3210 can further cause the first brake component 3202 and the plunger coupling component 3212 to be advanced toward the plunger. As a result, the plunger can be advanced further into the container, causing a portion of the stored liquid drug to be expelled from the container.

At 3808, the first brake component 3202, the lead screw 3210, and the plunger coupling component 3212 can be advanced (along with the plunger of the container) until the first brake component 3202 is adjacent to the second brake component 3204. When the first brake component 3202 is adjacent to the second brake component 3204, the ramp components 3244 and 3606 can engage the top hat snaps 3602 and 3604, respectively. When the top hat snaps 3602 and 3604 are engaged, the first and second top hat components 3502 and 3504 disengage from the first and second tilt nut components 3224 and 3226, respectively. The first and second tilt nut components 3224 and 3226 are thereby allowed to disengage from the lead screw 3210 by rotating about the hinges 3228 and 3230, respectively.

At 3810, the first brake component 3203, the lead screw 3210, and the plunger coupling component 3212 can be maintained in fixed positions. When the first and second tilt nut components 3224 and 3226 are disengaged from the lead screw 3210, the spring 3214 can be allowed to expand. The expansion of the spring 3214 provides a force that pushes the second brake component forward (in the direction 3238 as shown in FIG. 32). The plunger can remain stationary as the second brake component 2404 is moved forward toward the plunger.

At 3812, the second brake component 3204 can be advanced until the second brake component 3204 is adjacent to the plunger coupling component 3212. The plunger coupling component 3212 can press on the top hat components 3502 and 3504. The top hat components 3502 and 3504 can push on the tilt nut components 3232 and 3234 causing the tilt nut components 3232 and 3234 to re-engage the lead screw. The movement of the top hat components 3502 and 3504 can further cause the top hat snaps 3602 and 3604 to be moved back into their original positions. The movement of the second brake components 3204 can be stopped along with expansion of the spring 3214.

The resetting lead screw drive 3200 is now in a state awaiting movement of the drive pawl 3216 to once again rotate the ratchet 3206 in the first direction, to thereby cause the plunger to be advanced by the unified movement of the first brake component 3202, the lead screw 3210, and the plunger coupling component 3212.

The method of operation 3800 can be repeated as desired to continue to incrementally move the resetting lead screw drive 3800 and the plunger further into the drug cartridge, thereby expelling a desired amount of liquid drug from the cartridge for delivery to the user. The method of operation 3800 can represent a sequence of operations that can be implemented in sequence from any beginning initial step to provide the incremental movement of the plunger as disclosed herein. In various embodiments, the movement of the second brake component 3204 until the second brake component 3204 is adjacent the plunger coupling component 3212 can be considered a resetting of the resetting lead screw drive 3200.

In various embodiments, the resetting lead screw drive 3200 and the resetting lead screw drive 2400 can each include a controller. The controller can control operation of the resetting lead screw drive 3200 and the resetting lead screw drive 2400. The controller can be directly attached or coupled to the resetting lead screw drive 3200 and the resetting lead screw drive 2400 or can be positioned remote from the resetting lead screw drive 3200 and the resetting lead screw drive 2400. Any controller used with the resetting lead screw drive 3200 or the resetting lead screw drive 2400 can include the same capabilities and arrangement as the controller 242 described in relation to the alternate step drive 200.

In various embodiments, the resetting lead screw drive 3200 and/or the resetting lead screw drive 2400 can use a manually enabled brake system and/or a cammed brake system. In various embodiments, the resetting lead screw drive 3200 and/or the resetting lead screw drive 2400 can use a geared ratchet (e.g., a geared up or down ratchet) to provide a different level of torque (e.g., more or less torque) to drive operations. In various embodiments, the resetting lead screw drive 3200 and/or the resetting lead screw drive 2400 can use a split nut that moves laterally as part of the reset mechanism. In various embodiments, the resetting lead screw drive 3200 and/or the resetting lead screw drive 2400 can use a rack and pinion system in lieu of a lead screw.

Each of the drive systems disclosed herein—for example, the alternate step drive 200, the alternate step drive 1200, the resetting lead screw drive 3200, and the resetting lead screw drive 2400—can be sized and arranged to be positioned within any type of drug container including, for example, any ISO cartridge. Each of the drive systems disclosed herein can be included or used as a component of a drug delivery device including, for example, a wearable drug delivery device that can dispense any type of drug to a user including insulin. Each of the drive systems disclosed herein can provide a predetermined incremental displacement of a plunger that can be varied based on a size of each drive system and/or a size of a container in which each drive system operates. Each of the drive systems disclosed herein can expel any amount of stored liquid drug from a container. Each of the drive systems disclosed herein can dispense the stored liquid drug in a single dose or over two or more doses.

The following first set of examples pertain to further embodiments.

Example 1 is an alternate step drive comprising a first brake component configured to expand and retract along a first axis, a second brake component configured to expand and retract along the first axis, and a connector component coupled to the first and second brake components and configured to expand and retract along a second axis approximately perpendicular to the first axis, wherein the first brake component, the second brake component, and the connector component are configured to advance a plunger positioned within a drug container to expel a portion of a stored liquid drug for delivery to a user.

Example 2 is an extension of Example 1 or any other example disclosed herein, wherein the first brake component, the second brake component, and the connector component are each configured to expand and retract independently.

Example 3 is an extension of Example 1 or any other example disclosed herein, wherein the first brake component comprises a first non-compressible component, a second non-compressible component, a compressible component positioned between the first and second non-compressible components, a shape memory wire wrapped around the first and second non-compressible components, a first rubber component wrapped around a first end of the first brake component, and a second rubber component wrapped around a second end of the first brake component.

Example 4 is an extension of Example 3 or any other example disclosed herein, wherein the shape memory wire comprises a Nitinol wire.

Example 5 is an extension of Example 4 or any other example disclosed herein, wherein the Nitinol wire is configured to contract when activated.

Example 6 is an extension of Example 5 or any other example disclosed herein, wherein the first and second non-compressible components are configured to compress the compressible component when the Nitinol wire is activated, thereby retracting the first brake component along the first axis.

Example 7 is an extension of Example 6 or any other example disclosed herein, wherein the compressible component is configured to expand when the Nitinol wire is deactivated, thereby expanding the first brake component along the first axis.

Example 8 is an extension of Example 7 or any other example disclosed herein, wherein the first and second rubber components are configured to contact an inner wall of the drug container when the first brake component is expanded along the first axis.

Example 9 is an extension of Example 8 or any other example disclosed herein, wherein the first and second rubber components are configured to not contact the inner wall of the drug container when the first brake component is retracted along the first axis.

Example 10 is an extension of Example 9 or any other example disclosed herein, wherein the connector component comprises a compressible component positioned between the first and second brake components.

Example 11 is an extension of Example 10 or any other example disclosed herein, wherein the connector component comprises a shape memory wire wrapped around the first and second brake components.

Example 12 is an extension of Example 11 or any other example disclosed herein, wherein the shape memory wire wrapped around the first and second brake components comprises a Nitinol wire.

Example 13 is an extension of Example 12 or any other example disclosed herein, wherein the Nitinol wire wrapped around the first and second brake components is configured to contract when activated.

Example 14 is an extension of Example 13 or any other example disclosed herein, wherein the first and second brake components are configured to compress the compressible component positioned between the first and second brake components when the Nitinol wire wrapped around the first and second brake components is activated, thereby retracting the connector component along the second axis.

Example 15 is an extension of Example 14 or any other example disclosed herein, wherein the compressible component positioned between the first and second brake components is configured to expand when the Nitinol wire wrapped around the first and second brake components is deactivated, thereby expanding the connector component along the second axis.

Example 16 is an extension of Example 1 or any other example disclosed herein, further comprising a controller configured to control expansion and retraction of the first brake component, the second brake component, and the connector component.

Example 17 is an extension of Example 16 or any other example disclosed herein, wherein the controller is coupled to the first brake component.

Example 18 is an extension of Example 16 or any other example disclosed herein, wherein the controller is remote from the alternate step drive.

Example 19 is an extension of Example 18 or any other example disclosed herein, wherein the alternate step drive comprises a receiver for receiving control instructions from the remote controller.

The following second set of examples pertain to further embodiments.

Example 1 is an alternate step drive comprising a first brake component, a second brake component, a first cap component coupled to the first brake component, a second cap component coupled to the second brake component and the first cap component, and a rotational motor positioned between the first and second cap components and coupled to the first and second brake components, wherein rotation of the rotational motor is configured to advance a plunger positioned within a drug container to expel a portion of a stored liquid drug for delivery to a user.

Example 2 is an extension of Example 1 or any other example disclosed herein, wherein the rotational motor comprises a shape memory wire and a shaft component.

Example 3 is an extension of Example 2 or any other example disclosed herein, wherein the shape memory wire comprises a Nitinol wire.

Example 4 is an extension of Example 3 or any other example disclosed herein, wherein the shaft component is configured to rotate in a first direction when the Nitinol wire is activated.

Example 5 is an extension of Example 4 or any other example disclosed herein, wherein the front brake component comprises a first brake arm.

Example 6 is an extension of Example 5 or any other example disclosed herein, wherein the first brake arm is configured to disengage from an inner wall of the drug container when the shaft component is rotated in the first direction.

Example 7 is an extension of Example 6 or any other example disclosed herein, wherein the first cap component is configured to advance toward the plunger when the shaft component is rotated in the first direction.

Example 8 is an extension of Example 7 or any other example disclosed herein, wherein the shaft component is configured to rotate in a second direction when the Nitinol wire is deactivated, the second direction opposite to the first direction.

Example 9 is an extension of Example 8 or any other example disclosed herein, wherein the rotational motor further comprises a spring.

Example 10 is an extension of Example 9 or any other example disclosed herein, wherein the spring is configured to rotate the shaft component in the second direction when the Nitinol wire is deactivated.

Example 11 is an extension of Example 10 or any other example disclosed herein, wherein the second brake component comprises a second brake arm.

Example 12 is an extension of Example 11 or any other example disclosed herein, wherein the second brake arm is configured to disengage from the inner wall of the drug container when the shaft component is rotated in the second direction.

Example 13 is an extension of Example 12 or any other example disclosed herein, wherein the second cap component is configured to advance toward the plunger when the shaft component is rotated in the second direction.

Example 14 is an extension of Example 13 or any other example disclosed herein, wherein the first brake component comprises a first brake spring configured to bias the first brake arm against the inner wall of the drug container until the shaft component is rotated in the first direction.

Example 15 is an extension of Example 14 or any other example disclosed herein, wherein the first brake arm is configured to restrict advancement of the first cap component toward the plunger until the shaft component is rotated in the first direction.

Example 16 is an extension of Example 15 or any other example disclosed herein, wherein the second brake component comprises a second brake spring configured to bias the second brake arm against the inner wall of the drug container until the shaft component is rotated in the second direction.

Example 17 is an extension of Example 16 or any other example disclosed herein, wherein the second brake arm is configured to restrict advancement of the second cap component toward the plunger until the shaft component is rotated in the second direction.

Example 18 is an extension of Example 1 or any other example disclosed herein, wherein the first and second brake components are self-energizing brakes.

The following third set of examples pertain to further embodiments.

Example 1 is a resetting lead screw drive comprising a first brake component, a second brake component, a plunger coupling component, a lead screw positioned through the second brake component and coupled to the first brake component and the plunger coupling component, a nut coupled to the lead screw, and a ratchet gear coupled to the nut, wherein rotation of the ratchet gear in a first direction is configured to advance the first brake component, the lead screw, and the plunger coupling component toward a plunger positioned within a drug container to expel a portion of a stored liquid drug for delivery to a user.

Example 2 is an extension of Example 1 or any other example disclosed herein, wherein the second brake component is configured to remain stationary as the first brake component, the lead screw, and the plunger coupling component are advanced toward the plunger.

Example 3 is an extension of Example 2 or any other example disclosed herein, further comprising a drive pawl configured to rotate the ratchet gear in the first direction.

Example 4 is an extension of Example 3 or any other example disclosed herein, further comprising two or more shape memory wires coupled to the drive pawl.

Example 5 is an extension of Example 4 or any other example disclosed herein, wherein the shape memory wires are Nitinol wires.

Example 6 is an extension of Example 5 or any other example disclosed herein, wherein the Nitinol wires are configured to move the drive pawl when alternatively activated, thereby rotating the ratchet gear in the first direction.

Example 7 is an extension of Example 6 or any other example disclosed herein, wherein the nut is configured to rotate in the first direction when the ratchet gear is rotated in the first direction.

Example 8 is an extension of Example 7 or any other example disclosed herein, further comprising a spring coupled to the nut and the second brake component.

Example 9 is an extension of Example 8 or any other example disclosed herein, wherein the spring is configured to tighten as the nut is rotated in the first direction.

Example 10 is an extension of Example 9 or any other example disclosed herein, wherein the first brake component comprises a ramp component configured to engage a stop pawl coupled to the ratchet gear when the first brake component is adjacent to the second brake component.

Example 11 is an extension of Example 10 or any other example disclosed herein, wherein the stop pawl is configured to disengage from the ratchet gear when engaged by the ramp component.

Example 12 is an extension of Example 11 or any other example disclosed herein, wherein the ratchet gear is configured to rotate in a second direction when the stop pawl is disengaged from the ratchet gear, the second direction opposite to the first direction.

Example 13 is an extension of Example 12 or any other example disclosed herein, wherein the spring is configured to unwind when the stop pawl is disengaged from the ratchet gear.

Example 14 is an extension of Example 13 or any other example disclosed herein, wherein the spring is configured to provide a force to cause the ratchet gear to rotate in the second direction when the stop pawl is disengaged from the ratchet gear.

Example 15 is an extension of Example 14 or any other example disclosed herein, wherein the first brake component, the lead screw, and the plunger coupling component are configured to remain stationary when the ratchet gear is rotated in the second direction.

Example 16 is an extension of Example 15 or any other example disclosed herein, wherein the second brake component is configured to advance toward the plunger when the ratchet gear is rotated in the second direction.

Example 17 is an extension of Example 16 or any other example disclosed herein, wherein the plunger coupling component comprises a ramp component configured to engage the stop pawl when the second brake component is adjacent to the plunger coupling component.

Example 18 is an extension of Example 17 or any other example disclosed herein, wherein the stop pawl is configured to engage the ratchet gear when the ramp component of the plunger coupling component engages the stop pawl.

Example 19 is an extension of Example 18 or any other example disclosed herein, wherein the stop pawl is configured to prevent rotation of the ratchet gear in the second direction when the stop pawl is engaged with the ratchet gear.

Example 20 is an extension of Example 1 or any other example disclosed herein, wherein the first and second brake components are self-energizing brakes.

The following fourth set of examples pertain to further embodiments.

Example 1 is a resetting lead screw drive, comprising a first brake component, a second brake component, a plunger coupling component, a lead screw positioned through the second brake component and coupled to the first brake component and the plunger coupling component, a tilt nut coupled to the lead screw, and a ratchet gear coupled to the tilt nut, wherein rotation of the ratchet gear in a first direction is configured to advance the first brake component, the lead screw, and the plunger coupling component toward a plunger positioned within a drug container to expel a portion of a stored liquid drug for delivery to a user.

Example 2 is an extension of Example 1 or any other example disclosed herein, wherein the second brake component is configured to remain stationary as the first brake component, the lead screw, and the plunger coupling component are advanced toward the plunger.

Example 3 is an extension of Example 2 or any other example disclosed herein, further comprising a drive pawl configured to rotate the ratchet gear in the first direction.

Example 4 is an extension of Example 3 or any other example disclosed herein, further comprising two or more shape memory wires coupled to the drive pawl.

Example 5 is an extension of Example 4 or any other example disclosed herein, wherein the shape memory wires are Nitinol wires.

Example 6 is an extension of Example 5 or any other example disclosed herein, wherein the Nitinol wires are configured to move the drive pawl when alternatively activated, thereby rotating the ratchet gear in the first direction.

Example 7 is an extension of Example 6 or any other example disclosed herein, wherein the tilt nut is configured to rotate in the first direction when the ratchet gear is rotated in the first direction.

Example 8 is an extension of Example 7 or any other example disclosed herein, further comprising a spring positioned between the first brake component and the second brake component.

Example 9 is an extension of Example 8 or any other example disclosed herein, wherein the spring is configured to compress as the first brake component advances toward the second brake component.

Example 10 is an extension of Example 9 or any other example disclosed herein, wherein the tilt nut comprises a first tilt nut component coupled to the ratchet gear by a first hinge and a second tilt nut component coupled to the ratchet gear by a second hinge.

Example 11 is an extension of Example 10 or any other example disclosed herein, further comprising a top hat component covering the first and second tilt nut components, respectively.

Example 12 is an extension of Example 11 or any other example disclosed herein, wherein the top hat component is configured to maintain the first tilt nut component engaged with the lead screw and the second tilt nut component engaged with the lead screw.

Example 13 is an extension of Example 12 or any other example disclosed herein, wherein the first brake component comprises a first ramp component and a second ramp component.

Example 14 is an extension of Example 13 or any other example disclosed herein, the first ramp component configured to engage a first snap component coupled to the top hat component and the second ramp component configured to engage a second snap component coupled to the top hat component when the first brake component is adjacent to the second brake component.

Example 15 is an extension of Example 14 or any other example disclosed herein, wherein the top hat component is configured to release the first tilt nut component when the first snap component is engaged by the first ramp component and the top hat component is configured to release the second tilt nut component when the second snap component is engaged by the second ramp component.

Example 16 is an extension of Example 15 or any other example disclosed herein, wherein the first tilt nut component is configured to rotate about the first hinge when released and the second tilt nut component is configured to rotate about the second hinge when released, thereby disengaging the first and second tilt nut components from the lead screw.

Example 17 is an extension of Example 16 or any other example disclosed herein, wherein the spring is configured to expand when the first and second tilt nut components disengage from the lead screw.

Example 18 is an extension of Example 17 or any other example disclosed herein, wherein the spring is configured to provide a force to advance the second brake component toward the plunger when the first and second tilt nut components disengage from the lead screw.

Example 19 is an extension of Example 18 or any other example disclosed herein, wherein the first brake component, the lead screw, and the plunger coupling component are configured to remain stationary as the second brake component is advanced toward the plunger.

Example 20 is an extension of Example 19 or any other example disclosed herein, wherein the plunger coupling component is configured to engage the top hat component when the second brake component is adjacent to the plunger coupling component.

Example 21 is an extension of Example 20 or any other example disclosed herein, wherein the top hat component is configured to re-cover the first and second tilt nut components, respectively, when engaged by the plunger coupling component.

Example 22 is an extension of Example 21 or any other example disclosed herein, wherein the first and second tilt nut components re-engage the lead screw when re-covered by the top hat component, respectively.

Example 23 is an extension of Example 1 or any other example disclosed herein, wherein the first and second brake components are self-energizing brakes.

Example 24 is an extension of Example 1 or any other example disclosed herein, wherein the drug container is an International Organization for Standardization (ISO) drug cartridge.

Example 25 is an extension of Example 24 or any other example disclosed herein, wherein the liquid drug is insulin.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. An alternate step drive for a drug delivery device, comprising:
    a first brake component configured to expand and retract along a first axis;
    a second brake component configured to expand and retract along the first axis, and
    a connector component coupled to the first and second brake components, wherein:
        the connector component is configured to expand and retract along a second axis approximately perpendicular to the first axis, and
        the first brake component, the second brake component, and the connector component are configured to advance a plunger positioned within a reservoir of the drug delivery device.

2. The alternate step drive of claim 1, wherein the first brake component, the second brake component, and the connector component are each configured to expand and retract independently of one another.

3. The alternate step drive of claim 2, wherein the first brake component comprises:
    a first non-compressible component,
    a second non-compressible component,
    a compressible component positioned between the first and second non-compressible components,
    a shape memory wire wrapped around the first and second non-compressible components,
    a first rubber component wrapped around a first end of the first brake component, and
    a second rubber component wrapped around a second end of the first brake component.

4. The alternate step drive of claim 3, wherein the shape memory wire wrapped around the first and second non-compressible components is configured to contract when activated by applying a current to the shape memory wire wrapped around the first and second non-compressible components.

5. The alternate step drive of claim 4, wherein the first non-compressible component and the second non-compressible component are configured to:
    compress the compressible component when the shape memory wire wrapped around the first and second non-compressible components is activated, thereby retracting the first brake component along the first axis; and
    expand when the shape memory wire wrapped around the first and second non-compressible components is deactivated, thereby expanding the first brake component along the first axis.

6. The alternate step drive of claim 3, wherein the first and second rubber components are configured to:
    contact an inner wall of a drug container when the first brake component is expanded along the first axis; and
    not contact the inner wall of the drug container when the first brake component is retracted along the first axis.

7. The alternate step drive of claim 1, wherein the connector component comprises:
    a shape memory wire wrapped around the first and second brake components, wherein the shape memory wire wrapped around the first and second brake components is configured to contract when activated.

8. The alternate step drive of claim 1, wherein the connector component comprises:
    a compressible component positioned between the first and second brake components.

9. The alternate step drive of claim 8, wherein the first and second brake components are configured to:
    compress the compressible component positioned between the first and second brake components when a shape memory wire wrapped around the first and second brake components is activated, thereby retracting the connector component along the second axis; and expand when the shape memory wire wrapped around the first and second brake components is deactivated, thereby expanding the connector component along the second axis.

10. The alternate step drive of claim 1, further comprising:
a controller configured to control expansion and retraction of the first brake component, the second brake component, and the connector component.

11. The alternate step drive of claim 10, wherein the controller is coupled to a shape memory wire wrapped around the first and second brake components.

12. A drug delivery device, comprising:
a reservoir configured to store a liquid drug;
a plunger disposed within the reservoir; and
an alternate step drive coupled to the reservoir, the alternate step drive including:
 a first brake component configured to expand and retract along a first axis;
 a second brake component configured to expand and retract along the first axis, and
 a connector component coupled to the first and second brake components, wherein:
  the connector component is configured to expand and retract along a second axis different from the first axis, and
  the first brake component, the second brake component, and the connector component are configured to advance the plunger positioned within the reservoir.

13. The drug delivery device of claim 12, wherein the connector component comprises:
a compressible component positioned between the first and second brake components.

14. The drug delivery device of claim 12, wherein the connector component comprises:
a shape memory wire wrapped around the first and second brake components, wherein the shape memory wire wrapped around the first and second brake components is configured to contract when activated.

15. The drug delivery device of claim 12, further comprising:
a compressible component positioned between the first brake component and the second brake component, wherein the first and second brake components are configured to:
 compress the compressible component positioned between the first brake component and the second brake component when a shape memory wire wrapped around the first and second brake components is activated, thereby retracting the connector component along the second axis; and
 expand when the shape memory wire wrapped around the first and second brake components is deactivated, thereby expanding the connector component along the second axis.

16. The drug delivery device of claim 12, wherein the first brake component comprises:
a first non-compressible component,
a second non-compressible component,
a compressible component positioned between the first and second non-compressible components,
a shape memory wire wrapped around the first and second non-compressible components,
a first rubber component wrapped around a first end of the first brake component, and
a second rubber component wrapped around a second end of the first brake component.

17. The drug delivery device of claim 16, wherein the first non-compressible component and the second non-compressible component are configured to:
compress the compressible component when the shape memory wire wrapped around the first and second non-compressible components is activated by a controller, thereby retracting the first brake component along the first axis; and
expand when the shape memory wire wrapped around the first and second non-compressible components is deactivated by the controller, thereby expanding the first brake component along the first axis.

18. The drug delivery device of claim 17, wherein the first and second rubber components are configured to:
contact an inner wall of a drug container when the first brake component is expanded along the first axis; and
not contact the inner wall of the drug container when the first brake component is retracted along the first axis.

19. The alternate step drive of claim 12, further comprising:
a receiver configured to:
 receive control signals from a remote controller, and coupled to the first brake component.

20. The alternate step drive of claim 12, further comprising:
a controller electrically coupled the first brake component and configured to control expanding and retracting of the first brake component and the second brake component.

* * * * *